US008859256B2

(12) United States Patent
Szalay et al.

(10) Patent No.: US 8,859,256 B2
(45) Date of Patent: Oct. 14, 2014

(54) METHOD FOR DETECTING REPLICATION OR COLONIZATION OF A BIOLOGICAL THERAPEUTIC

(71) Applicants: Aladar A. Szalay, Highland, CA (US); Jochen Stritzker, La Jolla, CA (US); Michael Hess, Wuerzburg (DE)

(72) Inventors: Aladar A. Szalay, Highland, CA (US); Jochen Stritzker, La Jolla, CA (US); Michael Hess, Wuerzburg (DE)

(73) Assignee: Genelux Corporation, San Diego, CA (US)

( * ) Notice: Subject to any disclaimer, the term of this patent is extended or adjusted under 35 U.S.C. 154(b) by 30 days.

(21) Appl. No.: 13/573,845

(22) Filed: Oct. 5, 2012

(65) Prior Publication Data

US 2013/0130292 A1 May 23, 2013

Related U.S. Application Data

(60) Provisional application No. 61/627,255, filed on Oct. 5, 2011.

(51) Int. Cl.
*C12N 15/52* (2006.01)
*C12N 15/86* (2006.01)
*G01N 33/569* (2006.01)
*G01N 21/64* (2006.01)
*C12Q 1/68* (2006.01)

(52) U.S. Cl.
CPC ...... *G01N 21/6428* (2013.01); *G01N 33/56911* (2013.01); *G01N 2800/52* (2013.01); *G01N 33/56983* (2013.01); *C12Q 1/6897* (2013.01)
USPC ...................................... 435/210; 435/320.1

(58) Field of Classification Search
CPC .............................. C12N 15/52; C12N 15/86
USPC .............................................. 435/210, 320.1
See application file for complete search history.

(56) References Cited

U.S. PATENT DOCUMENTS

| | | | |
|---|---|---|---|
| 4,952,496 A | 8/1990 | Studier et al. ................... 435/91 |
| 5,716,613 A | 2/1998 | Guber et al. ................... 424/93.2 |
| 5,716,826 A | 2/1998 | Gruber et al. ............... 435/320.1 |
| 5,851,529 A | 12/1998 | Guber et al. ............... 424/188.1 |
| 5,976,796 A | 11/1999 | Szalay et al. ....................... 435/6 |
| 6,428,968 B1 | 8/2002 | Molnar-Kimber et al. .. 435/7.23 |
| 6,447,784 B1 | 9/2002 | Bermudes et al. ......... 424/235.1 |
| 6,475,482 B1 | 11/2002 | Bermudes et al. ........... 424/93.4 |
| 6,632,670 B1 | 10/2003 | Wadsworth et al. .......... 435/455 |
| 6,635,472 B1 | 10/2003 | Lauermann ............... 435/320.1 |
| 6,638,752 B2 | 10/2003 | Contag et al. .............. 435/252.3 |
| 6,649,159 B2 | 11/2003 | Yang et al. .................. 424/93.21 |
| 6,653,103 B2 | 11/2003 | Peterson et al. ............. 435/69.1 |
| 6,685,935 B1 | 2/2004 | Pawelek et al. .............. 424/93.2 |
| 6,689,871 B1 | 2/2004 | Wolfe et al. ................... 530/412 |
| 6,723,316 B2 | 4/2004 | Laquerre et al. ............. 424/93.2 |
| 6,759,038 B2 | 7/2004 | Tan et al. .................... 424/93.21 |
| 6,863,894 B2 | 3/2005 | Bermudes et al. ......... 424/335.1 |
| 6,897,045 B2 | 5/2005 | Engelhardt et al. .......... 435/69.6 |
| 6,916,462 B2 | 7/2005 | Contag et al. ................... 424/9.6 |
| 6,923,972 B2 | 8/2005 | Bermudes et al. ......... 424/235.1 |
| 6,962,696 B1 | 11/2005 | Bermudes et al. ........... 424/93.4 |
| 7,001,765 B2 | 2/2006 | Maass ........................ 435/320.1 |
| 7,033,826 B2 | 4/2006 | Perricaudet et al. ....... 435/320.1 |
| 7,153,510 B1 | 12/2006 | Rose ............................ 424/199.1 |
| 7,172,893 B2 | 2/2007 | Rabinowitz et al. ........ 435/235.1 |
| 7,238,526 B2 | 7/2007 | Wilson et al. .................. 435/382 |
| 7,241,447 B1 | 7/2007 | Engelhardt et al. ........ 424/193.1 |
| 7,255,851 B2 | 8/2007 | Contag et al. ................... 424/9.1 |
| 7,354,592 B2 | 4/2008 | Bermudes et al. ......... 424/235.1 |
| 7,452,531 B2 | 11/2008 | Bermudes et al. ........... 424/93.2 |
| 7,514,089 B2 | 4/2009 | Bermudes et al. ......... 424/258.1 |
| 7,537,924 B2 | 5/2009 | Coffin et al. ................ 435/235.1 |
| 7,550,296 B2 | 6/2009 | Hermiston et al. ........... 435/473 |
| 7,588,767 B2 | 9/2009 | Szalay et al. ............... 424/199.1 |
| 7,588,771 B2 | 9/2009 | Szalay et al. ............... 424/232.1 |
| 7,662,398 B2 | 2/2010 | Szalay et al. ............... 424/232.1 |
| 7,662,627 B2 | 2/2010 | Johnson et al. ................ 435/367 |
| 7,687,474 B2 | 3/2010 | Matin et al. ..................... 514/44 |
| 7,731,952 B2 | 6/2010 | Mohr et al. .................... 424/93.2 |
| 7,731,974 B2 | 6/2010 | Bell et al. .................... 424/199.1 |
| 7,754,221 B2 | 7/2010 | Szalay et al. ............... 424/199.1 |
| 7,763,420 B2 | 7/2010 | Stritzker et al. ................... 435/4 |
| 7,811,814 B2 | 10/2010 | Bohn et al. ................. 435/320.1 |
| 7,820,184 B2 | 10/2010 | Stritzker et al. ........... 424/241.1 |

(Continued)

FOREIGN PATENT DOCUMENTS

| | | |
|---|---|---|
| EP | 1 281 767 | 2/2003 |
| EP | 1 281 772 | 2/2003 |

(Continued)

OTHER PUBLICATIONS

Iankov et al. 2009; Converting tumor-specific markers into reporters of oncolytic nirus invention. Molecular Therapy. 17(8): 1395-1403.*
Kanerva et al. 2005; Noninvasive dual modality in vivo monitoring of the persistence and potency of a tumor targeted conditionally replicating adenovirus. Gene Therapy. 12: 87-94.*
Kelly et al. 2008; Novel oncolytic agent GLV-1h68 is effective against malignant pleural mesothelioma. Human Gene Therapy 19:774-782.*
Mastrangelo et al. 1998; Intratumoral ecombinant GM-CSF-encoding virus as gene thereapy in patients with cutaneous melanoma. Cancer Gene Therapy. 6(5): 409-422.*
Peng et al. 2002; Non-invasive in vivo monitoring of trackable viruses expressing soluble marker peptides. Nature Medicine 8(5): 527-531.*

(Continued)

Primary Examiner — Karen Cochrane Carlson
(74) Attorney, Agent, or Firm — McKenna Long & Aldridge LLP; Stephanie Seidman

(57) ABSTRACT

Methods for detecting replication in or colonization of a host by a biological therapeutic, such as an oncolytic virus, cells administered for cell therapy and gene therapy vectors, are provided. In the methods, a product produced by the biological therapeutic is detected in a sample of tissue or body fluid distinct from the administered therapy or locus thereof, thereby permitting assessment of the therapy and/or monitoring its progress.

20 Claims, 6 Drawing Sheets

(56) References Cited

U.S. PATENT DOCUMENTS

| | | | |
|---|---|---|---|
| 7,897,146 B2 | 3/2011 | Brown et al. | 424/93.1 |
| 7,906,111 B2 | 3/2011 | Wilson et al. | 424/93.2 |
| 7,927,585 B2 | 4/2011 | Snyder | 424/93.2 |
| 7,943,374 B2 | 5/2011 | Hildinger | 435/320.1 |
| 7,968,340 B2 | 6/2011 | Hallek et al. | 435/440 |
| 8,007,780 B2 | 8/2011 | Arbetman | 424/93.2 |
| 8,021,662 B2 | 9/2011 | Szalay et al. | 424/138.1 |
| 8,052,968 B2 | 11/2011 | Szalay et al. | 424/199.1 |
| 8,066,984 B2 | 11/2011 | Szalay et al. | 424/93.21 |
| 8,221,769 B2 | 7/2012 | Szalay et al. | 424/232.1 |
| 8,323,959 B2 | 12/2012 | Szalay et al. | 435/320.1 |
| 8,357,486 B2 | 1/2013 | Stritzker et al. | 435/4 |
| 8,568,707 B2 | 10/2013 | Szalay et al. | 424/9.3 |
| 8,586,022 B2 | 11/2013 | Szalay et al. | 424/93.2 |
| 8,642,257 B2 | 2/2014 | Szalay et al. | 435/5 |
| 2002/0028195 A1 | 3/2002 | Coffey et al. | 424/131.1 |
| 2003/0031628 A1 | 2/2003 | Zhao et al. | 424/9.6 |
| 2003/0059400 A1 | 3/2003 | Szalay | 424/93.2 |
| 2003/0161788 A1 | 8/2003 | Zhao et al. | 424/9.6 |
| 2003/0228261 A1 | 12/2003 | Szalay et al. | 424/9.34 |
| 2004/0009604 A1 | 1/2004 | Zhang et al. | 435/456 |
| 2004/0213741 A1 | 10/2004 | Szalay et al. | 424/9.6 |
| 2004/0234455 A1 | 11/2004 | Szalay et al. | 424/9.6 |
| 2005/0031643 A1 | 2/2005 | Szalay et al. | 424/199.1 |
| 2005/0069491 A1 | 3/2005 | Yu et al. | 424/1.11 |
| 2005/0220818 A1 | 10/2005 | Lorence | 424/214.4 |
| 2005/0249670 A1 | 11/2005 | Szalay et al. | 424/9.32 |
| 2005/0260601 A1 | 11/2005 | Whitt et al. | 435/6 |
| 2006/0039894 A1 | 2/2006 | Mohr et al. | 424/93.6 |
| 2006/0051370 A1 | 3/2006 | Szalay et al. | 424/199.1 |
| 2007/0009489 A1 | 1/2007 | Bermudes et al. | 424/93.4 |
| 2007/0025981 A1 | 2/2007 | Szalay et al. | 424/130.1 |
| 2007/0098743 A1 | 5/2007 | Bell et al. | 424/224.1 |
| 2007/0110720 A1 | 5/2007 | Brown et al. | 424/93.2 |
| 2007/0202572 A1 | 8/2007 | Szalay et al. | 435/69.1 |
| 2007/0212727 A1 | 9/2007 | Szalay et al. | 435/6 |
| 2008/0124355 A1 | 5/2008 | Bermudes | 424/200.1 |
| 2008/0193373 A1 | 8/2008 | Stritzker et al. | 424/1.17 |
| 2008/0206201 A1* | 8/2008 | Beier et al. | 424/93.6 |
| 2008/0286237 A1 | 11/2008 | Kirn | 424/93.2 |
| 2009/0010889 A1 | 1/2009 | Brown et al. | 424/93.2 |
| 2009/0053244 A1 | 2/2009 | Chen et al. | 424/174.1 |
| 2009/0098529 A1 | 4/2009 | Chen et al. | 435/5 |
| 2009/0117034 A1 | 5/2009 | Chen et al. | 424/1.17 |
| 2009/0117047 A1 | 5/2009 | Szalay et al. | 424/9.3 |
| 2009/0117048 A1 | 5/2009 | Szalay et al. | 424/9.3 |
| 2009/0117049 A1 | 5/2009 | Szalay et al. | 424/9.3 |
| 2009/0123382 A1 | 5/2009 | Szalay et al. | 424/9.6 |
| 2009/0136917 A1 | 5/2009 | Szalay et al. | 435/5 |
| 2009/0155287 A1 | 6/2009 | Chen et al. | 424/158.1 |
| 2009/0162288 A1 | 6/2009 | Chen et al. | 424/9.3 |
| 2009/0169517 A1 | 7/2009 | Bermudes | 424/93.4 |
| 2009/0180955 A1 | 7/2009 | Stritzker et al. | 424/1.73 |
| 2009/0215147 A1 | 8/2009 | Zhang et al. | 435/235.1 |
| 2009/0274728 A1 | 11/2009 | Brown et al. | 424/231.1 |
| 2009/0285860 A1 | 11/2009 | Martuza et al. | 424/277.1 |
| 2009/0311664 A1 | 12/2009 | Fong et al. | 435/5 |
| 2010/0008946 A1 | 1/2010 | Szalay et al. | 424/199.1 |
| 2010/0062016 A1 | 3/2010 | Szalay et al. | 424/199.1 |
| 2010/0080775 A1 | 4/2010 | Perricaudet et al. | 435/6 |
| 2010/0092515 A1 | 4/2010 | Conner et al. | 424/231.1 |
| 2010/0113567 A1 | 5/2010 | Barber | 514/44 |
| 2010/0136048 A1 | 6/2010 | Bermudes | 424/200.1 |
| 2010/0172877 A1 | 7/2010 | van den Pol et al. | 424/93.6 |
| 2010/0178684 A1 | 7/2010 | Woo et al. | 435/235.1 |
| 2010/0196325 A1 | 8/2010 | Szalay et al. | 424/93.6 |
| 2010/0233078 A1 | 9/2010 | Szalay et al. | 424/1.17 |
| 2011/0064650 A1 | 3/2011 | Szalay | 424/1.11 |
| 2011/0158948 A1 | 6/2011 | Brown et al. | 424/93.2 |
| 2011/0177032 A1 | 7/2011 | Martuza et al. | 424/93.2 |
| 2011/0212530 A1 | 9/2011 | Baltimore et al. | 435/455 |
| 2011/0223241 A1 | 9/2011 | Tardi et al. | 424/450 |
| 2011/0293527 A1 | 12/2011 | Chen et al. | 424/9.3 |
| 2011/0300176 A1 | 12/2011 | Szalay | 424/199.1 |
| 2012/0020883 A1 | 1/2012 | Stritzker et al. | |
| 2012/0244068 A1 | 9/2012 | Chen et al. | 424/1.11 |
| 2012/0276010 A1 | 11/2012 | Szalay et al. | 424/9.1 |
| 2012/0308484 A1 | 12/2012 | Szalay et al. | 424/9.3 |
| 2013/0129614 A9 | 5/2013 | Szalay et al. | 424/1.11 |
| 2013/0273007 A1 | 10/2013 | Szalay et al. | 424/93.2 |
| 2013/0280170 A1 | 10/2013 | Szalay | 424/9.2 |
| 2014/0086976 A1 | 3/2014 | Szalay et al. | 424/445 |
| 2014/0087362 A1 | 3/2014 | Szalay et al. | 435/5 |

FOREIGN PATENT DOCUMENTS

| | | |
|---|---|---|
| EP | 1 385 466 | 2/2004 |
| EP | 1 414 994 | 5/2004 |
| EP | 1 520 175 | 4/2005 |
| EP | 1 606 411 | 12/2005 |
| WO | WO 93/01296 | 1/1993 |
| WO | WO 98/14605 | 4/1998 |
| WO | WO 03/014380 | 2/2003 |
| WO | WO 03/057007 | 7/2003 |
| WO | WO 2005/047458 | 5/2005 |
| WO | WO 2007/075879 | 7/2007 |
| WO | WO 2008/073148 | 6/2008 |
| WO | WO 2008/100292 | 8/2008 |
| WO | WO 2009/054996 | 4/2009 |
| WO | WO 2008/156655 | 6/2009 |
| WO | WO 2009/126189 | 10/2009 |

OTHER PUBLICATIONS

Rajecki et al. 2007: Treatment of prostate cancer with Ad5/3D24hCG allows non-invasive deterection of the magnitude and persistence of virus replication in vivo. Mol. Cancer Ther. 6(2): 742-751.*

Letter/Written Disclosure of the Information Disclosure Statement, mailed Feb. 22, 2013, for the above-referenced application U.S. Appl. No. 13/573,845, 2 pages.

Search Report, issued Jan. 30, 2013, in connection with corresponding International Patent Application No. PCT/US2012/059126, 8 pages.

Ahram et al., "A Proteomic approach to characterize protein shedding," Proteomics 5:123-131, (2005).

Bernt et al., "Enzyme-activated prodrug therapy enhances tumor-specific replication of adenovirus vectors," Cancer Research 62(1):6089-6098, (2002).

Gerard et al., "Real-time monitoring of cell transplantation in mouse dystrophic muscles by a secreted alkaline phosphatase reporter gene," Gene Therapy 16(6):815-819, (2009).

Ghivizzani, S., et al., "Direct retrovirus-mediated gene transfer to the synovium of the rabbit knee: implications for arthritis gene therapy," Gene Therapy 4(9):977-982, (1997).

Kanerva et al., "Noninvasive dual modality in vivo monitoring of the persistence and potency of a tumor targeted conditionally replicating adenovirus," Gene Therapy 12(1):87-94, (2005).

Nagy et al., "Systemic delivery of a recombinant protein by genetically modified mesothelial cells reseeded on the parietal peritoneal surface," Gene Therapy 2(6):402-410, (1995).

Peng et al., "Non invasive in vivo monitoring of trackable viruses expressing soluble marker peptides," Nature Medicine 8(5):527-531, (2002).

Svensjoe et al., "Cultured autologous fibroblasts augment epidermal repair," Transplantation 73(7):1033-1041, (2002).

Chen et al., "Tropism of oncolytic Vaccinia virus constructs for human mononuclear cell subsets," 27th Annual Meeting Final Program, Society for Immunotherapy of Cancer (SITC), Oct. 26-28, 2012, North Bethesda, MD. [oral presentation abstract] 1 page.

Olsson et al., "The use of the luxA gene of the bacterial luci ferase operon as a reporter gene," Mol. Gen. Genet. 215(1):1-9, (1988).

Rehemtulla et al., "Rapid and quantitative assessment of cancer treatment response using in vivo bioluminescence imaging," Neoplasia 2(6):491-495, (2000).

Reinboth et al., "Correlation between human and oncolytic Vaccinia virus transcriptional profile," 27th Annual Meeting Final Program, Society for Immunotherapy of Cancer (SITC), Oct. 26-28, 2012, North Bethesda MD. [Poster 82 abstract] 1 page.

Weintraub, A., "Pet dogs help biotech startups find new weapons to fight cancer," X conomy, Jul. 25, 2012, [online] [retrieved on Jan. 28,

(56) References Cited

OTHER PUBLICATIONS

2013] [Retrieved from:<URL:xconomy.com/san-diego/2012/07/25/pet-dogs-help-biotech-start ups-find-new-weapons-to-fight-cancer/?single_page=true], 7 pages.
AACR Presi Release Sep. 15, 2011, Virus shows promise for imaging and treating pancreatic cancer, Published on Sep. 15, 2011 [online][retrieved on Jan. 28, 2013] Retrieved from:<URL:aacr.org/home/public—media/aacr-press--releases.aspx?d=2438, 2 pages.
Genelux Press Release Nov. 1, 2012, "Genelux corporation announces early results of a phase I/II clinical trial of virotherapeutic GL-ONC1 in advanced peritoneal cavity cancers," [online] Published on Nov. 1, 2012 [online][retrieved on Jan. 28, 2013] Retrieved from:<URL:genelux.com/genelux2012/?page_id=4157, 3 pages.
Genelux Press Release Jun. 28, 2012, "Genelux corporation announces ground-breaking clinical study evaluating oncolytic *Vaccinia virus* in canine cancer patients," [online] Published on Jun. 28, 2012 [online][retrieved on Jan. 28, 2013] Retrieved from:<URL:genelux.com/genelux2012/?page_id=3824, 2 pages.
Genelux Press Release Jun. 14, 2012, "Genelux corporation announces first patient dosed in phase I combination clinical trial of GL-ONC1," [online] Published on Jun. 14, 2012 [online][retrieved on Jan. 28, 2013] Retrieved from:<URL:genelux.com/genelux2012/?page_id=2701, 2 pages.
Genelux Press Release May 31, 2012, "Genelux corporation announces treatment of first patient in phase I/II clinical trial of GL-ONC1 in advanced peritoneal cavity cancers," [online] Published on May 31, 2012 [online][retrieved on Jan. 28, 2013] Retrieved from:<URL:genelux.com/genelux2012/?page_id=2691, 2 pages.
Genelux Press Release May 30, 2012, "Genelux corporation announces phase I data presentation at 2012 ASCO Annual Meeting of GL-ONC1, its oncolytic virus lead product candidate," [online] Published on May 30, 2012 [online][retrieved on Jan. 28, 2013] Retrieved from:<URL:genelux.com/genelux2012/?page_id=2686&preview=true, 2 pages.
Genelux Press Release Jun. 6, 2011, "ASCO poster presentation unveils preliminary results of phase I clinical trial involving intraveneous administration of GL-ONC1 to patients with advanced solid tumor cancers," [online] Published on Jun. 6, 2011 [retrieved on Jan. 28, 2013] Retrieved from:<URL: genelux.com/genelux2012/?page_id=1357, 1 page.
Adams et al., "The c-myc oncogene driven by immunoglobulin enhancers induces malignancy in transgenic mice," Nature 318(6046): 533-538, (1985).
Agranovski et al. "Rapid detection of airborne viruses by personal bioaerosol sampler combined with the PCR device." (2006) Atmospheric Environment 40:3924-3929 (2006).
Alexander et al., "Expression of the c-myc oncogene under control of an immunoglobulin enhancer in E mu-myc transgenic mice," Mol Cell Biol. 7(4): 1436-1444, (1987).
Altenhoefer et al., "The probiotic *Escherichia coli* strain Nissle 1917 interferes with invasion of human intestinal epithelial cells by different enteroinvasive bacterial pathogens," FEMS Immunol. Med. Microbiol. 40(3):223-229 (2004).
Al'tshtein et al., "Isolation of a recombinant *Vaccinia virus* based on the LIVP strain inducing the surface antigen of the hepatitis B virus," Dokl. Akad. Nauk. SSSR 285(3):696-699 (1985) [Article in Russian].
Al'tshtein [Altshteyn] et al., "[Isolation of a recombinant *Vaccinia virus* based on the LIVP strain inducing the surface antigen of the hepatitis B virus]," Dokl Akad Nauk SSSR. 285(3):696-699 (1985) [Article in Russian] Certified English translation.
Antunes et al., "Synthesis and evaluation of [18F]-FEAnGA as a PET tracer for β-glucuronidase activity," Bioconjug Chem 21:911-920 (2010).
Barbé et al., "Secretory production of biologically active rat interleukin-2 by clostridium acetobutylicum DSM792 as a tool for anti-tumor treatment," FEMS Microbiol Lett. 246(1):67-73 (2005).
Barak et al., "Role of nitric oxide in *Salmonella typhimurium*-mediated cancer cell killing," BMC Cancer 10:146, 6 pages (2010).
Barrett, A., "Yellow fever vaccines," Biologicals 25:17-25 (1997).

Bennett et al., "Positron emission tomography imaging for herpes virus infection: implications for oncolytic viral treatments of cancer," Nature Med. 7(7):859-863 (2001).
Bernoist, C. and P. Chambon, "In vivo sequence requirements of the SV40 early promoter region," Nature 290(5804):304-310, (1981).
Bevis, B. and B. Glick, "Rapidly maturing variants of the Discosoma red fluorescent protein (DsRed)," Nat. Biotechnol., 20(1):83-87 (2002).
Blum et al., "Intravenous iron supplementation for the treatment of the anemia of moderate to severe chronic renal failure patients not receiving dialysis," Infection 23(4):234-236 (1996).
Brinster et al., "Regulation of metallothionein—thymidine kinase fusion plasmids injected into mouse eggs," Nature 296(5852): 39-42 (1982).
Broder et al., "Recombinant vaccinia viruses," Mol. Biotechnol. 13:223-245 (1999).
Browne et al., "Cancer screening by systemic administration of a gene delivery vector encoding tumor-selective secretable biomarker expression," PLoS One 6:(5):e19530 (2011), 9 pages.
Carrillo et al., "The multiple sequence alignment problem in biology," SIAM J. Applied Math 48:1073-1082 (1988).
Chakrabarti et al., "Compact, synthetic, *Vaccinia virus* early/late promoter for protein expression," BioTechniques 23(6):1094-1097 (1997).
Chen et al., "A novel recombinant *Vaccinia virus* expressing the human norepinephrine transporter retains oncolytic potential and facilitates deep tissue imaging," Mol. Med. 15(5-6):144-151 (2009).
Chen et al., "Directed evolution of a lysosomal enzyme with enhanced activity at neutral pH by mammalian cell-surface display," Chem. Biol. 15:1277-1286 (2008).
Chen et al., "A humanized immunoenzyme with enhanced activity for glucuronide prodrug activation in the tumor microenvironment," Bioconjug. Chem. 22(5): 938-948 (2011).
Cheng et al., "Tumor-targeting prodrug-activating bacteria for cancer therapy," Cancer Gene Ther. 15(6):393-401 (2008).
Chkheidze et al., "Identification of DNA binding proteins in *Vaccinia virus* by DNA-protein crosslinking," FEBS 336(2):340-342 (1993).
King et al., "Tumor-targeted *Salmonella typhimurium* overexpressing cytosine deaminase: a novel, tumor-selective therapy," Methods Mol Biol. 542: 649-659 (2009).
Cronin et al., "Orally administered bifidobacteria as vehicles for delivery of agents to systemic tumors," 18(7):1397-1407 (2010).
Davison et al., "New *Vaccinia virus* recombination plasmids incorporating a synthetic late promoter for high level expression of foreign proteins," Nucleic Acids Res. 18:4285-4286 (1990).
Davison et al., "Structure of *Vaccinia virus* early promoters," J. Mol. Biol. 210:749-769 (1989).
de Boer et al., "The tac promoter: a functional hybrid derived from the trp and lac promoters," Proc. Natl. Acad. Sci. USA 80:21-25 (1983).
de Graaf et al., "Pronounced antitumor efficacy by extracellular activation of a doxorubicin-glucuronide prodrug after adenoviral vector-mediated expression of a human antibody-enzyme fusion protein," Human Gene Ther. 15(3): 229-238 (2004).
Devereux et al., "A comprehensive set of sequence analysis programs for the VAX," Nucleic Acids Res. 12(1):387-395 (1984).
Dingli et al., "Image-guided radiovirotherapy for multiple myeloma using a recombinant measles virus expressing the thyroidal sodium iodide symporter," Blood 103(5): 1641-1646 (2004).
Earl et al., in Ausubel et al., (eds.) found in *Current protocols in molecular biology*, vol. 3, pp. 16.17.1-16.19-7 (1998).
Fang et al., "A Fluorometric β-glucuomidase assay for analysis of bacterial growth in milk," Vet. Microbiol. 46(4):361-367 (1995).
Fidler, I. and L. Ellis, "The implications of angiogenesis for the biology and therapy of cancer metastasis," Cell 79(2): 185-188 (1994).
Friedlos et al., "Attenuated Salmonella targets prodrug activating enzyme carboxypeptidase G2 to mouse melanoma and human breast and colon carcinomas for effective suicide gene therapy," Clinical Cancer Research 14:4259-4266 (2008).
Gardner et al., "The complete nucleotide sequence of an infectious clone of cauliflower mosaic virus by M13mp7 shotgun sequencing," 9(12):2871-2888 (1981).

(56) References Cited

OTHER PUBLICATIONS

Gribskov et al., "Sigma factors from *E. coli, B. subtilis*, phage SP01, and phage T4 are homologous proteins," Nucl. Acids Res. 14:6745-6763 (1986).

Grosschedl et al., "Introduction of a mu immunoglobulin gene into the mouse germ line: specific expression in lymphoid cells and synthesis of functional antibody," Cell 38(3):647-658 (1984).

Grozdanov et al., "Analysis of the genome structure of the nonpathogenic probiotic *Escherichia coli* strain Nissle 1917," J Bacteriol. 186(16):5432-5441 (2004).

Haddad et al., "Insertion of the human sodium iodide symporter to facilitate deep tissue imaging does not alter oncolytic or replication capability of novel *Vaccinia virus*," J. Translational Med. 9:36, 13 pages (2011).

Hammer et al., "Diversity of alpha-fetoprotein gene expression in mice is generated by a combination of separate enhancer elements," Science 235(4784):53-58 (1987).

Hanahan, D., "Heritable formation of pancreatic beta-cell tumours in transgenic mice expressing recombinant insulin/simian virus 40 oncogenes," Nature 315(6015):115-122 (1985).

Heine et al., "Cell surface display of a lysosomal enzyme for extracellular gene-directed enzyme prodrug therapy," Gene Ther. 8(13):1005-1010 (2001).

Heo et al., "Sequential therapy with JX-594, a targeted oncolytic poxvirus, followed by sorafenib in hepatocellular carcinoma: preclinical and clinical demonstration of combination efficacy," Mol Ther. 19(6):1170-1179 (2011).

Herrera-Estrella et al., "Expression of chimaeric genes transferred into plant cells using a Ti-plasmid-derived vector," Nature 303:209-213 (1983).

Herrera-Estrella et al., "Light-inducible and chloroplast-associated expression of a chimaeric gene introduced into *Nicotiana tabacum* using a Ti plasmid vector," Nature 310:115-120 (1984).

Hess et al., "Bacterial glucuronidase as general marker for oncolytic virotherapy or other biological therapies," J. Translational Medicine 9:172, 12 pages, Epub date Oct. 11, 2011.

Hu et al., "*Bifidobacterium longum* as a delivery system of TRAIL and endostatin cooperates with chemotherapeutic drugs to inhibit hypoxic tumor growth," Cancer Gene Ther. 16(8):655-663 (2009).

Huang et al., "Enhancement of CPT-11 antitumor activity by adenovirus-mediated expression of β-glucuronidase in tumors," Cancer Gene Ther. 18(6):381-389 (2011).

Islam et al., "C-terminal processing of human beta-glucuronidase. The propeptide is required for full expression of catalytic activity, intracellular retention, and proper phosphorylation," J. Biol. Chem. 268(30):22627-22633 (1993).

"IUPAC-IUB commission on biochemical nomenclature a one-latter notation for amino acid sequences tentative rules," J. Biol. Chem. 243(13): 3557-3559 (1968).

IUPAC-IUB commission on bio-chemical nomenclature symbols for amino-acid derivatives and peptides. Recommendations (1971). Biochem. 11(9):1726-1732 (1972).

Jain et al., "Structure of human beta-glucuronidase reveals candidate lysosomal targeting and active-site motifs," Nat Struc Biol 3(4):375-381 (1996).

Jay et al., "Construction of a general vector for efficient expression of mammalian proteins in bacteria: Use of synthetic ribosome binding site," 78(9):5543-5548, (1981).

Jefferson et al., "Beta-Glucuronidase from *Escherichia coli* as a gene-fusion marker," Proc. Natl. Acad. Sci. USA 83(22):8447-8451 (1986).

Jefferson et al., "GUS fusions: beta-glucuronidase as a sensitive and versatile gene fusion marker in higher plants," EMBO J. 6(13):3901-3907 (1987).

Joklik, W., "The purification of four strains of poxviruses," Virology 18:9-18 (1962).

Kapoor et al., "Efficacy of antimicrobial peptoids against *Mycobacterium tuberculosis*," Antimicrob. Agents Chemother. 55(6):3058-3062 (2011).

Kauffman et al., "Metastasis suppression: the evolving role of metastasis suppressor genes for regulating cancer cell growth at the secondary site," J Urol. 169(3):1122-1133 (2003).

Kelsey et al., "Species- and tissue-specific expression of human alpha 1-antitrypsin in transgenic mice," Genes Dev. 1(2):161-171 (1987).

Kilian, M. and P. Bulow, "Rapid diagnosis of Enterobacteriaceae. I. Detection of bacterial glycosidases," Acta Pathol. Microbiol. Scand. B, 84B(5):245-251 (1976).

Kim et al., "Crystallization and preliminary X-ray analysis of endoglucanase from *Pyrococcus horikoshii*," Acta Crystallogr Sect F Struct Biol Cryst Commun, 64(Pt 12):1169-1171 (2008).

King et al., "Tumor-targeted *Salmonella* expressing cytosine deaminase as an anticancer agent," Hum. Gene Ther. 13(10):1225-1233 (2002).

King et al., "Tumor-targeted *Salmonella typhimurium* overexpressing cytosine deaminase: a novel, tumor-selective therapy," Methods Mol Biol. 542:649-659 (2009).

Kirn, D. and S. Thorne, "Targeted and armed oncolytic poxviruses: novel multi-mechanistic therapeutic class for cancer," Nat. Rev. Cancer 9:64-71 (2009).

Kollias et al., "Regulated expression of human A gamma-, beta-, and hybrid gamma beta-globin genes in transgenic mice: manipulation of the developmental expression patterns," Cell 46(1):89-94 (1986).

Kozak, M., "Structural features in eukaryotic mRNAs that modulate the initiation of translation," J. Biol. Chem. 266:19867-19870 (1991).

Kozlova et al., "Inactiviation and mineralization of aerosol deposited model pathogenic microorganisms over $TiO_2$ and $Pt/TiO_2$," Environ. Sci. Technol. 44:5121-5126 (2010).

Kruis, W., "Review article: antibiotics and probiotics in inflammatory bowel disease," Aliment. Pharmacol. Ther. 20 (Suppl 4): 75-78 (2004).

Krumlauf et al., "Developmental regulation of alpha-fetoprotein genes in transgenic mice," Mol Cell Biol. 5(7):1639-1648 (1985).

Kutinova et al., "Hepatitis B virus proteins expressed by recombinant vaccinia viruses: influence of preS2 sequence on expression surface and nucleocapsid proteins in human diploid cells," Arch. Virol. 134:1-15 (1994).

Kutinova et al., "Search for optimal parent for recombinant *Vaccinia virus* vaccines. Study of three *Vaccinia virus* vaccinal strains and several virus lines derived from them," Vaccine 13(5):487-493 (1995).

Leder et al., "Consequences of widespread deregulation of the c-myc gene in transgenic mice: multiple neoplasms and normal development," Cell 45(4):485-495 (1986).

Leslie A., "Refined crystal structure of type III choramphenicol acetyltransferase at 1.75 resolution," J. Mol. Biol. 213(1): 167-186 (1990).

Li et al., "The oncopathic potency of *Clostridium perfringens* is independent of its alpha-toxin gene," Hum Gene Ther. 20(7):751-758 (2009).
Liu et al., "The Targeted oncolytic poxvirus JX-594 demonstrates antitumoral, antivascular, and anti-HBV activities in patients with hepatocellular carcinoma," Mol. Ther. 16(9):1637-1642 (2008).
Low et al., "Construction of VNP200009: a novel, genetically stable antibiotic-sensitive strain of tumor-targeting *Salmonella* for parenteral administration in humans," Methods Mol. Med. 90:47-59 (2004).
Macdonald, R., "Expression of the pancreatic elastase I gene in transgenic mice," Hepatology 7(S1):42S-51S (1987).
Magram et al., "Developmental regulation of a cloned adult beta-globin gene in transgenic mice," Nature 315(6017):338-340 (1985).
Mason et al., "The hypogonadal mouse: reproductive functions restored by gene therapy," Science 234(4782):1372-1378 (1986).
Matthews, B., "The structure of *E. coli* beta-galactosidase," C. R. Biol. 328(6):549-556 (2005).
Matz et al., "Fluorescent proteins from nonbioluminescent Anthozoa species," Nat. Biotech. 17:969-973 (1999).
Mayford et al., "CaMKII regulates the frequency-response function of hippocampal synapses for the production of both LTD and LTP," Cell 81: 891-904 (1995).
McAllister et al., "Recombinant yellow fever viruses are effective therapeutic vaccines for treatment of murine experimental solid tumors and pulmonary metastases," J. Virol. 74:9197-9205 (2000).

(56) References Cited

OTHER PUBLICATIONS

Möse and Möse, "Oncolysis by clostridia. I. Activity of *Clostridium butyricum* (M-55) and other nonpathogenic clostridia against the ehrlich carcinoma," Cancer Res. 24:212-216 (1964).
Moss, B., "Genetically engineered poxviruses for recombinant gene expression, vaccination, and safety," Proc. Natl. Acad. Sci. U.S.A. 93:11341-11348 (1996).
Moss, B., "Poxvirus vectors: cytoplasmic expression of transferred genes," Curr. Opin. Genet. Dev. 3:86-90 (1993).
Nagai et al., "A variant of yellow fluorescent protein with fast and efficient maturation for cell-biological applications," Nat. Biotechnol. 20(1):87-90 (2002).
Nathoo et al., "Pathobiology of brain metastases," J Clin Pathol 58(3):237-242 (2005).
Needleman et al., "A general method applicable to the search for similarities in the amino acid sequences of two proteins," J. Mol. Biol. 48:443-453 (1970).
Nguyen, A. and P. Daugherty, "Evolutionary optimization of fluorescent proteins for intracellular FRET," Nat Biotechnol. 23(3):355-360 (2005).
Ornitz et al., "Elastase I promoter directs expression of human growth hormone and SV40 T antigen genes to pancreatic acinar cells in transgenic mice," Cold Spring Harb Symp Quant Biol 50:399-409 (1985).
Oshima et al., "Cloning, sequencing, and expression of cDNA for human beta-glucuronidase," Proc Natl Acad Sci USA, 84(3):685-689 (1987).
Oshima et al., "Cloning, sequencing, and expression of cDNA for human beta-galactosidase," Biochem Biophys Res Commun 157(1):238-244 (1988).
Park et al., "Use of a targeted oncolytic poxvirus, JX-594, in patients with refractory primary or metastatic liver cancer: a phase I trial," Lancet Oncol. 9(6):533-542 (2008).
Patel et al., "A poxvirus-derived vector that directs high levels of expression of cloned genes in mammalian cells," Proc. Natl. Acad. Sci. U.S.A. 85:9431-9435 (1988).
Pawelek et al., "Bacteria as tumour-targeting vectors," Lancet Oncol. 4:548-556 (2003).
Pearson et al., "Improved tools for biological sequence comparison," Proc. Natl. Acad. Sci. U.S.A. 85:2444-2448 (1988).
Pedersen et al., "A phase I clinical trial of genetically modified and imageable oncolytic *Vaccinia virus* GL-ONC1 with clinical green fluorescent protein (GFP) imaging," J. Clin. Oncol 29:2011 (abstr 2577) [Abstract] ASCO Annual Meeting, Jun. 3-7, 2011, 3 pages.
Pedersen et al., "A phase I clinical trial of genetically modified and imageable oncolytic *Vaccinia virus* GL-ONC1 with clinical green fluorescent protein (GFP) imaging," J. Clin. Oncol 29: 2011 (abstr 2577) [Poster] ASCO Annual Meeting, Jun. 3-7, 2011, 1 page.
Pinkert et al., "An albumin enhancer located 10 kb upstream functions along with its promoter to direct efficient, liver-specific expression in transgenic mice," Genes Dev. 1:268-276 (1987).
Puhlmann et al., "*Vaccinia* as a vector for tumor-directed gene therapy: biodistribution of a thymidine kinase-deleted mutant," Cancer Gene Ther. 7(1):66-73 (2000).
Readhead et al., "Expression of a myelin basic protein gene in transgenic shiverer mice: correction of the dysmyelinating phenotype," Cell 48(4):703-712 (1987).
Rizzo et al., "An improved cyan fluorescent protein variant useful for FRET," Nat Biotechnol. 22(4):445-449 (2004).
Sambrook et al., found in *Molecular Cloning: A Laboratory Manual*, 2nd Ed., Cold Spring Harbor Press, p. B.13 (1989).
Sartor R., "Probiotic therapy of intestinal inflammation and infections," Curr. Opin. Gastroenterol. 21(1):44-50 (2005).
Schultz et al., "Green fluorescent protein for detection of the probiotic microorganism *Escherichia coli* strain Nissle 1917 (EcN) in vivo," J. Microbiol. Methods 61(3):389-398 (2005).
Schwartz, R. and M. Dayhoff, eds., "Matrices for detecting distant relationships," in *Atlas of protein sequence and structure*, Chapter 23, National Biomedical Research Foundation, pp. 353-358 (1979).
Shaner et al., "A guide to choosing fluorescent proteins," Nat Methods. 2(12):905-909 (2005).
Shani M., "Tissue-specific expression of rat myosin light-chain 2 gene in transgenic mice," Nautre 314(6008):283-286 (1985).
Shchelkunov et al., "The gene encoding the late nonstructural 36K protein of *Vaccinia virus* is essential for virus reproduction," Virus Res. 28:273-283 (1993).
Shcherbo et al., "Bright far-red fluorescent protein for whole-body imaging," Nat. Methods 4:741-746 (2007).
Shine, J. and L. Dalgarno, "Determinant of cistron specificity in bacterial ribosomes," Nature 254(5495):34-38 (1975).
Shipley et al., "The role of glycosylation and phosphorylation in the expression of active human beta-glucuronidase," 268(16):I2193-12198 (1993).
Shkrob et al., "Far-red fluorescent proteins evolved from a blue chromoprotein from Actinia equine," Biochem J. 392(Pt 3):649-654 (2005).
Smith et al., "Comparison of biosequences," Adv. Appl. Math. 2:482-489 (1981).
Soghomonyan et al., "Positron emission tomography (PET) imaging of tumor-localized *Salmonella* expressing HSV1-TK", Cancer Gene Ther. 12(1):101-108 (2005).
Sroller et al., "Effect of 3-beta-hydroxysteroid dehydrogenase gene deletion on virulence and immunogenicity of different Vaccinia viruses and their recombinants," Arch. Virol. 143:1311-1320 (1998).
Stahl, P. and W. Fishman, "Beta-D-glucuronidase," In: Bergmeyer, J. and M. Grassi eds. *Methods in enzymatic analysis*. Weinheim, Germany: Verlag Chemie, pp. 246-256 (1984).
Sterenczak et al., "Cloning, characterization, and comparative quantitative expression analyses of receptor for advanced glycation end products (RAGE) transcript forms," Gene 424(102):35-42 (2008).
Stritzker et al., "Tumor-specific colonization, tissue distribution, and gene induction by probiotic *Escherichia coli* Nissle 1917 in live mice", Int. J. Med. Microbiol. 297(3):151-162 (2007).
Su et al., "Gene expression imaging by enzymatic catalysis of a fluorescent probe via membrane-anchored beta-glucuonidase," Gene Ther. 14(7):565-574 (2007).
Swift et al., "Tissue-specific expression of the rat pancreatic elastase I gene in transgenic mice," Cell 38(3):639-646 (1984).
Taniguchi et al., "Targeting solid tumors with non-pathogenic obligate anaerobic bacteria," Cancer Science 101:1925-1932 (2010).
Theys et al., "*Clostridium* as a tumor-specific delivery system of therapeutic proteins," Cancer Detect Prev. 25(6):548-557 (2001).
Timiryasova et al., "Construction of recombinant vaccinia viruses using PUV-inactivated virus as a helper," BioTechniques 31:534-540 (2001).
Tzou et al., "Micro-PET imaging of beta-glucuronidase activity by the hydrophobic conversion of a glucuronide probe," Radiology 252(3):754-762 (2009).
Vidal et al., "Tissue-specific control elements of the Thy-1 gene," EMBO J. 9(3):833-840 (1990).
Wagner et al., "Nucleotide sequence of the thymidine kinase gene of herpes simplex virus type I," Proc. Natl. Acad. Sci. USA 78(3):1441-1445 (1981).
Wang et al., "Specific activation of glucuronide prodrugs by antibody-targeted enzyme conjugates for cancer therapy," Cancer Res. 52:4484-4491 (1992).
Wang et al., "Highly sensitive rapid chemiluminescent immunoassay using the DNAzyme label for signal amplification," Analyst 136:4295-4300 (2011).
Wang et al., "Evolution of new nonantibody proteins via iterative somatic hypermutation," Proc Natl Acad Sci USA. 101(48):16745-16749 (2004).
Watson et al., found in *Molecular Biology of the Gene*, 4th Edition, 1987, The Benjamin/Cummings Pub. co., p. 224.
Wei et al., "Bacterial targeted tumour therapy-dawn of a new era," Cancer Lett. 259(1):16-27 (2008).
Welch et al., "What defines a useful marker of metastasis in human cancer?" J Natl Cancer Inst. 91(16):1351-1353 (1998).
Weyel et al., "Secreted human β-glucuronidase: a novel tool for gene-directed enzyme prodrug therapy," Gene Ther. 7:224-231 (2000).

(56) References Cited

OTHER PUBLICATIONS

Wiedenmann et al., "A far-red fluorescent protein with fast maturation and reduced oligomerization tendency from *Entacmaea quadricolor* (Anthozoa, Actinaria)," Proc Natl Acad Sci U S A. 99(18):11646-11651 (2002).
Yamamoto et al., "Identification of a functional promoter in the long terminal repeat of *Rous sarcoma virus*," Cell 22(3):787-797 (1980).
Yamamoto et al., "Isolation, characterization, and mapping of a human acid beta-galactosidase cDNA," DNAa Cell Biol. 9(2):119-127 (1990).
Yoshida et al., "Metastasis-suppressor genes: a review and perspective on an emerging field," J Natl Cancer Inst 92(21): 1717-1730 (2000).
Yu et al. "Visualization of tumors and metastases in live animals with bacteria and *Vaccinia virus* encoding light-emitting proteins," Nat. Biotech. 22(3):313-320 (2004).
Zhang et al., "Eradication of solid human breast tumors in nude mice with an intravenously injected light emitting oncolytic *Vaccinia virus*," Cancer Res. 67(20):10038-10046 (2007).
Zhu et al., "Antitumor effect of sFlt-1 gene therapy system mediated by Bifidobacterium Infantis on Lewis lung cancer in mice," 18(12):884-896 (2011).
Zimmermann et al., "Independent regulatory elements in the nestin gene direct transgene expression to neural stem cells," Neuron 12:11-24 (1994).
Zinoviev et al., "Identification of the gene encoding *Vaccinia virus* immunodominant protein p35," Gene 147:209-214 (1994).
Advani et al., "Preferential replication of systemically delivered oncolytic *Vaccinia virus* to focally irradiated glioma xenografts," Clin. Cancer Res. 18(9):2579-2590 (2012).
Advani et al., "Radiotargeting systemically administered oncolytic *Vaccinia virus* to preferentially replicate in radiated gliomas," Abstract, ASTRO 53rd Annual Meeting, Miami Beach, FL, Oct. 2-6, 2011 [1 page].
Ascierto et al., "Permissivity of the NCI-60 cancer cell lines to oncolytic *Vaccinia virus* GLV-1H68," BMC Cancer 11 (1):451[epub ahead of print] (2011), 27 pages.
Bermudes et al., "Live bacteria as anticancer agents and tumor-selective protein delivery vectors," Curr. Opin. Drug Disc. 5(2):194-199 (2002).
Brader et al., "*Escherichia coli* Nissle 1917 facilitates tumor detection by positron emission tomography and optical imaging", Clin. Cancer Res. 14(8):2295-2302 (2008).
Brader et al., "Imaging genetically engineered oncolytic *Vaccinia virus* (GLV-1h99) using a human norepinephrine transporter reporter gene," Clin. Cancer Res. 15(11):3791-3801 (2009).
Bronstein et al. "Chemiluminscence: sensitive detection technology for reporter gene assays," Clin Chem. 42:1542-1546 (1996).
Browne et al., "Cancer screening by systemic administration of a gene delivery vector encoding tumor-selective secretable biomarker expression," PLoS One 6:(5):e19530, 9 pages (2011).
Certified English translation of Stritzker and Szalay, "*E. coli* Nissle 1917: Vom Kriegsveteran weiterentwickelt zum aktiven Kämpfer gegen Tumoren? *E. coli* Nissle 1917: From War Veteran to Genetically-Directed Tumor Fighter" GenomXpress, 4.07, 12-14. (2007) Review. Full text.
Certified English translation of Timiryasova et al., "Analysis of reporter gene expression in various regions of the genome of the *Vaccinia virus*," Mol. Biol. 27(2):2-1 1 (1993) [Article in Russian].
Chakrabarti et al., "*Vaccinia virus* expression vector: coexpression of β-galactosidase provides visual screening of recombinant virus plaques," Mol. Cell Biol. 5:3403-3409 (1985).
Chaudhuri et al., "Light-based imaging of green fluorescent protein-positive ovarian cancer xenografts during therapy," Gynecol. Oncol. 82(3):581-589 (2001).
Chen et al., "Real-time monitoring of *Vaccinia virus* infection in cultured cells and in living mice using light-emitting proteins," Proceedings of the 14th International Symposium on Bioluminescence & Chemiluminescence: Chemistry, Biology and Applications, World Scientific: Singapore: 181-184 (2007).

ClinicalTrials.gov, "Safety study of GL-ONC1, an oncolytic virus, in patients with advanced solid tumors," [online][retrieved on Dec. 2, 2008] Retrieved from: <URL:clinicaltrials.gov/ct2/show/NCT00794131?term=genelux&rank= 1 [4 pages].
Condeelis et al., "Intravital imaging of cell movement in tumours," Nat. Rev. Cancer 3:921-930 (2003).
Contag et al., "Photonic detection of bacterial pathogens in living hosts," Mol. Microbiol. 18:593-603 (1995).
Contag et al., "Visualizing gene expression in living mammals using a bioluminescent reporter," Photochem. Photobiol. 66(4):523-531 (1997).
Corral et al., "Phase I clinical trial of genetically modified and oncolytic *Vaccinia virus* GL-ONC1 with green fluorescent protein imaging," [poster] 7th NCRI Cancer Conference, Liverpool, UK. Nov. 6-9, 2011, 1 page.
Corral et al., " Phase I clinical trial of genetically modified and oncolytic *Vaccinia virus* GL-ONC1 with green fluorescent protein imaging " [abstract] 7th NCRI Cancer Conference, Liverpool, UK. Nov. 6-9, 2011, 2 pages.
Coupar et al., "A general method for the construction of recombinant vaccinia viruses expressing multiple foreign genes," Gene 68:1-10 (1988).
Francisco et al., "Transport and anchoring of beta-lactamase to the external surface of *Escherichia coli*," PNAS USA 89:2713-2717 (1992).
Frentzen et al., "Anti-VEGF single-chain antibody GLAF-1 encoded by oncolytic *Vaccinia virus* significantly enhances antitumor therapy," Proc. Natl. Acad. Sci. U.S.A. 106(31):12915-12920 (2009).
Haddad et al., "A *Vaccinia virus* encoding the human sodium iodide symporter facilitates long-term image monitoring of virotherapy and targeted radiotherapy of pancreatic cancer ," J. Nucl. Med. 53:1933-1942, epublish Nov. 8, 2012. (2012).
Harrington, K., "GL-ONC1 Phase I Trial at Royal Marsden Hospital," Roche-Genelux Meeting, Penzberg, Germany, Sep. 19, 2011, poster, 25 pages.
He et al., "Effective oncolytic vaccinia therapy for human sarcomas," J. Surg. Res. 175(2):e53-e60 (2012).
Jacobs et al., "Positron emission tomography-based imaging of transgene expression mediated by replication-conditional, oncolytic herpes simplex virus type I mutant vectors in vivo," Cancer Res. 61:2983-2995 (2001).
Jacobs et al. "Positron-emission tomography of vector-mediated gene expression in gene therapy for gliomas," Lancet 358:727-729 (2001).
Kelly et al., "Real-time intraoperative detection of melanoma lymph node metastases using recombinant *Vaccinia virus* GLV-1h68 in an immunocompetent animal model," Int. J. Cancer 124(4):911-918 (2009).
Liu et al., "Visualizing and quantifying protein secretion using a Renilla luciferase-GFP fusion protein," Luminescence 15(1):45-49 (2000).
Loessner et al., "Remote control of tumour-targeted *Salmonella enterica* serovar Typhimurium by the use of L-arabinose as inducer of bacterial gene expression in vivo," Cell. Microbiol. 9(6):1529-1537 (2007).
Louie et al., "In vivo visualization of gene expression using magnetic resonance imaging," Nature Biotechnol. 18:321-325 (2000).
Malhotra et al., "Use of an oncolytic virus secreting GM-CSF as combined oncolytic and immunotherapy for treatment of colorectal and hepatic adenocarcinomas," Surgery 141(4):520-529 (2007).
Massoud et al., "Molecular imaging in living subjects: seeing fundamental biological processes in a new light," Genes Dev. 17:545-580 (2003).
Meighen et al., "Molecular biology of bacterial bioluminescence," Microbiol. Rev. 55(1):123-142 (1991).
Pawelek et al., "Tumor-targeted *Salmonella* as a novel anticancer vector," Cancer Res. 57(20):4537-4544 (1997).
Pfleiderer et al., "Requirements for optimal expression of secreted and nonsecreted recombinant proteins in *Vaccinia virus* systems," Protein Exp. Purif. 6(5):559-569 (1995).
Riedel et al., "Improved luciferase tagging system for Listeria monocytogenes allows real-time monitoring in vivo and in vitro," Appl. Environ. Microbiol. 73:3091-3094 (2007).

(56) References Cited

OTHER PUBLICATIONS

Rodriguez et al., "Expression of the firefly luciferase gene in *Vaccinia virus*: a highly sensitive gene marker to follow virus dissemination in tissues of infected animals," Proc. Natl. Acad. Sci. U.S.A. 85(5):1667-1671 (1988).
Stritzker and Szalay, "*E. coli* Nissle 1917: Vom Kriegsveteran weiterentwickelt zum aktiven Kämpfer gegen Tumoren? *E. coli* Nissle 1917: From War Veteran to Genetically-Directed Tumor Fighter" GenomXpress, 4.07, 12-14. (2007) Review. Full text [German].
Timiryasova et al., "Visualization of *Vaccinia virus* infection using the renilla-luciferase-GFP fusion protein," Bioluminescence & Chemiluminescence: Proceedings of the 11th International Symposium on Bioluminescence Chemiluminescence: Asilomar Conference Grounds, Pacific Grove, Monterey, California: Sep. 6-10, 2000 / (eds.): Case, J.F. et al., World Scientific Publishing Co. (c2001), pp. 457-460.
Timiriasova et al., "Analysis of reporter gene expression in various regions of the genome of the *Vaccinia virus*," Mol. Biol. (Mosk.) 27(2):392-401 (1993) [article in Russian, English abstract on last page of article].
Wang et al., "Renilla luciferase-Aequorea GFP (Ruc-GFP) fusion protein, a novel dual reporter for real-time imaging of gene expression in cell cultures and in live animals," Mol. Genet. Genomics. 268(2):160-168 (2002).
Yu et al., "Establishment and characterization of conditions required for tumor colonization by intravenously delivered bacteria" Biotechnology and Bioengineering 100(3):567-578 (2008).
Yu et al., "Examinations of bacterium-mediated detection of tumors in mice models". In: Proceedings of the 14th International Symposium on Bioluminescence & Chemiluminescence: Chemistry, Biology and Applications. World Scientific: Singapore: 209-212 (2007).
Yu et al., "Optical imaging: bacteria, viruses, and mammalian cells encoding light-emitting proteins reveal the locations of primary tumors and metastases in animals,"Anal. Bioanal. Chem. 377(6):964-972 (2003).
Yu et al., "Real-time imaging of tumors using replication-competent light emitting microorganisms," Methods Mol. Biol. 872:159-175 (2012).
Zhao et al., "Spatial-temporal imaging of bacterial infection and antibiotic response in intact animals," Proc. Natl. Acad. Sci. 98(17): 9814-9818 (2001).
Letter/Written Disclosure of the Supplemental Information Disclosure Statement for the above-referenced application, mailed Apr. 30, 2014, 2 pages.
Ahrens et al., "In vivo imaging platform for tracking immunotherapeutic cells," Nature Biotechnology 23(8):983-987 (2005).
Altschul et al., "Basic local alignment search tool," J. Mol. Biol. 215:403-410 (1990).
Belin et al., "An oncolytic *Vaccinia virus* expressing the human sodium iodine symporter prolongs survival and facilitates SPECT/CT imaging in an orthotopic model of malignant pleural mesothelioma," Surgery 154(3):486-495 (2013).
Biondo et al., "Phase I clinical trial of a genetically modified oncolytic *Vaccinia virus* GL-ONC1 with green fluorescent protein imaging," European Journal of Cancer 47:S162 (2011).
Bosnar et al., "Subcellular localization of A and B Nm23/NDPK subunits," Experimental Cell Research 298(1): 275-284 (2004).
Buckel et al., "Combination of fractionated irradiation with anti-VEGF expressing *Vaccinia virus* therapy enhances tumor control by simultaneous radiosensitization of tumor associated endothelium," Int. J. Cancer [article in press doi: 10.1002/ijc.28296], 30 pages (2013).
ClinicalTrials.gov, "A Study of GL-ONC1, an oncolytic *Vaccinia virus*, in patients with advanced peritoneal carcinomatosis," [online][retrieved on Oct. 7, 2013] Retrieved from: <URL:clinicaltrials.gov/ct2/show?term=genelux&rank=1>, 4 pages.
ClinicalTrials.gov, "Intra-pleural administration of GL-ONC1, a genetically modified *Vaccinia virus*, in patients with malignant pleural effusion: primary, metastases and mesothelioma," [online][retrieved on Oct. 7, 2013] Retrieved from:<URL:clinicaltrials.gov/ct2/show?term=genelux&rank=4>, 4 pages.
ClinicalTrials.gov, "Safety study of attenuated *Vaccinia virus* (GL-ONC1)with combination therapy in head & neck cancer," [online][retrieved on Oct. 7, 2013] Retrieved from:<URL:clinicaltrials.gov/ct2/show?term=genelux&rank=2>, 4 pages.
Dai et al., "Oncolytic *Vaccinia virus* in combination with radiation shows synergistic antitumor efficacy in pancreatic cancer," Cancer Lett. 344(2):282-290 (2014).
Duggal et al., "*Vaccinia virus* expressing bone morphogenetic protein-4 in novel glioblastoma orthotopic models facilitates enchanced tumor regression and long-term survival," J. of Translational Medicine 11:155 [article in press doi:10.1186/1479-5876-11-155], 14 pages (2013).
FASEB Public Release Jan. 30, 2014, "Engineered virus is effective against triple negative breast cancer cells" [online] [retrieved Mar. 24, 2014] Retrieved from:<URL:eurekalert.org/pub_releases/2014-01/foas-evi013014.php#, 1 page.
Fikes, B. "New tool finds, fights cancer," San Diego Union-Tribune, Published Feb. 11, 2013, 1 page (2013).
Fong et al., "Fluorescence-expressing viruses allow rapid identification and separation of rare tumors cells in spiked samples of human whole blood," Surgery 146(3):498-505 (2007).
Garcia-Aragoncillo et al., "Design of virotherapy for effective tumor treatment," Curr Opin Mol Ther 12:403-411 (2010).
Genelux Press Release, "Virus engineered to express melanin offers new possibilities to diagnose and treat solid tumor cancers," Published on Feb. 11, 2013 [online] [retrieved on Jul. 3, 2013] Retrieved from:<URL:genelux.com/february-11-2013//, 2 pages.
Genelux Press Release, "First patient treated in Genelux Phase I trial with GL-ONC1 at Memorial Sloan Kettering Cancer Center," Published on Feb. 5, 2013 [online][retrieved on Jul. 3, 2013] Retrieved from:<URL:genelux.com/february-05-2013/, 3 pages.
Genelux Press Release, "Genelux presents abstracts at the 7th international meeting on replicating oncolytic virus therapeutics in Quebec," Published on Jun. 15, 2013 [online][retrieved on Jul. 3, 2013] Retrieved from:<URL:genelux.com/june-15-2013/, 2 pages.
Genelux Press Release, "Industry veteran with more than 25 years experience will lead development and european commercialization and growth," Published on Jun. 27, 2013 [online][retrieved on Oct. 7, 2013] Retrieved from:<URL:genelux.com/june-27-2013/, 2 pages.
Genelux Press Release, "Genelux corporation presents abstracts at 2013 ASCO annual meeting for clinical trials of GL-ONC1, its oncolytic virus lead product candidate," Published on May 30, 2013 [online][retrieved on Jul. 3, 2013] Retrieved from:<URL:genelux.com/may-30-2013/, 2 pages.
Genelux Press Release Nov. 18, 2013, "Genelux Corporation's GL-ONC1 selected by Elsevier among its 'Top 10 Oncology Projects to Watch'" [online] [retrieved Mar. 21, 2014] Retrieved from:<URL:genelux.com/november-18-2013/, 2 pages.
Gholami et al., "*Vaccinia virus* GLV-1h153 in combination with 131I shows increased efficiency in treating triple-negative breast cancer," FASEB Journal, Published online before print Nov. 1, 2013 [article in press doi:10.1096/fj.13-237222], 7 pages (2013).
Haddad et al., "Imaging characteristics, tissue distribution, and spread of a novel oncolytic *Vaccinia virus* carrying the human sodium iodide symporter," PLoS One. 7(8):e41647, 13 pages (2012).
Jun et al., "A novel oncolytic viral therapy and imaging technique for gastric cancer using a genetically engineered *Vaccinia virus* carrying the human sodium iodide symporter," J Exp & Clin Cancer Res 33:2 (2014).
Karapanaqiotou et al., "Enhanced in vitro and in vivo cytotoxicity of combined *Vaccinia virus* strain GLV-1h68 and chemotherapy in melanoma," European Journal of Cancer 47:S659 (2011).
Kyula et al., "Synergistic cytotoxicity of radiation and oncolytic Lister strain vaccinia in V600D/EBRAF mutant melanoma depends on JNK and TNF-alpha signaling," Oncogene [article in press doi: 10.1038/onc.2013], 1-13 (2013).
Lauer et al., "Phase I/II clinical trial of a genetically modified and oncolytic *Vaccinia virus* GL-ONC1 in patients with unresactable,

(56) References Cited

OTHER PUBLICATIONS chemotherapy-resistant peritoneal carcinomatosis," Journal of Clinical Oncology, 2013 ASCO Annual Meeting Proceedings 31 (15 Supple):3098 (2013).
Li et al., "Intrinsic resistance of tumorigenic breast cancer cells to chemotherapy," J. Natl. Cancer Inst. 100(9):672-679 (2008).
Lin et al., "Treatment of anaplastic thyroid carcinoma in vitro with a mutant *Vaccinia virus*," Surgery 142(6):976-983 (2007).
Morscher et al., "Imaging virus-mediated melanin production using Multispectral Optoacoustic Tomography (MSOT)," British Society for Gene and Cell Therapy Conference Abstracts, P0015, Human Gene Therapy 24:A16(2013).
Nguyen et al., "*Vaccinia virus*-mediated expression of human erythropoietin in tumors enchances virotherapy and alleviates cancer-related anemia in mice," Mol Ther. 21(11):2054-2062 (2013).
Pencavel et al., "Administration of oncolytic *Vaccinia virus* GLV1h68 by isolated limb perfusion to an immunocompetent rat model of advanced extremity sarcoma," European Journal of Cancer 47:S663 (2011).
Perez-Alvarez et al., "Sarcoidosis in two patients with chronic hepatitis C treated with interferon, ribavirin and amatadine," J of Viral Hepatitis 9:75-79 (2002).
Qian et al., "Gene-viral vectors: a promising way to target tumor cells and express anticancer genes simultaneously." Chinese Medical Journal 115(8):1213-1217 (2002).
Reno, "Exclusive: Does San Diego Biotech Firm Have a Cure for Cancer?" The Reno Dispatch [online] [retrieved on Oct. 7, 2013] [retrieved from http://therenodispatch.blogspot.com/2013/07/exclusive-does-san-diego-biotech-firm.html].
Ruiz-Hernandez et al., "PEG-pHPMAm-based polymeric micelles loaded with doxorubicin-prodrugs in combination antitumor therapy with oncolytic vaccinia viruses." Polym Chem. 7(5):1674-1681 (2014).
Stritzker, J. and A. Szalay, "Single-agent combinatorial cancer therapy," Proc. Natl. Acad. Sci. USA 110(21):8325-8326 (2013).
Stroncek et al., "Highlights of the society for immunotherapy of cancer (SITC) 27th annual meeting." Journal for ImmunoTherapy of Cancer 1:4 (2013).
Tahan et al., "Sarcoidosis after use of interferon for chronic hepatitis C," Digestive Diseases and Sciences 48(1):169-173 (2003).
Vitfell-Pedersen et al., "Preliminary results of a Phase 1 study of intravenous administration of GL-ONC1 *Vaccinia virus* in patients with advanced solid cancer with real time imaging." In 6th NCRI Cancer Conference; BT Convention Center, Liverpool, UK. 2010, [abstract] European J Cancer Supplements 8(7):23 (2010).
Wang et al., "Optical detection and virotherapy of live metastatic tumor cells in body fluids with vaccinia strains," PLoS One 3:8(9):e71105, 12 pages (2013).
Weibel et al., "Treatment of malignant effusion by oncolytic virotherapy in an experimental subcutaneous xenograft model of lung cancer," J. Transl. Med. 11:106 (2013).
International Preliminary Report on Patentability, issued Apr. 8, 2014, in connection with corresponding International Patent Application No. PCT/US2012/059126, 11 pages.
Letter/Written Disclosure of the Information Disclosure Statement mailed Apr. 29, 2013, for the above-referenced application, U.S. Appl. No. 13/573,845, 2 pages.
Gholami et al., "*Vaccinia virus* GLV-1h153 is a novel agent for detection and effective local control of positive surgical margins for breast cancer," Breast Cancer Res 15(2):R26, 32 pages (2013).
Stritzker et al., "*Vaccinia virus*-mediated melanin production allows MR and optoacoustic deep tissue imaging and laser-induced thermotherapy of cancer," Proc. Natl. Acad. Sci. Feb. 11, 2013 [Epub ahead of print PMID 23401518], 1-5 (2013).
Written Opinion, issued Apr. 16, 2013, in connection with corresponding International Patent Application No. PCT/US2012/059126, 20 pages.

\* cited by examiner

METHOD FOR DETECTING REPLICATION OR COLONIZATION OF A BIOLOGICAL THERAPEUTIC

RELATED APPLICATIONS

Benefit of priority is claimed to U.S. provisional Application No. 61/627,255, filed Oct. 5, 2011, entitled "Method for Detecting Replication or Colonization of a Biological Therapeutic."

This application is related to corresponding International Application No. PCT/US12/059126, filed the same day herewith, entitled "Method for Detecting Replication or Colonization of a Biological Therapeutic," which claims priority to U.S. provisional Application No. 61/627,255, filed Oct. 5, 2011. The subject matter of each of the above-noted applications is incorporated by reference in its entirety.

INCORPORATE BY REFERENCE OF SEQUENCE LISTING PROVIDED ON COMPACT DISCS

An electronic version on compact disc (CD-R) of the Sequence Listing is filed herewith in duplicate (labeled Copy #1 and Copy #2), the contents of which are incorporated by reference in their entirety. The computer-readable file on each of the aforementioned compact discs, created on Oct. 5, 2012, is identical, 3.1 megabytes in size, and titled 4838seq.001.txt.

APPLICATIONS INCORPORATED BY REFERENCE

The following applications and patents, which describe inter alia, viruses and bacteria and methods of preparing and using such viruses and bacteria, are incorporated by reference: U.S. Pat. Nos. 7,588,767, 7,588,771, 7,662,398, 7,754,221, 7,763,420, 7,820,184, 8,021,662, 8,052,968, 8,066,984, 8,221,769 and U.S. Patent Publication Nos. 2011/0300176, 2007/0202572, 2007/0212727, 2010/0062016, 2009/0098529, 2009/0053244, 2009/0155287, 2009/0117034, 2010/0233078, 2009/0162288, 2010/0196325, 2009/0136917, 2011/0064650, 2003/0059400, 2004/0234455, 2005/0069491, 2009/0117049, 2009/0117048, 2009/0117047, 2009/0123382, 2003/0228261, 2004/0213741 and 2005/0249670 and U.S. patent application Ser. No. 13/506,369.

FIELD OF THE INVENTION

Methods for detecting replication or colonization of a biological therapeutic are provided.

BACKGROUND

Biological therapies, such as gene therapies, cell therapies and oncolytic viral therapies, are viable treatment modalities. Monitoring their administration and effectiveness, however, is difficult. Hence, there exists a need for a facile, generally applicable method for detecting or assessing, gene expression, cell colonization or infection determining tumor colonization and/or gene expression in subjects treated with biological therapies. These and other needs are addressed herein.

SUMMARY

Provided are methods for detecting replication in a subject and/or colonization of a target locus in the subject by a biological therapeutic, such as a therapeutic virus, or detecting replication of the biological therapeutic in a cell the subject by detecting the presence of a protein that is encoded by the biological therapeutic separate from the biological therapeutic or the cell in which it is expressed. When a biological therapeutic, such as an oncolytic virus, is administered, its ability to effect treatment depends upon its ability to accumulate in target cells, such as tumor cells. For oncolytic viruses this requires that the virus colonize target cells and replicate therein to lyse the target cells. Upon replication, gene expression occurs and virally encoded proteins are expressed. When the cells lyse or otherwise release proteins, the virally encoded proteins or products thereof appear in body fluids, such as blood, plasma and urine. The virally encoded proteins and products are not necessarily secreted products, but they appear in body fluids because cells have lysed. The methods herein detect such proteins and products.

The methods herein are practiced by obtaining a sample from a subject to whom the therapeutic has been administered; and then testing the sample to detect the protein encoded by the biological therapeutic or a product thereof. Detection of the protein or product indicates that the biological therapeutic is replicating in or colonizing a target locus. Generally the protein, when expressed, is not operatively linked to a signal sequence so that it is not secreted. The protein or product is referred to herein as a reporter protein, and the nucleic acid encoding it is a reporter gene. The protein can be detected directly or indirectly. Presence of the protein in such a sample indicates that the biological therapeutic is replicating and/or its genes are being expressed in the host to which it is administered. The sample generally is obtained from a locus in the subject other than a target of the biological therapeutic, unless, the target is tumor of such locus, such as leukemia. Generally, the sample comprises a body fluid, or is a sample that does not contain the biological therapeutic. When the sample contains the biological therapeutic, testing is effected under conditions or is corrected or normalized, such that expression from the biological therapeutic in the sample is not considered. The reporter protein encoded by the biological therapeutic can be an endogenous protein or a heterologous protein, and typically is a detectable protein or is a protein, such as an enzyme, that can produce a detectable signal. Reporter proteins include, but are not limited to, enzymes, antigens and enzyme substrates. Detection can include, for example, contacting the sample with a substrate if the reporter is an enzyme and detecting a product catalyzed by the enzyme. Where the reporter protein is an antigen, detection can be effected by capturing with an antibody or other binding molecule, such as an antibody presented on a nanoparticle.

Exemplary of the methods are methods of detecting tumors by administering a pox virus, such as a vaccinia virus to a subject. The virus encodes an enzyme, such as a beta-glucuronidase, such as a bacterial beta-glucuronidase; and the method then includes obtaining a body fluid sample, such as blood, urine, CSF or other body fluid; and detecting beta-glucuronidase activity in the sample, where detection of activity indicates the presence of tumor cells in the subject. The method can detect the presence of tumors or tumor cells, such as circulating tumor cells and metastasizing cells, in the subject and also can be employed to monitor tumor therapy, including therapy with the administered vaccinia virus, which serves as a theranostic. The pox viruses, such as vaccinia viruses, include any known to those of skill in the art and any described herein.

Subjects include any subject, including but not limited to any animal. The animals include humans, veterinary animals, pets, farm animals, animal models. Included are human, cats, dogs, frogs, ferrets, gorillas, chimpanzees, gorillas, birds, lions, tigers, cows, rodents, goats, pigs, chickens, horses, zebras, dolphins and whales.

Biological therapeutics, include, but are not limited to, viruses, particularly oncolytic viruses, such as vaccinia viruses, gene therapy vectors, including viruses, cells for cell therapy, such as adoptive immunotherapy, transplanted cells, autologous cell therapy, stem cell therapy, bacteria, particularly non-pathogenic bacteria that accumulate in tumor cells and other immunoprivileged cells and tissues; nucleic acids in vectors or in delivery vehicles, such as targeted liposomes. Exemplary of viruses are oncolytic viruses, such as vaccinia viruses, particularly those that accumulate in immunoprivileged cells, such as tumors. Such viruses include, vaccinia viruses derived from the lister strain, such as LIVP viruses and derivatives thereof, including viruses modified to include heterologous nucleic acid.

Oncolytic viruses include, but are not limited to, poxvirus, oncolytic adenovirus, reovirus, herpes virus, adeno-associated virus, lentivirus, retrovirus, rhabdovirus, papillomavirus, vesicular stomatitis virus, measles virus, Newcastle disease virus, picornavirus, sindbis virus, papillomavirus, parvovirus, coxsackievirus, influenza virus, mumps virus, poliovirus and semliki forest virus. In some instances, the viruses, such as adenoviruses, must be modified to be oncolytic (i.e. selectively replicate and ultimately lyse tumor cells). Poxviruses include, but are not limited to viruses selected from among orthopoxvirus, parapoxvirus, avipoxvirus, capripoxvirus, leporipoxvirus, suipoxvirus, molluscipoxvirus, yatapoxvirus, entomopoxvirus A, entomopoxvirus B and entomopoxvirus C.

Vaccinia viruses, such as Lister strain viruses, including LIVP viruses, including clonal variants and clonal isolates of such viruses are contemplated for administration. Exemplary LIVP viruses and isolates and derivatives thereof include the virus designated GLV-1h68, described herein and known to those of skill in the art, and derivatives (viruses that are produced from GLV-1h68 or related viruses) and modified form thereof. Exemplary of such viruses are any whose genomes comprise a sequence of nucleotides set forth in any of SEQ ID NOS:82-83 and 85-91, or a sequence of nucleotides that has at least 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity to a sequence of nucleotides set forth in any of SEQ ID NOS: 82-83 and 85-91. Exemplary of such viruses that are derivatives or related to GLV-1h68 as defined above, are those designated GLV-1h22, GLV-1i69, GLV-1h70, GLV-1h71, GLV-1h72, GLV-1h73, GLV-1h74, GLV-1h80, GLV-1h81, GLV-1h82, GLV-1h83, GLV-1h84, GLV-1h85, GLV-1h86, GLV-1j87, GLV-1j88, GLV-1j89, GLV-1h90, GLV-1h91, GLV-1h92, GLV-1h96, GLV-1h97, GLV-1h98, GLV-1h99, GLV-1h100, GLV-1h101, GLV-1h104, GLV-1h105, GLV-1h106, GLV-1h107, GLV-1h108, GLV-1h109, GLV-1h139, GLV-1h143, GLV-1h146, GLV-1h150, GLV-1h151, GLV-1h152 and GLV-1h153. These viruses can be modified, if they do not express a reporter, to express a desired reporter gene or protein, such as a glucuronidase. As shown herein, glucuronidase and products thereof result in a highly sensitive system for detecting as few as a single cell in a sample. Thus, such system can be used for early detection of tumors, as well as for monitoring therapy.

The oncolytic viruses accumulate in tumors, but as shown herein, non-tumor samples, such as urine, blood, serum and other body fluids can be tested to detect the presence of viral encoded proteins. The presence of the protein outside of the cells that contain the virus indicates that the virus has colonized the cells and is replicating. Encoded proteins are shed as the cells are lysed. Cells, such as tumors, when infected with the virus, become protein factors and can produce large amounts of proteins. Hence, administration of a virus (or other biological therapeutic) can be assessed by detecting the presence of encoded protein. As shown herein, the presence of tumors as small as 1 mm$^3$ or even smaller can be detected. Thus, the methods herein permit diagnosis of tumors. The methods herein also permit detection of circulating tumor cells.

In addition, the methods can be used to assess the effectiveness of therapy. Detection of a protein encoded by a biological therapeutic indicates that it is being expressed and/or replicating (depending upon the therapeutic). Hence the methods can monitor treatment to discern whether viral colonization of a target locus has been established. Therapy also can be monitored over time. The particular results to detect depend upon the type of therapy. For example, for tumor therapy, initially, there should be detectable protein expressed, but as tumors are cleared and disappear the amount of protein will decrease. For gene therapy methods in which nucleic acids become part of the genome, longer periods of expression may be expected, and instances permanent levels of expression may be expected. The methods herein permit monitoring of any such type of therapy. For example, subjects treated with such therapy, can be periodically monitored through blood or urine or other body fluid samples.

The therapeutic virus can be administered topically, locally and systemically, including enterally or parenterally. Such methods include, but are not limited to, administration that is effected orally, epicutaneously, intranasally, by gastric feeding tube, duodenal feeding tube, or gastrostomy, rectally, intravenously, intraarterially, intramuscularly, intracardiacly, subcutaneously, by intraosseous infusion (into the bone marrow), intradermally, intraperitoneally, intrapleurally, transdermally, transmucosally, epidurally, intrathecally, intraventricularly or intratumorally.

The dosage administered and/or administration regimen depend upon the biological therapeutic administered and its purpose. For the oncolytic vaccinia virus, including any described herein, dosages typically include at least or about $1 \times 10^5$ or about $1 \times 10^5$ plaque forming units (PFU), $5 \times 10^5$ or about $5 \times 10^5$ PFU, at least $1 \times 10^6$ or about $1 \times 10^6$ PFU, $5 \times 10^6$ or about $5 \times 10^6$ PFU, $1 \times 10^7$ or about $1 \times 10^7$ PFU, $5 \times 10^7$ or about $5 \times 10^7$ PFU, $1 \times 10^8$ or about $1 \times 10^8$ PFU, $5 \times 10^8$ or about $5 \times 10^8$ PFU, $1 \times 10^9$ or about $1 \times 10^9$ PFU, $5 \times 10^9$ or about $5 \times 10^9$ PFU, $1 \times 10^{10}$ or about $1 \times 10^{10}$ PFU or $5 \times 10^{10}$ or about $5 \times 10^{10}$ PFU as total single dosage for an average human of 75 kg or adjusted for the weight and size and species of the subject and the mode of administration. One of skill in the art can determine suitable dosage. Suitable dosages for any biological therapeutic can be determined empirically.

Viruses and vectors administered include those selected from among a retrovirus, adenovirus, adeno-associated virus and herpes simplex virus. The vectors can be administered as naked nucleic acid or in a suitable delivery vehicle, including, for example, a liposome, PEGylated liposome, nanoparticle, lipid-based nanoparticle or lymphocyte.

The oncolytic viruses, such as vaccinia virus, and the bacteria, such as attenuated or non-pathogenic bacterium, accumulate in immunoprivileged cells and tissues, which are cells and tissues, such as inflamed/wounded tissues, particularly inside a subject, and tumors, which tissues are sheltered or not exposed to the immune system, which clears the viruses and bacteria from other sites. Immunoprivileged cells and tissues include sites of cellular proliferation, such as tumors, tumor tissues, metastases, areas of inflammation, wounds and infections. Bacteria, particularly attenuated or non-pathogenic bacteria, include a mutual, commensal or probiotic strain of bacteria or an attenuated pathogenic bacterium. Strains of bacteria include, but are not limited to bacteria selected from among *Escherichia coli, Bacteroides, Eubacterium, Streptococcus, Actinomyces, Veillonella, Nesseria, Prevotella, Campylobacter, Fusobacterium, Eikenella, Porphyromonas, Priopionibacteria, Clostridia, Salmonella, Shigella, Bifidobacteria* and *Staphylococcus* species. Such bacteria include the probiotic *E. coli* bacterium, Nissle, such as Nissle 1917.

Cell therapies include, but are not limited to, cell transplants, such as, for example, cell transplants selected from among pancreatic islet, bone marrow, endothelial, epidermal, myoblast, neural and stem cell transplants. Biological therapies that include expression vectors and gene therapy vectors, include, but are not limited to, a viral vector, mammalian vector, bacterial vector, insect vector, plant vector or artificial chromosome encoding the reporter gene, such as retroviruses, satellite artificial chromosomes, baculoviruses, vaccinia viruses and others well known to those of skill in the art. For cell therapies, detection can be effected by infecting or transfecting or transducing the cell with nucleic acid encoding the reporter protein. The nucleic acid can be introduced on a vector, virus, bacterium or artificial chromosome including any listed elsewhere herein. Generally for cell therapy the nucleic acid is introduced prior to administration to subject.

For practicing the methods, as noted, any protein encoded by the biological therapeutic can be detected. These include enzyme or enzymatic reporter proteins (i.e., proteins that catalyze a reaction when contacted with a substrate). The nucleic acid encoding the enzyme, typically is not linked to nucleic acid encoding a secretory signal, but instead occurs in tissues and body fluids of a subject upon shedding by a cell containing the biological therapeutic or the cell that is a biological therapeutic. For enzymes, typically, the sample or an aliquot of the sample or treated sample to adjust conditions or purify or partially purify the reporter protein, is contacted with substrate for the enzyme. A product that is produced by this reaction is detected. Exemplary of this are oncolytic viruses, such as vaccinia viruses, that encode an enzyme, particularly a bacterial enzyme not normally expressed in the treated subject. In addition, the biological therapeutic can be a cell or gene therapy vector or oncolytic virus; and detecting the shed reporter enzyme assesses the progress of cancer therapy, immunotherapy, adoptive immunotherapy or gene therapy administered in connection with cancer therapy, immunotherapy, adoptive immunotherapy or gene therapy.

For cancer therapy the tumors include solid tumors, blood and lymphatic cancers and metastases, including, but are not limited to tumors selected from among a bladder tumor, breast tumor, prostate tumor, glioma tumor, adenocarcinoma; ovarian carcinoma, and pancreatic carcinoma, liver tumor and skin tumor, pancreatic cancer, non-small cell lung cancer, multiple myeloma, leukemia, lung and bronchus tumor, breast tumor, colon and rectum tumor, kidney tumor, stomach tumor, esophagus tumor, liver and intrahepatic bile duct tumor, urinary bladder tumor, brain tumor and other nervous system tumor, head and neck tumor, oral cavity tumor and pharynx tumor, cervix tumor, uterine corpus tumor, thyroid tumor, ovary tumor, testes tumor, prostate tumor, malignant melanoma, cholangiocarcinoma, thymoma, non-melanoma skin cancer; hematologic tumor, malignancy, childhood leukemia and lymphoma, multiple myeloma, Hodgkin's disease, lymphomas of lymphocytic and cutaneous origin, acute and chronic leukemia, acute lymphoblastic leukemia, acute myelocytic leukemia, chronic myelocytic leukemia, plasma cell neoplasm or lymphoid neoplasm and cancers associated with AIDS. In addition, administered biological therapeutics include wounds and inflamed tissues inside of a subject (not visible to the naked eye) that can be detected or for which therapy is monitored.

As noted any protein encoded by the virus can be employed as a reporter. Typically such proteins include enzymes and antibodies and antigens and other readily detectable proteins or proteins that induce or produce a detectable signal. Detection, as noted, provides for detecting tumors and also monitoring therapy with biological therapeutic. Such therapies include oncolytic viral therapy, gene therapy, cell therapy, immunotherapy, adoptive immunotherapy or gene therapy. The protein to be detected, the reporter protein, generally is operatively linked to a promoter. The promoter can be constitutive or inducible promoter or otherwise regulatable. The protein, such as those expressed by the vaccinia virus, can be linked to a secretory signal, but generally are not, since the method detects shed proteins indicative, in the case of oncolytic viruses, production of protein in tumor cells and shedding by such cells, typically by cell lysis or leakage.

As noted, the reporter gene can be an endogenous protein to the subject or to the biological therapeutic or can be heterologous and encoded by the biological therapeutic. Included are eukaryotic and prokaryotic proteins, such as enzymes. Enzymes include, but are not limited to, enzymes selected from among lipases, phospholipases, sulfatases, ureases, peptidases, proteases, esterases, phosphatases, acid phosphatases, glycosidases, glucosidases, glucuronidases, galactosidases, carboxylesterases, luciferases, peroxidases, hydrolases, oxidoreductases, lyases, transferases, isomerases, ligases, synthases, protein kinases, esterases, isomerases, glycosylases, synthetases, dehydrogenases, oxidases, reductases, methylases, oxidases, P450 enzymes, monoamine oxidases (MAOs), flavin monoamine oxidases (FMOs), transferases, glutathione S transferases (GSTs), alkaline phosphatases (AP), invertases, luciferases, acetyltransferases, beta-glucuronidases, exo-glucanases, glucoamylases, beta-glucosidases, horseradish peroxidases, alkaline phosphatases, beta-lactamases, alpha-amylases, alpha-glucosidases, catalases, beta-xylosidases, beta-galactosidases, chondroitinsulfatases, gelatinases, collagenases, caseinases, nitroreductases, azoreductases, demethylases, deacetylases, deformylases, phosphatases, kinases, peroxidases, sulfotases, acetylcholinesterases, dehydrogenases, dealkylases and oxygenases. Exemplary are β-glucuronidase, β-galactosidase, luciferase, chloramphenicol acetyltransferase (CAT) and alkaline phosphatase.

Enzymes are detected by contacting the sample with a suitable substrate whose product is detectable, such by a change in optical properties of the sample. Substrates can be fluorescent, luminescent, spectrophotometric, fluorogenic or chromogenic substrate or the substrate is a contrast agent or generates a contrast agent for PET imaging or generate products with such properties. Detection can be effected by any detection method known to those of skill in the art suitable for the particular product or change in property in a sample. Detection methods and properties, include, but are not limited to, PET imaging, MRI, mass spectrometry, and optical methods, such as methods that employ, for example, a spectrophotometer, fluorometer, luminometer, scintillation counter or a Raman spectrometer and other such devices. Products generated or substrates (whose conversion to product is detectable) can be detected.

In the methods herein, the reporter protein, as noted, can be a β-glucuronidase, including a mammalian, such as human, and bacterial β-glucuronidase, such as one that includes a sequence of amino acids set forth in SEQ ID NO: 121 or SEQ ID NO:4, or an active portion thereof, or an enzyme that that exhibits at least 85% sequence identity to a sequence of amino acids set forth in SEQ ID NO:121 or SEQ ID NO: 4 or an active portion thereof. Other β-glucuronidase enzymes include any (or active portions thereof) having at least 85% sequence identity thereto or to the active portion, include those whose sequences are set forth in any of SEQ ID NOS: 1-11, 114-121 and 127-146.

In the methods the enzymatic reporter protein can be a β-glucuronidase (as described herein), and the substrate is any suitable substrate, including but not limited to, any selected from among fluorescein di-β-D-glucuronide (FDGlcU), 4-methylumbelliferyl-β-D-glucuronide (4-MUG), carboxyumbelliferyl β-D-glucuronide (CUGlcU), 5-(pentafluorobenzoylamino)fluorescein di-β-D-glucuronide (PFB-FDGlcU), $C_{12}$-Fluorescein β-D-Glucuronidase, 5-bromo-4-chloro-3-indolyl β-D-glucuronide (X-GlcU or BCIG), p-nitrophenyl-β-D-glucuronide, Red-β-D-GlcU,CHA (Magenta-b-D-GlcA; 5-bromo-6-chloro-3-indolyl-b-D-glucuronide, cyclohexylammonium salt), Rose-β-D-GlcU,CHA (Salmon-β-D-GlcUA; 5-bromo-6-chloro-3-indolyl-β-D-glucuronide, cyclohexylammonium salt), phenyl-β-D-glucuronide, and suitable salts or other forms thereof. For example, the enzymatic reporter protein can β-glucuronidase and the substrate selected from among fluorescein di-β-D-glucuronide (FDGlcU) and 4-methylumbelliferyl-β-D-glucuronide (4-MUG). The β-glucuronidase encoded by the virus can be employed to detect circulating tumor cells (CTCs). The virus that expresses the β-glucuronidase (or other reporter) is administered, and then body fluids, such as blood and serum and plasma, that can contain CTCs are sampled. A substrate for the encoded enzyme is added to the sample and detection of the product of enzyme and substrate indicates the presence of circulating tumor cells. The cells can be quantified, and their present and numbers measured over time to assess therapeutic effectiveness of the any therapy.

Another exemplary enzymatic reporter protein is β-galactosidase, including any form thereof, prokaryotic or eukaryotic or modified forms. Exemplary substrates therefore include, but are not limited to, 4-Methylumbelliferyl β-D-galactopyranoside, Fluorescein β-D-galactopyranoside (FDG), 5-(Pentafluorobenzoylamino)-fluorescein β-D-galactopyranoside, C2-Fluorescein β-D-galactopyranoside, C12-Fluorescein β-D-galactopyranoside, 5-Chloromethylfluorescein β-D-galactopyranoside, C12-Resorufin, DDAO and Resorufin and 5-bromo-4-chloro-3-indolyl-β-D-galactopyranoside (X-gal, BCIG).

Luciferase is another exemplary enzyme. Substrates therefore typically are luciferins. Luciferase can be those from any bacterial or plant species and their corresponding substrate, such as click beetle luciferin, firefly luciferin, latia luciferin, bacterial luciferin, *Renilla* luciferin, coelenterazine luciferin, dinoflagellate luciferin and cypridina luciferin.

Body fluid samples for practicing the methods, include, but are not limited to, a body fluid that is selected from among blood, plasma, serum, lymph, ascetic fluid, cystic fluid, urine, nipple exudates, sweat, tears, saliva, mouth gargle, peritoneal fluid, cerebrospinal fluid (csf), synovial fluid, aqueous humour, vitreous humour, amniotic fluid, bile, cerumen (earwax), Cowper's fluid (pre-ejaculatory fluid), Chyle, Chyme, female ejaculate, interstitial fluid, lymph fluid, menses, breast milk, mucus, snot, phlegm, pleural fluid, pus, sebum, semen, vaginal lubrication, and feces. Exemplary of convenient samples are blood, plasma, serum and urine, such as blood, or such as urine.

The sample can be collected once or periodically or intermittently. It can be collected before treatment for comparison with a sample or samples subsequent to treatment. Exemplary time periods include, for example, collection of sample between or between about 12 hours to 1 month, 12 hours to 2 weeks, 12 hours to 7 days, 1 day to 7 days, 1 day to 5 days, 1 day to 3 days, 1 day to 2 days, 1 week to 4 weeks, 1 week to 3 weeks, 1 week to 2 weeks after treatment with the vector or biological therapy, or is collected on or on about 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days 21 days, 4 weeks, 5 weeks, 6 weeks, 7 weeks or 8 weeks after treatment with the vector or biological therapy or between or between about 12 hours to 1 month, 12 hours to 2 weeks, 12 hours to 7 days, 1 day to 7 days, 1 day to 5 days, 1 day to 3 days, 1 day to 2 days, 1 week to 4 weeks, 1 week to 3 weeks, 1 week to 2 weeks after treatment with the vector or biological therapy, or is collected on or on about 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 4 weeks, 5 weeks, 6 weeks, 7 weeks or 8 weeks after treatment with the vector or biological therapy.

The amount of sample or treated sample or purified protein from a sample and substrate can be empirically determined or is known. Exemplary ratios of substrate to sample include, but are not limited to, from or from about 1:1,000,000 to 1:100,000; 1:1,000,000 to 1:10,000; 1:1,000,000 to 1:1,000; 1:500,000 to 1:100,000; 1:500,000 to 1:50,000; 1:500,000 to 1:10,000; 1:100,000 to 10,000; 1:100,000 to 1:1,000; 1:100,000 to 1:500; 1:50,000 to 1:10,000; 1:50,000 to 1:1,000; 1:50,000 to 1:500; 1:10,000 to 1:1,000; 1:10,000 to 1:500; 1:10,000 to 1:100; 1:10,000 to 1:1; 1:1000 to 1:500; 1:1000 to 1:100; 1:1000 to 1:1; 1:500 to 1:100; 1:500 to 1:1, weight/volume (w/v); or is at least or at least about or is 1:1,000,000, 1:500,000, 1:250,000, 1:100,000, 1:75,000, 1:50,000, 1:25,000, 1:10,000, 1:5,000, 1:2,500, 1:1,000, 1:900, 1:800, 1:700, 1:600, 1:500, 1:400, 1:300, 1:200, 1:100, 1:50, 1:45, 1:40, 1:35, 1:30, 1:25, 1:20, 1:15, 1:10, 1:5, 1:4, 1:3, 1:2, 1:1 or less, weight to volume (w/v).

Substrate can be added to a sample in any suitable amount, such as, for example, at an amount less than 1 pg, or between or between about 1 pg to 1 mg, 1 pg to 1 μg, 1 pg to 1 ng, 1 pg to 500 pg, 50 pg to 1 mg, 50 pg to 1 μg, 50 pg to 1 ng, 50 pg to 500 pg, 250 pg to 1 μg, 250 pg to 1 ng, 250 pg to 750 pg, 500 pg to 1 mg, 500 pg to 1 μg, 500 pg to 1 ng, 1 ng to 1 mg, 1 ng to 500 μg, 1 ng to 1 μg, 1 ng to 500 ng, 250 ng to 1 mg, 250 ng to 500 μg, 250 ng to 250 μg, 250 ng to 1 μg, 250 ng to 750 ng, 500 ng to 1 mg, 500 ng to 500 μg, 500 ng to 1 μg, 1 μg to 1 mg, 1 μg to 500 μg, 1 μg to 250 μg, 1 μg to 100 μg, 1 μg to 50 μg, 1 μg to 10 μg, 10 μg to 1 mg, 10 μg to 500 μg, 10 μg to 250 μg, 10 μg to 100 μg, 10 μg to 50 μg, 25 μg to 500 μg, 25 μg to 250 μg, 25 μg to 100 μg, 50 μg to 1 mg, 50 μg to 500 μg, 50 μg to 250 μg, 50 μg to 100 μg, 100 μg to 1 mg, 100 μg to 500 μg, 100 μg to 300 μg, 300 μg to 700 μg, 300 μg to 500 μg, 500 μg to 1 mg; or is about or at least about or is 1 pg, 5 pg, 10 pg, 20 pg, 30 pg, 40 pg, 50 pg, 100 pg, 150 pg, 200 pg, 250 pg, 300 pg, 350 pg, 400 pg, 500 pg, 550 pg, 600 pg, 650 pg, 700 pg, 750 pg, 800 pg, 850 pg, 900 pg, 950 pg, 1 ng, 10 ng, 20 ng, 30 ng, 40 ng, 50 ng, 100 ng, 150 ng, 200 ng, 250 ng, 300 ng, 350 ng, 400 ng, 450 ng, 500 ng, 550 ng, 600 ng, 650 ng, 700 ng, 750 ng, 800 ng, 850 ng, 900 ng, 950 ng, 1 μg, 1.25 μg, 1.5 μg, 1.75 μg, 2 μg, 2.25 μg, 2.5 μg, 2.75 μg, 3 μg, 3.25 μg, 3.5 μg, 3.75 μg, 4 μg, 4.25 μg, 4.5 μg, 4.75 μg, 5 μg, 5.5 μg, 6 μg, 6.5 μg, 7 μg, 7.5 μg, 8 μg, 8.5 μg, 9 μg, 9.5 μg, 10 μg, 11 μg, 12 μg, 13 μg, 14 μg, 15 μg, 16 μg, 17 μg, 18 μg, 19 μg, 20 μg, 25 μg, 30 μg, 35 μg, 40 μg, 45 μg, 50 μg, 60 μg, 70 μg, 80 μg, 90 μg, 100

μg, 150 μg, 200 μg, 250 μg, 500 μg or 1 mg. Contacting a sample with a substrate can be effected for a suitable time, including incubation for less than a minute, from about 1 minute to 2 hours, 1 minute to 1 hour, 1 minute to 30 minutes, 1 minute to 15 minutes, 15 minutes to 2 hours, 15 minutes to 1 hour, 15 minutes to 45 minutes, 15 minutes to 30 minutes, 30 minutes to 6 hours, 30 minutes to 4 hours, 30 minutes to 2 hours, 30 minutes to 1 hour, 1 hour to 24 hours, 1 hour to 18 hours, 1 hour to 12 hours, 1 hour to 6 hours, 1 hour to 3 hours, 1 hour to 2 hours, 6 hours to 24 hours, 6 hours to 18 hours, 6 hours to 12 hours, 12 hours to 24 hours, 12 hours to 18 hours, or is at least or is about or is 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 12 hours, 18 hours or 24 hours prior to detection.

The methods herein can be employed for detecting a bacterial infection by obtaining a sample from a subject and adding a detectable substrate for beta-glucuronidase to a sample from a subject suspected of having an infection; and detecting beta-glucuronidase activity in the sample. Samples include urine, blood and serum. Infections include, for example, among sepsis, and a urinary tract infection. The substrates are any suitable substrates for such enzyme, including those listed above, such as, but not limited to fluorescein di-β-D-glucuronide (FDGlcU) and 4-methylumbelliferyl-β-D-glucuronide (4-MUG). Bacterial infections include, but are not limited to, those caused by *Escherichia, Shigella* and *Salmonella*, and any microorganism that expresses a beta-galactosidase. The methods can further include administering an antibiotic effective against such bacteria.

Similarly, method for detecting viral infection of a cell are provided. The cells include cells that occur in vivo and also in in vitro cultures. A sample from a tissue or body fluid of a host infected with the virus or from culture medium in which the cells are cultured is obtained that a product encoded by the virus, particularly a vaccinia virus, including any described herein, and any that encode reporters, including a beta-glucuronidase, as described herein, is detected. As noted the methods can be used to detect a tumor, particularly by administering a vaccinia virus, including any describe herein or known to those of skill in the art, obtaining a body fluid sample, and detecting beta-glucuronidase activity in the sample, wherein detection of activity indicates the presence of tumor cells in the subject.

Also provided herein is a method for monitoring oncolytic viral therapy that involves obtaining a sample from a subject treated with the therapy, wherein the subject had been treated with a virus that encodes beta-glucuronidase; and the sample is a body fluid or tissue sample and is not a tumor sample; and detecting beta-glucuronidase activity in the sample, wherein activity in the sample indicates that the therapeutic virus has colonized or is replicating in a tumor. In some examples, the nucleic acid encoding the beta-glucuronidase is not operatively linked to nucleic acid encoding a signal sequence for secretion. In other examples, nucleic acid encoding the beta-glucuronidase is operatively linked to nucleic acid encoding a signal sequence for secretion. In the provided method, sampling can be repeated periodically or intermittently following treatment(s).

The oncolytic virus used in the provided method can be selected from among an oncolytic poxvirus, adenovirus, reovirus, herpes virus, adeno-associated virus, lentivirus, retrovirus, rhabdovirus, papillomavirus, vesicular stomatitis virus, measles virus, Newcastle disease virus, picornavirus, sindbis virus, papillomavirus, parvovirus, coxsackievirus, influenza virus, mumps virus, poliovirus and semliki forest virus. In some examples, the virus is a poxvirus that is selected from among an orthopoxvirus, parapoxvirus, avipoxvirus, capripoxvirus, leporipoxvirus, suipoxvirus, molluscipoxvirus, yatapoxvirus, entomopoxvirus A, entomopoxvirus B and entomopoxvirus C. In an exemplary example, the virus is a poxvirus. The poxvirus used in the method can be a vaccinia virus that is an LIVP virus, clonal variant of a LIVP virus. In other examples, the vaccinia virus is a Lister strain virus that is LIVP or a clonal variant of LIVP. In an exemplary example of the method, the virus is GLV-1h68 or a derivative or modified form thereof. In further examples of the method, the virus has a sequence of nucleotides set forth in any of SEQ ID NOS:82-83 and 85-91, or a sequence of nucleotides that has at least 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to a sequence of nucleotides set forth in any of SEQ ID NOS: 82-83 and 85-91. In some examples, the virus is selected from among GLV-1h22, GLV-1i69, GLV-1h70, GLV-1h71, GLV-1h72, GLV-1h73, GLV-1h74, GLV-1h80, GLV-1h81, GLV-1h82, GLV-1h83, GLV-1h84, GLV-1h85, GLV-1h86, GLV-1j87, GLV-1j88, GLV-1j89, GLV-1h90, GLV-1h91, GLV-1h92, GLV-1h96, GLV-1h97, GLV-1h98, GLV-1h99, GLV-1h100, GLV-1h101, GLV-1h104, GLV-1h105, GLV-1h106, GLV-1h107, GLV-1h108, GLV-1h109, GLV-1h139, GLV-1h146, GLV-1h150, GLV-1h151, GLV-1h152 and GLV-1h153.

In the provided method, the biological therapeutic can be administered systemically. In other examples, administration of the biological therapeutic is effected topically, locally, enterally or parenterally, for example, administration is effected orally, epicutaneously, intranasally, by gastric feeding tube, duodenal feeding tube, or gastrostomy, rectally, intravenously, intraarterially, intramuscularly, intracardiacly, subcutaneously, by intraosseous infusion (into the bone marrow), intradermally, intraperitoneally, intrapleurally, transdermally, transmucosally, epidurally, intrathecally, intraventricularly or intratumorally.

In some examples of the provided method, the amount of virus administered is $1\times10^5$ or about $1\times10^5$ plaque forming units (PFU), $5\times10^5$ or about $5\times10^5$ PFU, $1\times10^6$ or about $1\times10^6$ PFU, $5\times10^6$ or about $5\times10^6$ PFU, $1\times10^7$ or about $1\times10^7$ PFU, $5\times10^7$ or about $5\times10^7$ PFU, $1\times10^8$ or about $1\times10^8$ PFU, $5\times10^8$ or about $5\times10^8$ PFU, $1\times10^9$ or about $1\times10^9$ PFU, $5\times10^9$ or about $5\times10^9$ PFU, $1\times10^{10}$ or about $1\times10^{10}$ PFU or $5\times10^{10}$ or about $5\times10^{10}$ PFU as total single dosage for an average human of 75 kg or adjusted for the weight and size and species of the subject. One of skill in the art can determine suitable dosage. Suitable dosages for a virus can be determined empirically.

In the methods herein, the β-glucuronidase can be a human or bacterial β-glucuronidase. In an exemplary embodiment, the β-glucuronidase has a sequence of amino acids set forth in SEQ ID NO:121 or an active portion thereof or a sequence having at least 85% sequence identity to a sequence of amino acids set forth in SEQ ID NO:121. In yet another exemplary embodiment, the β-glucuronidase has a sequence of amino acids set forth in SEQ ID NO:4 or an active portion thereof or a sequence having at least 85% sequence identity to a sequence of amino acids set forth in SEQ ID NO:4. Other β-glucuronidase enzymes include any having a sequence of amino acids set forth in any of SEQ ID NOS: 4, 114-121, 128, 130, 132, 134, 136, 138, 140, 142, 144 and 146, or an active portion thereof or a sequence having at least 85% sequence identity to a sequence of amino acids set forth in any of SEQ ID NOS: 4, 114-121, 128, 130, 132, 134, 136, 138, 140, 142, 144 and 146.

In some examples of the provided method, the substrate is selected from among fluorescein di-β-D-glucuronide (FDGlcU), 4-methylumbelliferyl-β-D-glucuronide (4-MUG), carboxyumbelliferyl β-D-glucuronide (CUGlcU), 5-(Pentafluorobenzoylamino)fluorescein di-β-D-glucuronide (PFB-FDGlcU), $C_{12}$-Fluorescein β-D-Glucuronidase, 5-bromo-4-chloro-3-indolyl β-D-glucuronide (X-GlcU or BCIG), p-nitrophenyl-β-D-glucuronide, Red-β-D-GlcU,CHA (Magenta-b-D-GlcA; 5-bromo-6-chloro-3-indolyl-b-D-glucuronide, cyclohexylammonium salt), Rose-β-D-GlcU,CHA (Salmon-β-D-GlcUA; 5-bromo-6-chloro-3-indolyl-β-D-glucuronide, cyclohexylammonium salt), phenyl-β-D-glucuronide, and suitable salts thereof. In an exemplary embodiment, the substrate is selected from among fluorescein di-β-D-glucuronide (FDGlcU) and 4-methylumbelliferyl-β-D-glucuronide (4-MUG).

Body fluid samples for practicing the methods, include, but are not limited to, blood, plasma, serum, lymph, ascetic fluid, cystic fluid, urine, nipple exudates, sweat, tears, saliva, mouth gargle, peritoneal fluid, cerebrospinal fluid (csf), synovial fluid, aqueous humour, vitreous humour, amniotic fluid, bile, cerumen (earwax), Cowper's fluid (pre-ejaculatory fluid), Chyle, Chyme, female ejaculate, interstitial fluid, lymph fluid, menses, breast milk, mucus, snot, phlegm, pleural fluid, pus, sebum, semen, vaginal lubrication, and feces. In some examples, the sample is blood, plasma, serum or urine. In an exemplary embodiment, the sample is serum.

Subjects include any subject, including but not limited to any animal. The animals include humans, veterinary animals, pets, farm animals, animal models. Included are human, cats, dogs, frogs, ferrets, gorillas, chimpanzees, gorillas, birds, lions, tigers, cows, rodents, goats, pigs, chickens, horses, zebras, dolphins and whales.

The sample can be collected once or periodically or intermittently. It can be collected before treatment for comparison with a sample or samples subsequent to treatment. Exemplary time periods include, for example, collection of sample between or between about 12 hours to 1 month, 12 hours to 2 weeks, 12 hours to 7 days, 1 day to 7 days, 1 day to 5 days, 1 day to 3 days, 1 day to 2 days, 1 week to 4 weeks, 1 week to 3 weeks, 1 week to 2 weeks after treatment with the vector or biological therapy, or is collected on or on about 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 4 weeks, 5 weeks, 6 weeks, 7 weeks or 8 weeks after treatment with the virus. In other examples, one or more samples are collected between or between about 12 hours to 1 month, 12 hours to 2 weeks, 12 hours to 7 days, 1 day to 7 days, 1 day to 5 days, 1 day to 3 days, 1 day to 2 days, 1 week to 4 weeks, 1 week to 3 weeks, 1 week to 2 weeks after treatment with the vector or biological therapy, or is collected on or on about 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 4 weeks, 5 weeks, 6 weeks, 7 weeks or 8 weeks after treatment with the virus.

The amount of sample or treated sample or purified protein from a sample and substrate can be empirically determined or is known. Exemplary ratios of substrate to sample include, but are not limited to, from or from about 1:1,000,000 to 1:100,000; 1:1,000,000 to 1:10,000; 1:1,000,000 to 1:1,000; 1:500,000 to 1:100,000; 1:500,000 to 1:50,000; 1:500,000 to 1:10,000; 1:100,000 to 10,000; 1:100,000 to 1:1,000; 1:100,000 to 1:500; 1:50,000 to 1:10,000; 1:50,000 to 1:1,000; 1:50,000 to 1:500; 1:10,000 to 1:1,000; 1:10,000 to 1:500; 1:10,000 to 1:100; 1:10,000 to 1:1; 1:1000 to 1:500; 1:1000 to 1:100; 1:1000 to 1:1; 1:500 to 1:100; 1:500 to 1:1, weight/volume (w/v); or is at least or at least about or is 1:1,000,000, 1:500,000, 1:250,000, 1:100,000, 1:75,000, 1:50,000, 1:25,000, 1:10,000, 1:5,000, 1:2,500, 1:1,000, 1:900, 1:800, 1:700, 1:600, 1:500, 1:400, 1:300, 1:200, 1:100, 1:50, 1:45, 1:40, 1:35, 1:30, 1:25, 1:20, 1:15, 1:10, 1:5, 1:4, 1:3, 1:2, 1:1 or less, weight to volume (w/v). Substrate can be added to a sample in any suitable amount, such as, for example, at an amount less than 1 pg, or between or between about 1 pg to 1 mg, 1 pg to 1 µg, 1 pg to 1 ng, 1 pg to 500 pg, 50 pg to 1 mg, 50 pg to 1 µg, 50 pg to 1 ng, 50 pg to 500 pg, 250 pg to 1 µg, 250 pg to 1 ng, 250 pg to 750 pg, 500 pg to 1 mg, 500 pg to 1 µg, 500 pg to 1 ng, 1 ng to 1 mg, 1 ng to 500 µg, 1 ng to 1 µg, 1 ng to 500 ng, 250 ng to 1 mg, 250 ng to 500 µg, 250 ng to 250 µg, 250 ng to 1 µg, 250 ng to 750 ng, 500 ng to 1 mg, 500 ng to 500 µg, 500 ng to 1 µg, 1 µg to 1 mg, 1 µg to 500 µg, 1 µg to 250 µg, 1 µg to 100 µg, 1 µg to 50 µg, 1 µg to 10 µg, 10 µg to 1 mg, 10 µg to 500 µg, 10 µg to 250 µg, 10 µg to 100 µg, 10 µg to 50 µg, 25 µg to 500 µg, 25 µg to 250 µg, 25 µg to 100 µg, 50 µg to 1 mg, 50 µg to 500 µg, 50 µg to 250 µg, 50 µg to 100 µg, 100 µg to 1 mg, 100 µg to 500 µg, 100 µg to 300 µg, 300 µg to 700 µg, 300 µg to 500 µg, 500 µg to 1 mg; or is about or at least about or is 1 pg, 5 pg, 10 pg, 20 pg, 30 pg, 40 pg, 50 pg, 100 pg, 150 pg, 200 pg, 250 pg, 300 pg, 350 pg, 400 pg, 500 pg, 550 pg, 600 pg, 650 pg, 700 pg, 750 pg, 800 pg, 850 pg, 900 pg, 950 pg, 1 ng, 10 ng, 20 ng, 30 ng, 40 ng, 50 ng, 100 ng, 150 ng, 200 ng, 250 ng, 300 ng, 350 ng, 400 ng, 450 ng, 500 ng, 550 ng, 600 ng, 650 ng, 700 ng, 750 ng, 800 ng, 850 ng, 900 ng, 950 ng, 1 µg, 1.25 µg, 1.5 µg, 1.75 µg, 2 µg, 2.25 µg, 2.5 µg, 2.75 µg, 3 µg, 3.25 µg, 3.5 µg, 3.75 µg, 4 µg, 4.25 µg, 4.5 µg, 4.75 µg, 5 µg, 5.5 µg, 6 µg, 6.5 µg, 7 µg, 7.5 µg, 8 µg, 8.5 µg, 9 µg, 9.5 µg, 10 µg, 11 µg, 12 µg, 13 µg, 14 µg, 15 µg, 16 µg, 17 µg, 18 µg, 19 µg, 20 µg, 25 µg, 30 µg, 35 µg, 40 µg, 45 µg, 50 µg, 60 µg, 70 µg, 80 µg, 90 µg, 100 µg, 150 µg, 200 µg, 250 µg, 500 µg or 1 mg. Contacting a sample with a substrate can be effected for a suitable time, including incubation for less than a minute, from or from about 1 minute to 2 hours, 1 minute to 1 hour, 1 minute to 30 minutes, 1 minute to 15 minutes, 15 minutes to 2 hours, 15 minutes to 1 hour, 15 minutes to 45 minutes, 15 minutes to 30 minutes, 30 minutes to 6 hours, 30 minutes to 4 hours, 30 minutes to 2 hours, 30 minutes to 1 hour, 1 hour to 24 hours, 1 hour to 18 hours, 1 hour to 12 hours, 1 hour to 6 hours, 1 hour to 3 hours, 1 hour to 2 hours, 6 hours to 24 hours, 6 hours to 18 hours, 6 hours to 12 hours, 12 hours to 24 hours, 12 hours to 18 hours, or is at least or is about or is 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 12 hours, 18 hours or 24 hours prior to detection. For example, the sample and substrate are incubated for at least or about at least or 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes or 1 hour prior to detection.

BRIEF DESCRIPTION OF THE FIGURES

FIG. 4A. Tumor bearing mice were mock injected (n=2) or injected with GLV-1h68 (n=6) and rVACV-GusA$^-$ (n=6) respectively. Seven days later 5 µl serum was co-incubated for 1 h at 37° C. with 4-MUG and FDGlcU respectively and subsequently specific fluorescence was determined. FIG. 4B. Retrospective serum analysis. Serum samples (n=99) from different tumor xenograft models (GI-101A, A549, DU-145, PANC-1, HT-29) were retrospectively tested. Samples were derived from mock (n=33) injected mice or mice treated for different periods of time (7 to 53 days) with several GusA-positive (n=53) or -negative (n=13) rVACV. * indicates p<0.03; *** indicates p<0.001.

DETAILED DESCRIPTION

Figure 1:
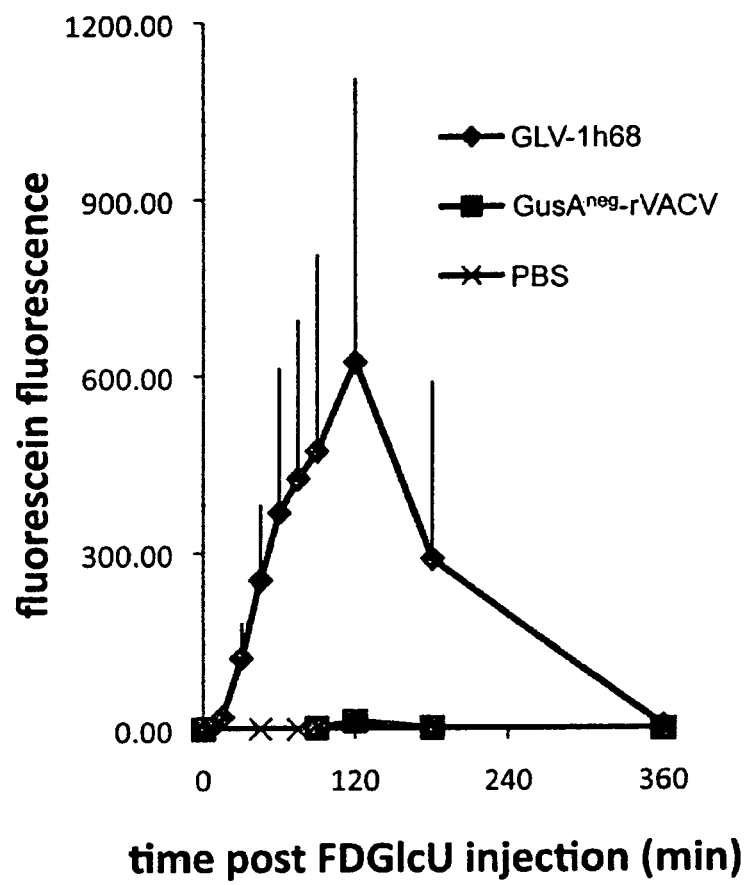
FIG. 1. Fluorogenic compound activation in rVACV-colonized tumors. Tumor specific fluorescence over time post FDGlcU-injection (n=4; average plus standard deviation is shown).

Outline
A. Definitions
B. Overview of Method
  1. Biological Therapies
    a. Oncolytic Viral Therapy
    b. other viruses
  2. Beta-glucuronidases as reporter proteins
  3. Method
C. Method for Detecting Replication or Colonization of a Biological Therapeutic
  1. Biological Therapeutics
    a. Viruses
      i. Poxviruses
        (1) Vaccinia Viruses
        (2) Modified Vaccinia Viruses
        (3) Exemplary Modified Vaccinia Viruses
      ii. Other Cytoplasmic Viruses
      iii. Adenovirus, Herpes, Retroviruses
    b. Bacteria
      i. *E. coli* strain Nissle 1917
      ii. Other bacteria
    c. Other Therapies
      i. Gene Therapy
      ii. Cell Therapy
      iii. Immunotherapy
  2. Reporters Proteins
    a. Reporter Enzymes
      i. β-glucuronidases
      ii. β-galactosidases
      iii. Luciferases
      iv. Chloramphenicol Acetyltransferases
      v. Alkaline phosphatases
    b. Reporter Enzyme Substrates
      i. β-glucuronidase substrates
      ii. β-galactosidase substrates
      iii. Luciferase substrates
      iv. Chloramphenicol Acetyltransferase substrates
      v. Alkaline phosphatase substrates
  3. Sample
  4. Addition of Reporter Protein Substrates
  5. Incubation of the Sample and the Reporter Protein Substrate
  6. Detection of Activated Substrate or Signal
D. Methods of Making Biological Therapeutics encoding an Reporter Protein
  1. Vectors
  2. Viruses
    a. Genetic Modifications
    b. Control of heterologous gene expression
  3. Bacteria
E. Methods for detecting and monitoring therapy
F. Examples
A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, a sample from a locus other than a target of the biological therapy, means that the sample is taken from a cell other than from the target of the biological therapy. For example, if the therapy treats tumors, then the sample is not a sample of the tumor tissue, but is obtained from another locus. Typically the other locus is a body fluid, but it can include tissue samples. The non-target sample, can include tumor cells, but, if it does, the sample or results are treated or tested so that tumor or target tissue or cells or biological therapeutic are not present or the results are normalized to eliminate any contribution from tumor or target cells or tissue or biological therapeutic. For purposes herein, the assessed material is distinct from the tumor or target cells or tissue or biological therapeutic and measures or detects shed proteins that are encoded by the biological therapeutic. For gene therapy and other therapies in which a particular product is introduced, the tested product is not the gene therapy product, but is another product encoded by the biological therapeutic.

As used herein, shed proteins means that the encoded proteins are not actively secreted, but are produced by the biological therapeutic and appear in biological tissues and fluids because of replication and colonization by the biological therapeutic. In particular, in embodiments in which the biological therapeutic is an oncolytic virus, such as a vaccinia virus, the encoded protein is shed by virtue of the fact that the virus replicates in tumor cells and lyses such cells, which releases the proteins.

As used herein, a target of the therapeutic refers to the intended locus of treatment, e.g., the target locus. If the therapeutic is an oncolytic virus, the target is/are tumor cells or other immunoprivileged cells. If the therapy is gene therapy to provide a gene product that is systemically expressed, then the target is systemic expression, and a sample from a locus other than the target means that a sample is treated or detection is effected or normalized to eliminate any contribution from the introduced gene therapy biological therapeutic or an encoded product other than gene therapy product is detected.

As used herein, a reporter gene refers to nucleic acid contained within a biological therapeutic that encodes a reporter protein that is to be detected. The reporter gene does not encode a therapeutic product encoded by the biological therapeutic, but encodes some other endogenous or heterologous product that is to be detected, either directly or indirectly. Typically, the reporter gene is heterologous to the biological therapeutic and encodes a detectable protein or encodes a protein that induces or produces a detectable signal. In embodiments in which the encoded reporter protein is shed, the reporter gene is not operatively linked to nucleic acid that directs secretion of the product. In embodiments, such as embodiments in which the gene encodes a glucuronidase, it can be secreted.

As used herein, a reporter protein is a protein encoded by a reporter gene. The reporter protein is not a therapeutic protein encoded by the biological therapeutic, but is some other endogenous or heterologous protein that is to be detected, either directly or indirectly. Typically, the reporter protein is heterologous to the biological therapeutic and is detectable or is a protein that induces or produces a detectable signal. A reporter protein can be shed, that is, the reporter protein is not secreted by the biological therapeutic. In embodiments where the reporter protein is a beta-glucuronidase, the reporter protein can be shed or secreted by the biological therapeutic. A reporter enzyme or enzymatic reporter protein refers to a reporter protein that is an enzyme. Detection of the reporter protein, including reporter enzyme, or signal induced by a reporter protein is indicative of gene expression of a gene contained with the biological therapeutic, such as the vector or virus.

As used herein, a sample is a body fluid or tissue sample from a subject that has been or will be treated with a biological therapeutic. The sample is tested to detect a product, such as a reporter protein, that has been expressed and shed or, in some instances, such as where the reporter is beta-glucuronidase and the biological therapeutic is a vaccinia virus, secreted or shed, by the biological therapeutic. The results are compared to an appropriate control and/or corrected, so that only the contribution of the particular reporter protein is determined. These results assess the colonization or replication of the biological therapeutic in a target cell or cells or target tissue(s). Examples of body fluids include urine, blood, plasma, serum, saliva, semen, stool, sputum, cerebral spinal fluid, tears, mucus, amniotic fluid or the like.

As used herein, biological therapy refers to any therapy that involves administration of a biological agent or biological therapeutic, such as a virus, a viral vector and a cell, including stem cells and cells used for adoptive immunotherapy protocols, for purposes of treatment and/or diagnostics. Hence included are therapies in which mammalian viruses for gene therapy are administered, therapies in which eukaryotic or prokaryotic organisms, such as cells, viruses and bacteria, are administered for treatment or diagnosis, and oncolytic viral therapies, particularly those in which viruses that accumulate or that are modified to accumulate in immunoprivileged cells, such as tumor cells and inflamed tissues, are administered. The administered cells and viruses and bacteria can be modified by inclusion of heterologous nucleic acid that encodes therapeutic products and/or reporters. The methods herein assess expression of a product or a signal produced by a product encoded by the biological therapy in a sample, typically a body fluid sample, obtained from a subject to whom such virus, cell and/or bacterium is administered. The target of the therapy, such as a tumor tissue or other tissue, is different from the locus from which the sample is obtained.

As used herein, replication of a biological therapeutic in a host or subject refers to replication of a virus, bacteria, or a genome thereof, in a host or subject to whom such therapeutic is administered. For therapies such as oncolytic viral therapies and gene therapies requiring sustained expression of a product or cell therapies, treatment requires replication of the genome of the therapeutic. For the detection methods herein, replication is indicative that the therapy is initiated. Colonization generally refers to establishment of a biological therapeutic in a host. Biological therapies such as cell therapies in which cells are transplanted requires that an organ or tissue is colonized by the administered cells to produce a product. Colonization and replication are not mutually exclusive.

As used herein, circulating tumor cell or CTC refers to a tumor cell derived from a primary cancer site that has detached from the primary tumor mass. CTCs includes cancer cells, malignant tumor cells, benign tumor cells and cancer stem cells. CTCs include any cancer cell or cluster of cancer cells that is found in a sample obtained from a subject. CTCs are often epithelial cells shed from solid tumors. CTCs also can be mesothelial cells from carcinomas or melanocytes from melanomas. A CTC is typically a cell originating from a primary tumor, but also can be a cell shed from a metastatic tumor (e.g., a secondary or tertiary tumor). As used herein, the term "CTC" is intended to encompass any tumor cell that has detached from a tumor. Thus, as used herein, a CTC encompasses tumor cells found in circulation, such as in the blood or lymph, or in other fluid samples, such as, but not limited to, pleural fluid, peritoneal fluid, central spinal fluid, abdominal fluid, pancreatic fluid, cerebrospinal fluid, brain fluid, ascites, urine, saliva, bronchial lavage, bile, sweat, tears, ear flow, sputum, semen, vaginal flow, milk, amniotic fluid, and secretions of respiratory, intestinal or genitourinary tract. The term CTC as used herein also includes disseminated tumor cells (DTCs) found in the bone marrow.

As used herein the term "vaccinia virus" or "VACV" denotes a large, complex, enveloped virus belonging to the poxvirus family. It has a linear, double-stranded DNA genome approximately 190 kbp in length, and which encodes approximately 200 proteins. Vaccinia virus strains include, but are not limited to, strains of, derived from, or modified forms of Western Reserve (WR), Copenhagen, Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, New York City Board of Health vaccinia virus strains.

As used herein, Lister Strain of the Institute of Viral Preparations (LIVP) or LIVP virus strain refers to a virus strain that is the attenuated Lister strain (ATCC Catalog No. VR-1549) that was produced by adaption to calf skin at the Institute of Viral Preparations, Moscow, Russia (Al'tshtein et al. (1985)

*Dokl. Akad. Nauk USSR* 285:696-699). The LIVP strain can be obtained, for example, from the Institute of Viral Preparations, Moscow, Russia (see. e.g., Kutinova et al. (1995) Vaccine 13:487-493); the Microorganism Collection of FSRI SRC VB Vector (Kozlova et al. (2010) Environ. Sci. Technol. 44:5121-5126); or can be obtained from the Moscow Ivanovsky Institute of Virology (C0355 K0602; Agranovski et al. (2006) Atmospheric Environment 40:3924-3929). It also is well known to those of skill in the art; it was the vaccine strain used for vaccination in the USSR and throughout Asia and India. The strain now is used by researchers and is well known (see e.g., Altshteyn et al. (1985) *Dokl. Akad. Nauk USSR* 285:696-699; Kutinova et al. (1994) *Arch. Virol.* 134: 1-9; Kutinova et al. (1995) *Vaccine* 13:487-493; Shchelkunov et al. (1993) *Virus Research* 28:273-283; Sroller et al. (1998) *Archives Virology* 143:1311-1320; Zinoviev et al., (1994) *Gene* 147:209-214; and Chkheidze et al. (1993) *FEBS* 336: 340-342). Among the LIVP strains is one that contains a genome having a sequence of nucleotides set forth in SEQ ID NO:91, or a sequence that is at least or at least about 99% identical to the sequence of nucleotides set forth in SEQ ID NO:91.

As used herein, an LIVP clonal strain, LIVP clonal variant or LIVP clonal isolate refers to a virus that is derived from the LIVP virus strain by plaque isolation, or other method in which a single clone is propagated, and that has a genome that is homogenous in sequence. Hence, an LIVP clonal strain includes a virus whose genome is present in a virus preparation propagated from LIVP. An LIVP clonal strain does not include a recombinant LIVP virus that is genetically engineered by recombinant means using recombinant DNA methods to introduce heterologous nucleic acid. In particular, an LIVP clonal strain has a genome that does not contain heterologous nucleic acid that contains an open reading frame encoding a heterologous protein. For example, an LIVP clonal strain has a genome that does not contain non-viral heterologous nucleic acid that contains an open reading frame encoding a non-viral heterologous protein. As described herein, however, it is understood that any of the LIVP clonal strains provided herein can be modified in its genome by recombinant means to generate a recombinant virus. For example, an LIVP clonal strain can be modified to generate a recombinant LIVP virus that contains insertion of nucleotides that contain an open reading frame encoding a heterologous protein. Among the LIVP clonal isolates are those having a genome having a sequence of amino acids set forth in SEQ ID NOS:82-83 and 85-89, or sequences that are at least or at least about 99% identical to the sequences of nucleotides set forth in SEQ ID NOS:82-83 and 85-89.

As used herein, a modified LIVP virus strain refers to an LIVP virus that has a genome that is not contained in LIVP, but is a virus that is produced by modification of a genome of a strain derived from LIVP. Typically, the genome of the virus is modified by substitution (replacement), insertion (addition) or deletion (truncation) of nucleotides. Modifications can be made using any method known to one of skill in the art such as genetic engineering and recombinant DNA methods. Hence, a modified virus is a virus that is altered in its genome compared to the genome of a parental virus. Exemplary modified viruses have one or more heterologous nucleic acid sequences inserted into the genome of the virus. Typically, the heterologous nucleic acid contains an open reading frame encoding a heterologous protein. For example, modified viruses herein can contain one or more heterologous nucleic acid sequences in the form of a gene expression cassette for the expression of a heterologous gene.

As used herein a "gene expression cassette" or "expression cassette" is a nucleic acid construct, containing nucleic acid elements that are capable of effecting expression of a gene in hosts that are compatible with such sequences. Expression cassettes include at least promoters and optionally, transcription termination signals. Typically, the expression cassette includes a nucleic acid to be transcribed operably linked to a promoter. Expression cassettes can contain genes that encode, for example, a therapeutic gene product, or a detectable protein or a selectable marker gene.

As used herein, LIVP GLV-1h68 is an LIVP virus that contains ruc-gfp (a luciferase and green fluorescent protein fusion gene (see e.g. U.S. Pat. No. 5,976,796), beta-galactosidase (lacZ) and beta-glucuronidase (gusA) reporter genes inserted into the F14.5L, J2R (thymidine kinase) and A56R (hemagglutinin) loci, respectively. The genome of GLV-1h68 has a sequence of nucleotides set forth in SEQ ID NO:90, or a sequence of nucleotides that has at least 99% sequence identity to the sequence of nucleotides set forth in SEQ ID NO:90.

As used herein, a virus preparation, for example an LIVP virus preparation, refers to a virus composition obtained by propagation of a virus strain, for example an LIVP virus strain, an LIVP clonal strain or a modified or recombinant virus strain, in vivo or in vitro in a culture system. For example, an LIVP virus preparation refers to a viral composition obtained by propagation of a virus strain in host cells, typically upon purification from the culture system using standard methods known in the art. A virus preparation generally is made up of a number of virus particles or virions. If desired, the number of virus particles in the sample or preparation can be determined using a plaque assay to calculate the number of plaque forming units per sample unit volume (pfu/mL), assuming that each plaque formed is representative of one infective virus particle. Each virus particle or virion in a preparation can have the same genomic sequence compared to other virus particles (i.e. the preparation is homogenous in sequence) or can have different genomic sequences (i.e. the preparation is heterogenous in sequence). It is understood to those of skill in the art that, in the absence of clonal isolation, heterogeneity or diversity in the genome of a virus can occur as the virus reproduces, such as by homologous recombination events that occur in the natural selection processes of virus strains (Plotkin & Orenstein (eds) "Recombinant Vaccinia Virus Vaccines" in Vaccines, $3^{rd}$ edition (1999)).

As used herein, a virus mixture is a virus preparation that contains a number of virus particles that differ in their genomic sequences. The virus mixture can be obtained by infecting a culture system, for example host cells, with two or more different virus strains, or one virus strain and genomic DNA or cloned DNA, followed by propagation and purification of the resulting virus. For purposes herein, an LIVP virus preparation can include a virus mixture obtained by propagation of cells infected with an LIVP strain and another virus, genomic DNA or cloned DNA, followed by isolation of a virus preparation from the culture, where the preparation contains progeny viruses produced by the infection. For example, the other virus strain can be poxvirus, such as avipox virus, myxoma virus or other vaccinia virus; a herpesvirus such as herpes simplex virus (HSV), cytomegalovirus (CMV), Epstein-Barr virus (EBV), hepadnaviruses (e.g., hepatitis B virus), polyoma viruses, papillomaviruses, adenoviruses and adeno-associated viruses; and single-stranded DNA viruses, such as parvoviruses. The other virus can be an attenuated virus, oncolytic virus or other virus with known anti-tumor activity and/or moderate to mild toxicity.

As used herein, "virus" refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, sindbis virus, papillomavirus, parvovirus, reovirus, coxsackievirus, influenza virus, mumps virus, poliovirus, and semliki forest virus.

As used herein, oncolytic viruses refer to viruses that replicate selectively in tumor cells in tumorous subjects. Some oncolytic viruses can kill a tumor cell following infection of the tumor cell. For example, an oncolytic virus can cause death of the tumor cell by lysing the tumor cell or inducing cell death of the tumor cell.

As used herein, an "attenuated LIVP virus" with reference to LIVP refers to a virus that exhibits reduced or less virulence, toxicity or pathogenicity compared to LIVP.

As used herein, to attenuate toxicity of a bacterium means to reduce or eliminate deleterious or toxic effects to a host upon administration of the bacterium compared to an unattenuated bacterium. As used herein, a bacterium with low toxicity, means that upon administration, the bacterium does not accumulate in organs and tissues in the host to an extent that results in damage or harm to organs, or that impacts survival of the host to a greater extent than the disease being treated does.

As used herein, an attenuated, attenuated pathogenic or non-pathogenic bacterium refers to a bacterium that exhibits reduced or less virulence, toxicity or pathogenicity compared to a non-attenuated or pathogenic bacterium.

As used herein, accumulation of bacteria in a targeted tissue refers to the distribution of the bacteria throughout the organism after a time period long enough for the microbes to infect the host's organs or tissues. As one skilled in the art will recognize, the time period for infection of a microbe will vary depending on the microbe, the targeted organ(s) or tissue(s), the immunocompetence of the host, and dosage. Generally, accumulation can be determined at time point from about less than 1 day, about 1 day to about 1 week, about 1 week to about 2, 3 or 4 weeks, about 1 month to about 2, 3, 4, 5, 6 months or longer after infection with the microbes. For purposes herein, the bacteria preferentially accumulate in the target tissue, such as a tumor, or site of cellular proliferation, but are cleared from other tissues and organs in the host to the extent that toxicity of the bacteria is mild or tolerable and at most not fatal. As used herein, preferential accumulation refers to accumulation of bacteria at a first location at a higher level than accumulation at a second location. Thus, bacteria that preferentially accumulates in immunoprivileged tissue such as tumor relative to normal tissues or organs refers to bacteria that accumulate in immunoprivileged tissue, such as tumor, at a higher level (concentration) than the bacteria accumulate in normal tissues or organs.

As used herein, "commensal" when used in reference to an association between two organisms, is a particular association in which one member of the association benefits from the association while the other member is essentially unaffected. In a commensal association of organisms, none of the members of the association is significantly harmed by the presence of the other member. Two organisms can form a commensal association under particular, but not necessarily all, conditions. In such cases, as long as an organism is capable of forming a commensal association with the other organism under at least one set of conditions, the organism is considered to be one that can form a commensal association with the other organism.

As used herein, "mutual" when used in reference to an association between two or more organisms, is a particular association which is advantageous to both members of the association. In a mutual association of organisms, none of the members of the association is significantly harmed by the presence of the other member. Two organisms can form a mutual association under particular, but not necessarily all, conditions. In such cases, as long as an organism is capable of forming a mutual association with the other organism under at least one set of conditions, the organism is considered to be one that can form a mutual association with the other organism.

As used herein, a probiotic bacterium refers to a bacterium that confers a benefit to a host in which it can occur. The benefit can be, for example, an overall health benefit to the host, such as preventing, maintaining remission of, preventing recurrence of, reversing or reducing the symptoms or detrimental effects of a disorder or disease of the host. Such disorders/diseases include, but are not limited to, infectious diseases, inflammation, diarrhea (e.g., antibiotic-induced diarrhea, infectious diarrhea and traveler's diarrhea), inflammatory bowel disease, Crohn's disease, pouchitis and colitis. The benefit conferred by a probiotic bacterium can be stabilization of the host microbiota or microecology, for example, by improving the microbial balance of the indigenous microflora (Kruis W. (2004) *Pharmacol. Ther.* 20 (Suppl 4): 75-78). Probiotic bacteria can exert their effects in a number of ways. For example, probiotic bacteria can interfere with harmful properties of other pathogenic bacteria that can occur through the production of antimicrobial substances by the probiotic bacteria and interference with bacterial attachment/penetration to/into host cells. A probiotic bacterium also can stimulate a host to produce antimicrobial molecules, alter a host's immune response, stimulate mucosal barrier function or alter immunoregulation, such as by decreasing pro-inflammatory molecules and promoting protective molecules (Sartor RB. (2005) *Curr. Opin. Gastroenterol.* 21(1): 44-50). Exemplary probiotic bacteria include, but are not limited to, *E. coli* strain Nissle 1917 (O6:K5:H1; Mutaflor; Ardeypharm GmbH, Germany; Schultz et al. *J. Microbiol. Methods* 61(3): 389-398 (2005)). *E. coli* strain Nissle 1917 lacks defined virulence factors such as alpha-hemolysin, other toxins, and mannose-resistant hemagglutinating adhesins (Blum et al. *Infection*. 23(4):234-236 (1996)), P-fimbrial adhesins, and the semirough lipopolysaccharide phenotype and expresses fitness factors such as microcins, ferritins, six different iron uptake systems, adhesins, and proteases, which support its survival and successful colonization of the human gut (Grozdanov et al. (2004) *J Bacteriol.* 186(16): 5432-5441). *E. coli* Nissle 1917 interferes with bacterial invasion of other bacteria cells via a secreted component (Altenhoefer et al. (2004) *FEMS Immunol. Med. Microbiol.* 40(3): 223-9). *E. coli* Nissle 1917 can have plasmids (Mutaflor O6:K5:H1, DSM 6601 by Medipharm, Kågeröd, Sweden) or no plasmids (i.e. can be cured of plasmids).

As used herein, "toxicity" (also referred to as virulence or pathogenicity herein) with reference to a virus refers to the deleterious or toxic effects to a host upon administration of the virus. For an oncolytic virus, such as LIVP, the toxicity of a virus is associated with its accumulation in non-tumorous organs or tissues, which can impact the survival of the host or result in deleterious or toxic effects. Toxicity can be measured by assessing one or more parameters indicative of toxicity. These include accumulation in non-tumorous tissues and effects on viability or health of the subject to whom it has been administered, such as effects on weight.

As used herein, a "parameter indicative of toxicity" refers to a property mediated by a virus that is associated with its toxicity, virulence or pathogenicity. Parameters indicative of toxicity generally are assessed in vivo upon administration to a subject. Exemplary parameters indicative of toxicity include, but are not limited to, decreased survival of the subject, decreased body weight, fever, rash, allergy, fatigue, abdominal pain, induction of an immune response in the subject and pock formation. Assays or measures that assess any of the above parameters or other toxic properties known to one of skill in the art are described herein or are known to one of skill in the art. Hence, a virus that mediates any one or more of the above activities or properties in a host exhibits some degree of toxicity.

As used herein, "reduced toxicity" means that the toxic or deleterious effects upon administration of the virus to a host are attenuated or lessened compared to a host not treated with the virus or compared to a host that is administered with another reference or control virus. For purposes herein, exemplary of a reference or control virus is the LIVP virus designated GLV-1h68. Whether toxicity is reduced or lessened can be determined by assessing the effect of a virus and, if necessary, a control or reference virus, on a parameter indicative of toxicity. It is understood that when comparing the activity of two or more different viruses, the amount of virus (e.g. pfu) used in an in vitro assay or administered in vivo is the same or similar and the conditions (e.g. in vivo dosage regime) of the in vitro assay or in vivo assessment are the same or similar. For example, when comparing effects upon in vivo administration of a virus and a control or reference virus the subjects are the same species, size, gender and the virus is administered in the same or similar amount under the same or similar dosage regime. In particular, a virus with reduced toxicity can mean that upon administration of the virus to a host, such as for the treatment of a disease, the virus does not accumulate in non-tumorous organs and tissues in the host to an extent that results in damage or harm to the host, or that impacts survival of the host to a greater extent than the disease being treated does or to a greater extent than a control or reference virus does. For example, a virus with reduced toxicity includes a virus that does not result in death of the subject over the course of treatment.

As used herein, accumulation of a virus in a particular tissue refers to the distribution of the virus in particular tissues of a host organism after a time period following administration of the virus to the host, long enough for the virus to infect the host's organs or tissues. As one skilled in the art will recognize, the time period for infection of a virus will vary depending on the virus, the organ(s) or tissue(s), the immunocompetence of the host and dosage of the virus. Generally, accumulation can be determined at time points from about less than 1 day, about 1 day to about 2, 3, 4, 5, 6 or 7 days, about 1 week to about 2, 3 or 4 weeks, about 1 month to about 2, 3, 4, 5, 6 months or longer after infection with the virus. For purposes herein, the viruses preferentially accumulate in immunoprivileged tissue, such as inflamed tissue or tumor tissue, but are cleared from other tissues and organs, such as non-tumor tissues, in the host to the extent that toxicity of the virus is mild or tolerable and at most, not fatal.

As used herein, "preferential accumulation" refers to accumulation of a virus at a first location at a higher level than accumulation at a second location (i.e., the concentration of viral particles, or titer, at the first location is higher than the concentration of viral particles at the second location). Thus, a virus that preferentially accumulates in immunoprivileged tissue (tissue that is sheltered from the immune system), such as inflamed tissue, and tumor tissue, relative to normal tissues or organs, refers to a virus that accumulates in immunoprivileged tissue, such as tumor, at a higher level (i.e., concentration or viral titer) than the virus accumulates in normal tissues or organs.

As used herein, "anti-tumor activity" or "anti-tumorigenic" refers to virus strains that prevent or inhibit the formation or growth of tumors in vitro or in vivo in a subject. Anti-tumor activity can be determined by assessing a parameter or parameters indicative of anti-tumor activity.

As used herein, a "parameter indicative of anti-tumor activity or anti-tumorigenic activity" refers to a property mediated by a virus that is associated with anti-tumor activity. Parameters indicative of anti-tumor activity can be assessed in vitro or in vivo upon administration to a subject. Exemplary parameters indicative of anti-tumor activity include, but are not limited to, infectivity of tumor cells, accumulation of virus in tumor tissues, viral nucleic acid replication in tumor cells, virus production in tumor cells, viral gene expression in tumor cells, cytotoxicity of tumor cells, tumor cell selectivity, tumor cell type selectivity, decreased tumor size, increased tumor volume, decreased tumor weight, and initiation of specific and nonspecific anti-tumor immune responses. Assays that assess any of the above parameters or other anti-tumorigenic properties are known to one of skill in the art. Hence, a virus that exhibits any one or more of the above activities or properties exhibits anti-tumor activity.

As used herein, "greater" or "improved" activity with reference to anti-tumor activity or anti-tumorigenicity means that a virus strain is capable of preventing or inhibiting the formation or growth of tumors in vitro or in vivo in a subject to a greater extent than a reference or control virus or to a greater extent than absence of treatment with the virus. For purposes herein, exemplary of a reference or control virus is the LIVP virus designated GLV-1h68. Whether anti-tumor activity is "greater" or "improved" can be determined by assessing the effect of a virus and, if necessary, a control or reference virus, on a parameter indicative of anti-tumor activity. It is understood that when comparing the activity of two or more different viruses, the amount of virus (e.g. pfu) used in an in vitro assay or administered in vivo is the same or similar, and the conditions (e.g. in vivo dosage regime) of the in vitro assay or in vivo assessment are the same or similar.

As used herein, "genetic therapy" or "gene therapy" refers to administration of a nucleic acid that encodes for a biological therapeutic. Genetic therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells, such as directly or in a vector or other delivery vehicle, in a manner such that the heterologous nucleic acid, such as DNA, is expressed and a therapeutic product encoded thereby is produced. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy also can be used to deliver nucleic acid encoding a gene product that replaces a defective gene or supplements a gene product produced by the mammalian or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy also can involve delivery of an inhibitor or repressor or other modulator of gene expression. In some embodiments, the nucleic acid encodes a reporter protein for detection in the methods herein. In some embodiments, the nucleic acid is contained in a vector. The vector can be a viral vector, mammalian vector, bacterial vector, insect vector, plant vector and artificial chromosome. In some embodiments, the vector is administered in a liposome, PEGylated liposome, nanoparticle, lipid-based nanoparticle or lymphocyte. In some embodiments, the vector is delivered or administered directly to a subject.

As used herein, immunotherapy refers to treatment of a disease or disorder by inducing, enhancing or suppressing an immune response through the use of immunomodulators, such as interleukins, cytokines, chemokines, cytosine phosphate-guanosine, oligodeoxynucleotides and glucans, and cells, such as T cells, lymphocytes, macrophages, dendritic cells, natural killer cells and cytotoxic T lymphocytes. Use of such immunomodulators or cells supplements, enhances, replaces or otherwise modify's the subject's own inadequate or inappropriate immune response. Cancer immunotherapy refers to stimulation of the immune system to reject and destroy tumors, for example, with cytokines. Active immunotherapy involves injection of cells or proteins, for example, cancer or tumor cells, to generate either new or enhance systemic immune responses to the administered cell or protein. Passive immunotherapy involves the administration of an antibody.

As used herein, adoptive immunotherapy refers to treatment of tumors, cancers or proliferative disorders using cells having anti-tumor activity. Cells for adoptive immunotherapy include but are not limited to activated or expanded T cells, lymphocytes, macrophages, dendritic cells, natural killer cells and cytotoxic T lymphocytes. Immune cells are administered to a host with the aim that the cells mediate either directly or indirectly specific immunity to tumor cells and/or antigenic components or regression of the tumor or treatment of infectious diseases.

As used herein, the terms overproduce or overexpress when used in reference to a substance, molecule, compound or composition made in a cell refers to production or expression at a level that is greater than a baseline, normal or usual level of production or expression of the substance, molecule, compound or composition by the cell. A baseline, normal or usual level of production or expression includes no production/expression or limited, restricted or regulated production/expression. Such overproduction or overexpression is typically achieved by modification of cell.

As used herein, an agent or compound that modulates the activity of a protein or expression of a gene or nucleic acid either decreases or increases or otherwise alters the activity of the protein or, in some manner, up- or down-regulates or otherwise alters expression of the nucleic acid in a cell.

As used herein, a heterologous nucleic acid (also referred to as exogenous nucleic acid or foreign nucleic acid) refers to a nucleic acid that is not normally produced in vivo by an organism or virus from which it is expressed or that is produced by an organism or a virus but is at a different locus, or that mediates or encodes mediators that alter expression of endogenous nucleic acid, such as DNA, by affecting transcription, translation, or other regulatable biochemical processes. Hence, heterologous nucleic acid is often not normally endogenous to a virus into which it is introduced. Heterologous nucleic acid can refer to a nucleic acid molecule from another virus in the same organism or another organism, including the same species or another species. Heterologous nucleic acid, however, can be endogenous, but is nucleic acid that is expressed from a different locus or altered in its expression or sequence (e.g., a plasmid). Thus, heterologous nucleic acid includes a nucleic acid molecule not present in the exact orientation or position as the counterpart nucleic acid molecule, such as DNA, is found in a genome. Generally, although not necessarily, such nucleic acid encodes RNA and proteins that are not normally produced by the virus or in the same way in the virus in which it is expressed. Any nucleic acid, such as DNA, that one of skill in the art recognizes or considers as heterologous, exogenous or foreign to the virus in which the nucleic acid is expressed is herein encompassed by heterologous nucleic acid. Examples of heterologous nucleic acid include, but are not limited to, nucleic acid that encodes exogenous peptides/proteins, including diagnostic and/or therapeutic agents. Proteins that are encoded by heterologous nucleic acid can be expressed within the virus, secreted, or expressed on the surface of the virus in which the heterologous nucleic acid has been introduced.

As used herein, an endogenous nucleic acid or protein refers to a nucleic acid or protein that is native to the organism or virus from which it is expressed.

As used herein, a viral clonal strain or virus strain preparation that contains heterologous nucleic acid refers to such strains that contain nucleic acid not present in the parental clonal strain. For example, the virus whose sequence is set forth in SEQ ID NO: 91 is a clonal strain, but the virus of SEQ ID NO: 90, designated GLV-1h68, contains heterologous nucleic acid, such as the insert designated RUC-GFP.

As used herein, a heterologous protein or heterologous polypeptide (also referred to as exogenous protein, exogenous polypeptide, foreign protein or foreign polypeptide) refers to a protein that is not normally produced by host, such as the virus.

As used herein, "operably" or "operatively linked" when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator. "Operative linkage" of heterologous nucleic acids to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of a nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or transcription, it can be necessary to remove, add or alter 5' untranslated portions of the clones to eliminate extra, potentially inappropriate, alternative translation initiation (i.e., start) codons or other sequences that can interfere with or reduce expression, either at the level of transcription or translation. In addition, consensus ribosome binding sites can be inserted immediately 5' of the start codon and can enhance expression (see, e.g., Kozak *J. Biol. Chem.* 266: 19867-19870 (1991) and Shine and Delgarno, *Nature* 254 (5495):34-38 (1975)). The desirability of (or need for) such modification can be empirically determined.

As used herein, a heterologous promoter refers to a promoter that is not normally found in the wild-type organism or virus or that is at a different locus as compared to a wild-type organism or virus. A heterologous promoter is often not endogenous to a virus into which it is introduced, but has been obtained from another virus or prepared synthetically. A heterologous promoter can refer to a promoter from another virus in the same organism or another organism, including the same species or another species. A heterologous promoter, however, can be endogenous, but is a promoter that is altered in its sequence or occurs at a different locus (e.g., at a different location in the genome or on a plasmid). Thus, a heterologous promoter includes a promoter not present in the exact orientation or position as the counterpart promoter is found in a genome.

A synthetic promoter is a heterologous promoter that has a nucleotide sequence that is not found in nature. A synthetic promoter can be a nucleic acid molecule that has a synthetic sequence or a sequence derived from a native promoter or portion thereof. A synthetic promoter also can be a hybrid promoter composed of different elements derived from different native promoters.

As used herein, vector (or plasmid) refers to a nucleic acid construct that contains discrete elements that are used to introduce heterologous nucleic acid into cells for either expression of the nucleic acid or replication thereof. The vectors typically remain episomal, but can be designed to effect stable integration of a gene or portion thereof into a chromosome of the genome. Selection and use of such vectors are well known to those of skill in the art. Expression vectors include vectors capable of expressing DNA that is operatively linked with regulatory sequences, such as promoter regions, that are capable of effecting expression of the DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. A vector can be a viral vector, mammalian vector, bacterial vector, insect vector and plant vector. Also contemplated are vectors that are artificial chromosomes, such as yeast artificial chromosomes and mammalian artificial chromosomes. In some embodiments, the vector is administered in a liposome, PEGylated liposome, nanoparticle, lipid-based nanoparticle or lymphocyte. In some embodiments, the vector is delivered or administered directly to a subject. Selection and use of such vehicles are well known to those of skill in the art.

As used herein, the term "viral vector" is used according to its art-recognized meaning. It refers to a nucleic acid vector that includes at least one element of viral origin and can be packaged into a viral vector particle. The viral vector particles can be used for the purpose of transferring DNA, RNA or other nucleic acids into cells either in vitro or in vivo. Viral vectors include, but are not limited to, poxvirus vectors (e.g., vaccinia vectors), retroviral vectors, lentivirus vectors, herpes virus vectors (e.g., HSV), baculovirus vectors, cytomegalovirus (CMV) vectors, papillomavirus vectors, simian virus (SV40) vectors, semliki forest virus vectors, phage vectors, adenoviral vectors and adeno-associated viral (AAV) vectors.

As used herein, nucleic acids include DNA, RNA and analogs thereof, including peptide nucleic acids (PNA) and mixtures thereof. Nucleic acids can be single or double-stranded. Nucleic acids can encode gene products, such as, for example, polypeptides, regulatory RNAs, microRNAs, siRNAs and functional RNAs.

As used herein, a sequence complementary to at least a portion of an RNA, with reference to antisense oligonucleotides, means a sequence of nucleotides having sufficient complementarity to be able to hybridize with the RNA, generally under moderate or high stringency conditions, forming a stable duplex; in the case of double-stranded antisense nucleic acids, a single strand of the duplex DNA (i.e., dsRNA) can thus be assayed, or triplex formation can be assayed. The ability to hybridize depends on the degree of complementarity and the length of the antisense nucleic acid. Generally, the longer the hybridizing nucleic acid, the more base mismatches with an encoding RNA it can contain and still form a stable duplex (or triplex, as the case can be). One skilled in the art can ascertain a tolerable degree of mismatch by use of standard procedures to determine the melting point of the hybridized complex.

As used herein, a substrate refers to an atom, molecule, compound or composition that is a reactant for a reporter protein. For example, a substrate for a reporter enzyme is a compound that is consumed during the catalytic or enzymatic reaction or a molecule that is acted upon by the enzyme. Typically substrates or detectable or generate a detectable product upon interaction with the reporter protein. For example, substrates include fluorescent, luminescent, spectrophotometric, fluorogenic, chromogenic and radioactive substrates. Such substrates can be detected, for example, by visual inspection, with a spectrophotometer, fluorometer, luminometer, scintillation counter or Raman spectrometer, by reflectance measurement, by flow cytometry and by X-rays. Substrates also include contrast agents or alternatively a substrate can generate a contrast agent for use in PET imaging.

As used herein, beta-glucuronidase, β-glucuronidase or gusA refers to enzymes that catalyze the hydrolysis of β-D-glucuronides. Beta-glucuronidases include any of non-human origin including, but not limited to, beta-glucuronidases from mouse (SEQ ID NO:115, DNA set forth in SEQ ID NO:2), rat (SEQ ID NO:114, DNA set forth in SEQ ID NO:6), dog (SEQ ID NO:116, DNA set forth in SEQ ID NO:7), cat (SEQ ID NO:117, DNA set forth in SEQ ID NO:8), pig (SEQ ID NO:120, DNA set forth in SEQ ID NO:11), green monkey (SEQ ID NO:118, DNA set forth in SEQ ID NO:9) and Sumatran orangutan (SEQ ID NO:119, DNA set forth in SEQ ID NO:10). Beta-glucuronidases also include those of human origin. Exemplary of a human beta-glucuronidase is the human beta-glucuronidase set forth in SEQ ID NOS:5 and 121. Beta-glucuronidases also include bacterial beta-glucuronidases, such as beta-glucuronidases from *E. coli* K12 (SEQ ID NO:4, DNA set forth in SEQ ID NO:3), *Shigella flexneri* strain K-18 (SEQ ID NO:128, DNA set forth in SEQ ID NO:127), *Salmonella enterica* (SEQ ID NO:136, DNA set forth in SEQ ID NO:135), *Lactobacillus brevis* strain RO1 (SEQ ID NO:130, DNA set forth in SEQ ID NO:129), *Streptococcus agalactiae* (SEQ ID NO:132, DNA set forth in SEQ ID NO:131), *Clostridium perfringens* (SEQ ID NO:134, DNA set forth in SEQ ID NO:133), *Roseburia intestinalis* (SEQ ID NO:138, DNA set forth in SEQ ID NO:137), *Anaerococcus tetradius* (SEQ ID NO:140, DNA set forth in SEQ ID NO:139), *Victivallis vadensis* (SEQ ID NO:142, DNA set forth in SEQ ID NO:141), *Congregibacter litoralis* (SEQ ID NO:144, DNA set forth in SEQ ID NO:143) and *Aspergillus terreus* (SEQ ID NO:146, DNA set forth in SEQ ID NO:145). Exemplary of a bacterial beta-glucuronidase is the *E. coli* beta-glucuronidase set forth in SEQ ID NO:4. Reference to beta-glucuronidases includes allelic and species variants, truncated forms that have activity, splice variants and other variants, including beta-glucuronidases that have at least 60%, 70%, 80%, 90%, 91%, 92%, 93%, 94%, 95%, 96%, 97%, 98%, 99% or more sequence identity to the beta-glucuronidases set forth in SEQ ID NOS: 1-11, 114-121, 127-146.

As used herein, beta-galactosidase, β-galactosidase or lacZ refers to enzymes that catalyze the hydrolysis of β-galactosides into monosaccharides. Beta-galactosidases include any of non-human origin including, but not limited to, mouse (SEQ ID NO:29, DNA set forth in SEQ ID NO:28) and dog (SEQ ID NO:33, DNA set forth in SEQ ID NO:32). Beta-galactosidases also include those of human origin. Exemplary of a human beta-galactosidase is the human beta-galactosidase set forth in SEQ ID NOS:13 and 122. Beta-galactosidases also include bacterial beta-glucuronidases, such as beta-galactosidases from *E. coli* K12 (SEQ ID NO:14, DNA set forth in SEQ ID NO:15), *Lactobacillus acidophilus* (SEQ ID NO:16, DNA set forth in SEQ ID NO:17), *Sulfolobus solfataricus* (SEQ ID NO:18, DNA set forth in SEQ ID NO:19), *Lactococcus lactis* (SEQ ID NO:20, DNA set forth in SEQ ID NO:21), *Geobacillus kaustiophilus* (SEQ ID NO:22, DNA set forth in SEQ ID NO:23), *Thermus thermophilus* (SEQ ID NO:24, DNA set forth in SEQ ID NO:25), *Bacillus subtilis* (SEQ ID NO:26, DNA set forth in SEQ ID NO:27) and *Clostridium perfringens* (SEQ ID NO:30, DNA set forth in SEQ ID NO:31). Exemplary of a β-galactosidase is human β-galactosidase (set forth in SEQ ID NO:13). Exemplary of a bacterial beta-galactosidase is the *E. coli* beta-galactosidase set forth in SEQ ID NO:14. Reference to beta-glucuronidases includes allelic and species variants, truncated forms that have activity, splice variants and other variants, including beta-glucuronidases that have at least 60%, 70%, 80%, 90%, 91%, 92%, 93%, 94%, 95%, 96%, 97%, 98%, 99% or more sequence identity to the beta-galactosidases set forth in SEQ ID NOS: 12-33 and 122.

As used herein, chloramphenicol acetyltransferases or CAT refers to bacterial enzymes (EC 2.3.1.28) that detoxify the antibiotic chloramphenicol. Chloramphenicol acetyltransferases include, but are not limited to, those from *E. coli* strain DJ33-16 (SEQ ID NO:53, DNA set forth in SEQ ID NO:52), *Pseudomonas aeruginosa* (SEQ ID NO:55, DNA set forth in SEQ ID NO:54), *Staphylococcus aureus* (SEQ ID NO:57, DNA set forth in SEQ ID NO:56), *Agrobacterium tumefaciens* (SEQ ID NO:59, DNA set forth in SEQ ID NO:58), *Clostridium perfingens* (SEQ ID NO:61, DNA set forth in SEQ ID NO:60), *Klebsiella pneumoniae* (SEQ ID NO:63, DNA set forth in SEQ ID NO:62), *Haemophilus influenzae* (SEQ ID NO:65, DNA set forth in SEQ ID NO:64), *Streptococcus agalactiae* (SEQ ID NO:67, DNA set forth in SEQ ID NO:66), *Bacillus pumilus* (SEQ ID NO:69, DNA set forth in SEQ ID NO:68), *Proteus mirabilis* (SEQ ID NO:71, DNA set forth in SEQ ID NO:70), *Salmonella enterica* (SEQ ID NO:73, DNA set forth in SEQ ID NO:72), *Staphylococcus intermedius* (SEQ ID NO:75, DNA set forth in SEQ ID NO:74), *Listonella anguillarum* (SEQ ID NO:77, DNA set forth in SEQ ID NO:76), *Campylobacter coli* (SEQ ID NO:79, DNA set forth in SEQ ID NO:78) and *Acinetobacter baumannii* (SEQ ID NO:81, DNA set forth in SEQ ID NO:80). Reference to chloramphenicol acetyltransferases includes allelic and species variants, truncated forms that have activity, splice variants and other variants, including chloramphenicol acetyltransferases that have at least 60%, 70%, 80%, 90%, 91%, 92%, 93%, 94%, 95%, 96%, 97%, 98%, 99% or more sequence identity to the chloramphenicol acetyltransferases set forth in SEQ ID NOS:52-81.

As used herein, alkaline phosphatases refers to hydrolase enzymes responsible for removing phosphate groups, e.g., dephosphorylating, from many types of molecules, including nucleotides, proteins, and alkaloids. Alkaline phosphatases are most effective in an alkaline environment. Alkaline phosphatase (ALP) catalyzes the hydrolysis of phosphate esters in alkaline buffer and produces an organic radical and inorganic phosphate. Alkaline phosphatases include, but are not limited to, shrimp alkaline phosphatase (SAP), from a species of Arctic shrimp (*Pandalus borealis*) (SEQ ID NO:109, DNA set forth in SEQ ID NO:108), Intestinal Alkaline Phosphatase (AIP; SEQ ID NO:111, DNA set forth in SEQ ID NO:110) and Placental alkaline phosphatase (PALP; SEQ ID NOS: 113, DNA set forth in SEQ ID NO:99 and 112) and secreted alkaline phosphatase (SEAP; SEQ ID NO:126), a C terminally truncated version of PALP. Reference to alkaline phosphatases includes allelic and species variants, truncated forms that have activity, splice variants and other variants, including alkaline phosphatases that have at least 60%, 70%, 80%, 90%, 91%, 92%, 93%, 94%, 95%, 96%, 97%, 98%, 99% or more sequence identity to the alkaline phosphatases set forth in SEQ ID NOS:108-113 and 126.

As used herein, luminescence refers to the detectable electromagnetic (EM) radiation, generally, ultraviolet (UV), infrared (IR) or visible EM radiation that is produced when the excited product of an exergonic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes. Fluorescence is luminescence in which light of a visible color is emitted from a substance under stimulation or excitation by light or other forms radiation such as ultraviolet (UV), infrared (IR) or visible EM radiation.

As used herein, chemiluminescence refers to a chemical reaction in which energy is specifically channeled to a molecule causing it to become electronically excited and subsequently to release a photon, thereby emitting visible light. Temperature does not contribute to this channeled energy. Thus, chemiluminescence involves the direct conversion of chemical energy to light energy.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which, upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives such as, for example, click beetle luciferase or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of Cypridina (Vargula) luciferin and another class of luciferases catalyzes the oxidation of Coleoptera luciferin. Thus, luciferase refers to an enzyme or photoprotein that catalyzes a bioluminescent reaction (a reaction that produces bioluminescence). The luciferases, such as firefly and *Gaussia* and *Renilla* luciferases, are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein, or a mixture of proteins (e.g., bacterial luciferase), that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Reference, for example, to *Renilla* luciferase refers to an enzyme isolated from member of the genus *Renilla* or an equivalent molecule obtained from any other source, such as from another related copepod, or that has been prepared synthetically. It is intended to encompass *Renilla* luciferases with conservative amino acid substitutions that do not substantially alter activity. Conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

As used herein, bioluminescence substrate refers to the compound that is oxidized in the presence of a luciferase and any necessary activators and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Typical substrates include those that are oxidized in the presence of a luciferase or protein in a light-generating reaction. Bioluminescence substrates, thus, include those compounds that those of skill in the art recognize as luciferins. Luciferins, for example, include firefly luciferin, Cypridina (also known as Vargula) luciferin (coelenterazine), bacterial luciferin, as well as synthetic analogs of these substrates or other compounds that are oxidized in the presence of a luciferase in a reaction that produces bioluminescence.

As used herein, capable of conversion into a bioluminescence substrate refers to being susceptible to chemical reaction, such as oxidation or reduction, which yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are bioluminescence substrates.

As used herein, a bioluminescence generating system refers to the set of reagents required to conduct a bioluminescent reaction. Thus, the specific luciferase, luciferin and other substrates, solvents and other reagents that can be required to complete a bioluminescent reaction form a bioluminescence system. Thus a bioluminescence generating system refers to any set of reagents that, under appropriate reaction conditions, yield bioluminescence. Appropriate reaction conditions refer to the conditions necessary for a bioluminescence reaction to occur, such as pH, salt concentrations and temperature. In general, bioluminescence systems include a bioluminescence substrate, luciferin, a luciferase, which includes enzymes luciferases and photoproteins and one or more activators. A specific bioluminescence system can be identified by reference to the specific organism from which the luciferase derives; for example, the *Renilla* bioluminescence system includes a *Renilla* luciferase, such as a luciferase isolated from *Renilla* or produced using recombinant methods or modifications of these luciferases. This system also includes the particular activators necessary to complete the bioluminescence reaction, such as oxygen and a substrate with which the luciferase reacts in the presence of the oxygen to produce light.

As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art. Exemplary FPs include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. Extending the spectrum of available colors of fluorescent proteins to blue, cyan, orange, yellow and red variants provides a method for multicolor tracking of fusion proteins.

As used herein, *Aequorea* GFP refers to GFPs from the genus *Aequorea* and to mutants or variants thereof. Such variants and GFPs from other species, such as *Anthozoa* reef coral, *Anemonia* sea anemone, *Renilla* sea pansy, *Galaxea* coral, *Acropora* brown coral, *Trachyphyllia* and *Pectimidae* stony coral and other species are well known and are available and known to those of skill in the art. Exemplary GFP variants include, but are not limited to BFP, CFP, YFP and OFP. Examples of fluorescent proteins and their variants include GFP proteins, such as Emerald (Invitrogen, Carlsbad, Calif.), EGFP (Clontech, Palo Alto, Calif.), Azami-Green (MBL International, Woburn, Mass.), Kaede (MBL International, Woburn, Mass.), ZsGreen1 (Clontech, Palo Alto, Calif.) and CopGFP (Evrogen/Axxora, LLC, San Diego, Calif.); CFP proteins, such as Cerulean (Rizzo, *Nat Biotechnol.* 22(4): 445-9 (2004)), mCFP (Wang et al., *PNAS U.S.A.* 101(48): 16745-9 (2004)), AmCyan1 (Clontech, Palo Alto, Calif.), MiCy (MBL International, Woburn, Mass.), and CyPet (Nguyen and Daugherty, *Nat Biotechnol.* 23(3):355-60 (2005)); BFP proteins such as EBFP (Clontech, Palo Alto, Calif.); YFP proteins such as EYFP (Clontech, Palo Alto, Calif.), YPet (Nguyen and Daugherty, *Nat Biotechnol.* 23(3): 355-60 (2005)), Venus (Nagai et al., *Nat. Biotechnol.* 20(1): 87-90 (2002)), ZsYellow (Clontech, Palo Alto, Calif.), and mCitrine (Wang et al., *PNAS USA.* 101(48):16745-9 (2004)); OFP proteins such as cOFP (Stratagene, La Jolla, Calif.), mKO (MBL International, Woburn, Mass.), and mOrange;

and others (see, e.g., Shaner N C, Steinbach P A, and Tsien R Y., *Nat Methods.* 2(12):905-9 (2005)).

As used herein, red fluorescent protein, or RFP, refers to the *Discosoma* RFP (DsRed) that has been isolated from the corallimorph *Discosoma* (Matz et al., *Nature Biotechnology* 17: 969-973 (1999)), and red or far-red fluorescent proteins from any other species, such as *Heteractis* reef coral and *Actinia* or *Entacmaea* sea anemone, as well as variants thereof. RFPs include, for example, *Discosoma* variants, such as monomeric red fluorescent protein 1 (mRFP1), mCherry, tdTomato, mStrawberry, mTangerine (Wang et al., *PNAS USA.* 101(48):16745-9 (2004)), DsRed2 (Clontech, Palo Alto, Calif.), and DsRed-T1 (Bevis and Glick, *Nat. Biotechnol.,* 20: 83-87 (2002)), *Anthomedusa* J-Red (Evrogen) and *Anemonia* AsRed2 (Clontech, Palo Alto, Calif.). Far-red fluorescent proteins include, for example, *Actinia* AQ143 (Shkrob et al., *Biochem J.* 392(Pt 3):649-54 (2005)), *Entacmaea* eqFP611 (Wiedenmann et al. *Proc. Natl. Acad. Sci. USA.* 99(18):11646-51 (2002)), *Discosoma* variants such as mPlum and mRasberry (Wang et al., *PNAS USA.* 101(48): 16745-9 (2004)), and Heteractis HcRed1 and t-HcRed (Clontech, Palo Alto, Calif.). Near-infrared fluorescent proteins include, for example, mKate, TurboFP635 or Katushka, mNeptune and IFP1.4 (Shcherbo et al., (2007) *Nat Methods* 4:741-746).

As used herein, antibody refers to monoclonal antibodies, polyclonal antibodies, and chimeric antibodies. Antibodies and immunoglobulins are glycoproteins having the same structural characteristics. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. The antibody may be from recombinant sources and/or produced in transgenic animals. Antibodies include Fab, Fab', F(ab')$_2$, scFv, dsFv, ds-scFv, dimers, minibodies, diabodies, and multimers thereof and multispecific antibody fragments.

As used herein, an antigen is a substance that evokes the production of one or more antibodies. Antigens are characterized by their ability to be "bound" in the antigen-binding site of an antibody. Antigens include proteins and polysaccharides, such as those from bacteria, viruses and microorganism.

As used herein, nanoparticle refers to a microscopic particle whose size is measured in nanometers. Often such particles in nanoscale are used in biomedical applications acting as drug carriers or imaging agents. Nanoparticles can be conjugated to other agents, including, but not limited to detectable/diagnostic agents or therapeutic agents.

As used herein, an in vivo method refers to a method performed within the living body of a subject.

As used herein, "nucleic acids" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, a peptide refers to a polypeptide that is greater than or equal to 2 amino acids in length, and less than or equal to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3557-3559 (1968), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is defined to include the amino acids listed in the Table of Correspondence (Table 1) and modified and unusual amino acids, such as those referred to in 37 C.F.R. §§1.821-1.822, and incorporated herein by reference. Furthermore, a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, the "naturally occurring α-amino acids" are the residues of those 20 α-amino acids found in nature which are incorporated into protein by the specific recognition of the charged tRNA molecule with its cognate mRNA codon in humans. Non-naturally occurring amino acids thus include, for example, amino acids or analogs of amino acids other than the 20 naturally-occurring amino acids and include, but are not limited to, the D-isostereomers of amino acids. Exemplary non-natural amino acids are described herein and are known to those of skill in the art.

As used herein, a DNA construct is a single- or double-stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule may not be paired. Such unpaired ends will, in general, not exceed 20 nucleotides in length.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g. Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carrillo, H. & Lipton, D., SIAM J Applied Math 48:1073 (1988)).

As used herein, homologous (with respect to nucleic acid and/or amino acid sequences) means about greater than or equal to 25% sequence homology, typically greater than or equal to 25%, 40%, 50%, 60%, 70%, 80%, 85%, 90% or 95% sequence homology; the precise percentage can be specified if necessary. For purposes herein the terms "homology" and "identity" are often used interchangeably, unless otherwise indicated. In general, for determination of the percentage homology or identity, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) *SIAM J Applied Math* 48:1073). By sequence homology, the number of conserved amino acids is determined by standard alignment algorithms programs, and can be used with default gap penalties established by each supplier. Substantially homologous nucleic acid molecules hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I): 387 (1984)), BLASTP, BLASTN, FASTA (Atschul, S. F., et al., *J Mol Biol* 215:403 (1990)); Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.). Percent homology or identity of proteins and/or nucleic acid molecules can be determined, for example, by comparing sequence information using a GAP computer program (e.g., Needleman et al. (1970) J. Mol. Biol. 48:443, as revised by Smith and Waterman ((1981) Adv. Appl. Math. 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide. As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result is independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, "primer pair" refers to a set of primers that includes a 5' (upstream) primer that hybridizes with the 5' end of a sequence to be amplified (e.g. by PCR) and a 3' (downstream) primer that hybridizes with the complement of the 3' end of the sequence to be amplified.

As used herein, "specifically hybridizes" refers to annealing, by complementary base-pairing, of a nucleic acid molecule (e.g. an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1×SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application. Complementary, when referring to two nucleotide sequences, means that the two sequences of nucleotides are capable of hybridizing, typically with less than 25%, 15% or 5% mismatches between opposed nucleotides. If necessary, the percentage of complementarity will be specified. Typically the two molecules are selected such that they will hybridize under conditions of high stringency.

As used herein, substantially identical to a product means sufficiently similar so that the property of interest is sufficiently unchanged so that the substantially identical product can be used in place of the product.

As used herein, it also is understood that the terms "substantially identical" or "similar" varies with the context as understood by those skilled in the relevant art.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide. Reference to an allelic variant herein generally refers to variations n proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include modifications such as substitutions, deletions and insertions of nucleotides. An allele of a gene also can be a form of a gene containing a mutation.

As used herein, species variants refer to variants in polypeptides among different species, including different mammalian species, such as mouse and human. For example for β-glucuronidase, exemplary of species variants provided herein are mouse, rat, cat, dog, pig, green monkey and Sumatran orangutan. Generally, species variants have 70%, 75%, 80%, 85%, 90%, 91%, 92%, 93%, 94%, 95%, 96%, 97%, 98% or more sequence identity. Corresponding residues between and among species variants can be determined by comparing and aligning sequences to maximize the number of matching nucleotides or residues, for example, such that identity between the sequences is equal to or greater than 95%, equal to or greater than 96%, equal to or greater than 97%, equal to or greater than 98% or equal to greater than 99%. The position of interest is then given the number assigned in the reference nucleic acid molecule. Alignment can be effected manually or by eye, particularly, where sequence identity is greater than 80%.

As used herein, a human protein is one encoded by a nucleic acid molecule, such as DNA, present in the genome of a human, including all allelic variants and conservative variations thereof. A variant or modification of a protein is a human protein if the modification is based on the wildtype or prominent sequence of a human protein.

As used herein, a splice variant refers to a variant produced by differential processing of a primary transcript of genomic DNA that results in more than one type of mRNA.

As used herein, modification is in reference to modification of a sequence of amino acids of a polypeptide or a sequence of nucleotides in a nucleic acid molecule and includes deletions, insertions, and replacements (e.g. substitutions) of amino acids and nucleotides, respectively. Exemplary of modifications are amino acid substitutions. An amino-acid substituted polypeptide can exhibit 65%, 70%, 80%, 85%, 90%, 91%, 92%, 93%, 94%, 95%, 96%, 97%, 98% or more sequence identity to a polypeptide not containing the amino acid substitutions. Amino acid substitutions can be conservative or non-conservative. Generally, any modification to a polypeptide retains an activity of the polypeptide. Methods of modifying a polypeptide are routine to those of skill in the art, such as by using recombinant DNA methodologies.

As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Such substitutions can be made in accordance with those set forth in TABLE 2 as follows:

TABLE 2

| Original residue | Exemplary conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with known conservative substitutions.

As used herein, the term promoter means a portion of a gene containing DNA sequences that provide for the binding of RNA polymerase and initiation of transcription. Promoter sequences are commonly, but not always, found in the 5' non-coding region of genes.

As used herein, isolated or purified polypeptide or protein or biologically-active portion thereof is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

Hence, reference to a substantially purified polypeptide, refers to preparations of proteins that are substantially free of cellular material includes preparations of proteins in which the protein is separated from cellular components of the cells from which it is isolated or recombinantly-produced. In one embodiment, the term substantially free of cellular material includes preparations of enzyme proteins having less than about 30% (by dry weight) of non-enzyme proteins (also referred to herein as a contaminating protein), generally less than about 20% of non-enzyme proteins or 10% of non-enzyme proteins or less than about 5% of non-enzyme proteins. When the enzyme protein is recombinantly produced, it also is substantially free of culture medium, i.e., culture medium represents less than about or at 20%, 10% or 5% of the volume of the enzyme protein preparation.

As used herein, the term substantially free of chemical precursors or other chemicals includes preparations of enzyme proteins in which the protein is separated from chemical precursors or other chemicals that are involved in the synthesis of the protein. The term includes preparations of enzyme proteins having less than about 30% (by dry weight), 20%, 10%, 5% or less of chemical precursors or non-enzyme chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant means or using recombinant DNA methods means the use of the well known methods of molecular biology for expressing proteins encoded by cloned DNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein the term "assessing" is intended to include quantitative and qualitative determination in the sense of obtaining an absolute value for the activity of a protein, such as an enzyme, or a domain thereof, present in the sample, and also of obtaining an index, ratio, percentage, visual or other value indicative of the level of the activity. Assessment can be direct or indirect. For example, the chemical species actually detected need not of course be the enzymatically cleaved product itself but can for example be a derivative thereof or some further substance. For example, detection of a cleavage product can be a detectable moiety such as a fluorescent moiety.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities.

As used herein equivalent, when referring to two sequences of nucleic acids, means that the two sequences in question encode the same sequence of amino acids or equivalent proteins. When equivalent is used in referring to two proteins or peptides, it means that the two proteins or peptides have substantially the same amino acid sequence with only amino acid substitutions that do not substantially alter the activity or function of the protein or peptide. When equivalent refers to a property, the property does not need to be present to the same extent (e.g., two peptides can exhibit different rates of the same type of enzymatic activity), but the activities are usually substantially the same.

As used herein, "modulate" and "modulation" or "alter" refer to a change of an activity of a molecule, such as a protein. Exemplary activities include, but are not limited to, biological activities, such as signal transduction. Modulation can include an increase in the activity (i.e., up-regulation or agonist activity), a decrease in activity (i.e., down-regulation or inhibition) or any other alteration in an activity (such as a change in periodicity, frequency, duration, kinetics or other parameter). Modulation can be context dependent and typically modulation is compared to a designated state, for example, the wildtype protein, the protein in a constitutive state, or the protein as expressed in a designated cell type or condition.

As used herein, a composition refers to any mixture. It can be a solution, suspension, liquid, powder, paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, "disease or disorder" refers to a pathological condition in an organism resulting from cause or condition including, but not limited to, infections, acquired conditions, genetic conditions, and characterized by identifiable symptoms.

As used herein, treatment means any manner in which the symptoms of a condition, disorder or disease or other indication, are ameliorated or otherwise beneficially altered.

As used herein, a disease or disorder refers to a pathological condition in an organism resulting from, for example, infection or genetic defect, and characterized by identifiable symptoms. An exemplary disease as described herein is a neoplastic disease, such as cancer.

As used herein, neoplastic disease refers to any disorder involving cancer, including tumor development, growth, metastasis and progression.

As used herein, cancer is a term for diseases caused by or characterized by any type of malignant tumor, including metastatic cancers, lymphatic tumors, and blood cancers. Exemplary cancers include, but are not limited to, leukemia, lymphoma, pancreatic cancer, lung cancer, ovarian cancer, breast cancer, cervical cancer, bladder cancer, prostate cancer, glioma tumors, adenocarcinomas, liver cancer and skin cancer. Exemplary cancers in humans include a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Exemplary cancers commonly diagnosed in dogs, cats, and other pets include, but are not limited to, lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma (e.g., granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma, follicular lymphoma, intestinal lymphosarcoma, fibrosarcoma and pulmonary squamous cell carcinoma. Exemplary cancers diagnosed in rodents, such as a ferret, include, but are not limited to, insulinoma, lymphoma, sarcoma, neuroma, pancreatic islet cell tumor, gastric MALT lymphoma and gastric adenocarcinoma. Exemplary neoplasias affecting agricultural livestock include, but are not limited to, leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulo-endotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lymphadenitis (CLA): chronic, infectious, contagious disease of sheep and goats caused by the bacterium *Corynebacterium pseudotuberculosis*, and contagious lung tumor of sheep caused by jaagsiekte.

As used herein, therapeutic agents are agents that ameliorate the symptoms of a disease or disorder or ameliorate the disease or disorder. Therapeutic agent, therapeutic compound, or therapeutic regimens include conventional drugs and drug therapies, including vaccines for treatment or prevention (i.e., reducing the risk of getting a particular disease or disorder), which are known to those skilled in the art and described elsewhere herein. Therapeutic agents for the treatment of neoplastic disease or cancer therapy include, but are not limited to, moieties that inhibit cell growth or promote cell death, that can be activated to inhibit cell growth or promote cell death, or that activate another agent to inhibit cell growth or promote cell death. Therapeutic agents for use in the methods provided herein can be, for example, an anticancer agent. Exemplary therapeutic agents include, for example, therapeutic microorganisms, such as therapeutic viruses and bacteria, cytokines, growth factors, photosensitizing agents, radionuclides, toxins, antimetabolites, signaling modulators, anticancer antibiotics, anticancer antibodies, angiogenesis inhibitors, radiation therapy, chemotherapeutic compounds or a combination thereof.

As used herein, a "metastasis" refers to the spread of cancer from one part of the body to another. For example, in the metastatic process, malignant cells can spread from the site of the primary tumor in which the malignant cells arose and move into lymphatic and blood vessels, which transport the cells to normal tissues elsewhere in an organism where the cells continue to proliferate. A tumor formed by cells that have spread by metastasis is called a "metastatic tumor," a "secondary tumor" or a "metastasis."

As used herein, treatment of a subject that has a neoplastic disease, including a tumor or metastasis, means any manner of treatment in which the symptoms of having the neoplastic disease are ameliorated or otherwise beneficially altered. Typically, treatment of a tumor or metastasis in a subject encompasses any manner of treatment that results in slowing of tumor growth, lysis of tumor cells, reduction in the size of the tumor, prevention of new tumor growth, or prevention of metastasis of a primary tumor, including inhibition vascularization of the tumor, tumor cell division, tumor cell migration or degradation of the basement membrane or extracellular matrix.

As used herein, the term "wound" refers to a physical trauma to an organism that can damage cells, tissues, organs and systems of the organism. Wounds include open wounds, such as incisions, burns, lacerations, abrasions, puncture wounds and penetration wounds, which are exposed to the environment, and closed wounds, which are typically internal to the organism and include, for example, contusions, hematomas and crushing injuries.

As used herein, inflamed tissue refers to tissue affected by inflammation and affected cells contained within the tissue. The term inflammation is intended to represent the normal response of the immune system to infection or irritation.

As used herein, therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, amelioration or alleviation of the symptoms of a particular disorder, such as by administration of a particular pharmaceutical composition, refers to any lessening, whether permanent or temporary, lasting or transient that can be attributed to or associated with administration of the composition.

As used herein, the term "therapeutic virus" refers to a virus that is administered for the treatment of a disease or disorder, such as a neoplastic disease, such as cancer, a tumor and/or a metastasis or inflammation or wound or diagnosis thereof and or both. Generally, a therapeutic virus herein is one that exhibits anti-tumor activity and minimal toxicity.

As used herein, a tumor, also known as a neoplasm, is an abnormal mass of tissue that results when cells proliferate at an abnormally high rate. Tumors can show partial or total lack of structural organization and functional coordination with normal tissue. Tumors can be benign (not cancerous), or malignant (cancerous). As used herein, a tumor is intended to encompass hematopoietic tumors as well as solid tumors.

Malignant tumors can be broadly classified into three major types. Carcinomas are malignant tumors arising from epithelial structures (e.g. breast, prostate, lung, colon, pancreas). Sarcomas are malignant tumors that originate from connective tissues, or mesenchymal cells, such as muscle, cartilage, fat or bone. Leukemias and lymphomas are malignant tumors affecting hematopoietic structures (structures pertaining to the formation of blood cells) including components of the immune system. Other malignant tumors include, but are not limited to, tumors of the nervous system (e.g. neurofibromatomas), germ cell tumors, and blastic tumors.

As used herein, proliferative disorders include any disorders involving abnormal proliferation of cells (i.e. cells proliferate more rapidly compared to normal tissue growth), such as, but not limited to, neoplastic diseases.

As used herein, a "tumor cell" is any cell that is part of a tumor. Typically, the viruses provided herein preferentially infect tumor cells in a subject compared to normal cells.

As used herein, a "metastatic cell" is a cell that has the potential for metastasis. Metastatic cells have the ability to metastasize from a first tumor in a subject and can colonize tissue at a different site in the subject to form a second tumor at the site.

As used herein, "tumorigenic cell," is a cell that, when introduced into a suitable site in a subject, can form a tumor. The cell can be non-metastatic or metastatic.

As used herein, a "normal cell" is a cell that is not derived from a tumor.

As used herein, the term "cell" refers to the basic unit of structure and function of a living organism as is commonly understood in the biological sciences. A cell can be a unicellular organism that is self-sufficient and that can exist as a functional whole independently of other cells. A cell also can be one that, when not isolated from the environment in which it occurs in nature, is part of a multicellular organism made up of more than one type of cell. Such a cell, which can be thought of as a "non-organism" or "non-organismal" cell, generally is specialized in that it performs only a subset of the functions performed by the multicellular organism as whole. Thus, this type of cell is not a unicellular organism. Such a cell can be a prokaryotic or eukaryotic cell, including animal cells, such as mammalian cells, human cells and non-human animal cells or non-human mammalian cells. Animal cells include any cell of animal origin that can be found in an animal. Thus, animal cells include, for example, cells that make up the various organs, tissues and systems of an animal.

As used herein an "isolated cell" is a cell that exists in vitro and is separate from the organism from which it was originally derived.

As used herein, a "cell line" is a population of cells derived from a primary cell that is capable of stable growth in vitro for many generations. Cell lines are commonly referred to as "immortalized" cell lines to describe their ability to continuously propagate in vitro.

As used herein a "tumor cell line" is a population of cells that is initially derived from a tumor. Such cells typically have undergone some change in vivo such that they theoretically have indefinite growth in culture; unlike primary cells, which can be cultured only for a finite period of time. Such cells can form tumors after they are injected into susceptible animals.

As used herein, a "primary cell" is a cell that has been isolated from a subject.

As used herein, a "host cell" or "target cell" are used interchangeably to mean a cell that can be infected by a virus.

As used herein, the term "tissue" refers to a group, collection or aggregate of similar cells generally acting to perform a specific function within an organism.

As used herein, the terms immunoprivileged cells and immunoprivileged tissues refer to cells and tissues, such as solid tumors, which are sequestered from the immune system. Generally, administration of a virus to a subject elicits an immune response that clears the virus from the subject. Immunoprivileged sites, however, are shielded or sequestered from the immune response, permitting the virus to survive and generally to replicate. Immunoprivileged tissues include proliferating tissues, such as tumor tissues.

As used herein, cell therapy refers to treatment with a cell, such as a cell transplant. The cell transplant can be selected from among, but not limited to, pancreatic islet, bone marrow, endothelial, epidermal, myoblast, neural and stem cell transplants. The cell can be modified to express a reporter, or can be infected ex vivo, with a virus or viral vector or other eukaryotic vector, to express the reporter. In some embodiments, the cell contains a viral vector, mammalian vector, bacterial vector, insect vector, plant vector or artificial chromosome encoding a reporter protein. In other embodiments, the cell is infected with a virus prior to administration to the subject. In such examples, the virus contains a reporter gene that encodes a reporter protein.

As used herein, a compound produced in a tumor or other immunoprivileged site refers to any compound that is produced in the tumor or tumor environment by virtue of the presence of an introduced virus, generally a recombinant virus, expressing one or more gene products. For example, a compound produced in a tumor can be, for example, an encoded polypeptide or RNA, a metabolite, or compound that is generated by a recombinant polypeptide and the cellular machinery of the tumor or immunoprivileged tissue or cells.

As used herein, a subject includes any organism, including an animal for whom diagnosis, screening, monitoring or treatment is contemplated. Animals include mammals such as primates and domesticated animals. An exemplary primate is human. A patient refers to a subject, such as a mammal, primate, human, or livestock subject afflicted with a disease condition or for which a disease condition is to be determined or risk of a disease condition is to be determined.

As used herein, a delivery vehicle for administration refers to a lipid-based or other polymer-based composition, such as liposome, PEGylated liposome, nanoparticle, lipid-based nanoparticle, lymphocyte, micelle or reverse micelle, that associates with an agent, such as a virus provided herein, for delivery into a host subject.

As used herein, a patient refers to a human subject exhibiting symptoms of a disease or disorder.

As used herein, about the same means within an amount that one of skill in the art would consider to be the same or to be within an acceptable range of error. For example, typically, for pharmaceutical compositions, within at least 1%, 2%, 3%, 4%, 5% or 10% is considered about the same. Such amount can vary depending upon the tolerance for variation in the particular composition by subjects.

As used herein, animal includes any animal, such as, but are not limited to primates including humans, gorillas and monkeys; rodents, such as mice and rats; fowl, such as chickens; ruminants, such as goats, cows, deer and sheep; pigs and other animals. Non-human animals exclude humans as the contemplated animal.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a compound comprising or containing "an extracellular domain" includes compounds with one or a plurality of extracellular domains.

As used herein, ranges and amounts can be expressed as "about" a particular value or range. About also includes the exact amount. Hence "about 5 bases" means "about 5 bases" and also "5 bases."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. Overview of Method

Provided herein are methods for monitoring biological therapies, including detecting whether they have initiated, their progress and their effects. All of the therapies require at least to some extent, amplification of the agent or a product thereof. The methods provided herein detect or identify a product that is produced, either an endogenous or heterologous product of the therapeutic, that reflects that the therapeutic has reached or colonized a target in the treated subject. Thus, if stem cells are administered, the method detects in a sample, such as a body fluid sample, that is different from the locus of the treatment, expression of a product of the stem cells. The stem cells or cells for adoptive immunotherapy can be modified to express a protein or other reporter, and then, the protein or product of the cells is detected in a sample. For example, for oncolytic viral therapy, virus is administered. The viruses accumulate in tumor cells, and as therapy proceeds, the viruses express encoded products that, as shown herein, are shed, or released, and can be detected in body fluids, such as serum, and non-tumor tissues. If therapy is proceeding, the oncolytic viruses replicate and the products can be detected. If therapy is not effective, then product will not begin to accumulate or be detectable in non-target tissues and body fluids.

Hence, for example, the methods herein, can monitor or detect the efficacy of the biological therapy, for example, by non-invasively sampling a body fluid and detecting a product, either directly or by virtue of its activity, that is encoded in the genome of the biological therapy. In some embodiments, the biological therapeutic can be modified to express a reporter gene, such as nucleic acid that encodes an enzyme. If therapy is effective, i.e., the stem cells are replicating or the oncolytic virus is accumulating in tumor cells, the activity of the reporter protein, e.g., enzyme, in the sample can be detected, and typically compared to a control or standard, to show that it is increased.

In some embodiments of the methods, a subject is treated with a biological therapeutic that encodes a reporter protein. The biological therapeutic can express the reporter constitutively or under the control of a constitutive promoter or other regulatory signal so that expression, for example, only is effected when monitoring is desired. The reporter gene can be introduced into the genome of the biological therapeutic, or can be introduced in a vector. Thus, where the therapy is a cell, such as a stem cell, the stem cell can be modified to express a reporter, or can be infected ex vivo, with a virus or viral vector or other eukaryotic vector, to express the reporter. Alternatively, as noted, the reporter can be a protein endogenously encoded. Similarly, for therapies such as oncolytic therapies, in which a virus or bacterium is administered, the virus or bacterium can be modified to encode the reporter. Reporters include, but are not limited, to enzymes. In some examples, the vector encodes additional heterologous proteins. For example, the vector encodes the reporter gene and an additional heterologous gene, such as a therapeutic protein. Following or during or intermittently or periodically during treatment with the biological therapeutic, a sample, from a locus other than the target tissue or cell of the therapy, such as blood, serum, saliva, and urine, is collected from the subject. If the reporter is an enzyme, the sample or portion thereof, is contacted with a suitable substrate. Following incubation of the sample and the substrate, the sample is monitored to detect the reporter protein or a signal induced by the reporter protein. Detection of the reporter protein allows for in vivo monitoring of viral therapy, bacterial therapy, cell therapy, immunotherapy, adoptive immunotherapy or gene therapy.

1. Biological Therapies

The use of biological therapies, such as stem cell therapy, gene therapy, immunotherapy, oncolytic virotherapy, oncolytic bacterial therapy, cell therapy for regenerative medicine, immunology, oncology and the treatment of various diseases is growing. A feature of these therapies is the required expression of genes that usually are not or are only weakly expressed in the targeted tissue; or, for oncolytic therapies, replication of the virus or bacterium or other oncolytic vector is required. As shown herein, if the therapy has achieved an effect, such as colonization of target tissues, or replication of an oncolytic virus, it is possible to detect products encoded by the biological therapeutic in loci distinct from the target of the therapeutic. These loci include body fluids and tissues that conveniently can be sampled and tested for a product encoded by the therapeutic. The encoded product can be one not normally expressed in the subject in which case detection indicates that the therapeutic is replicating or expressing product, or the product can be one that is produced in which case an increase compared to a standard or the subject's baseline level or other suitable control is assessed. The following discussion describes exemplary biological therapeutics. These are exemplary and not to be construed to be limiting of those for which treatment can be monitored by the methods herein.

a. Oncolytic Viral Therapy

Numerous oncolytic viruses have been identified or developed. These include vaccinia viruses, vesticular stomatis viruses and adenoviruses. When administered, the viruses accumulate in tumor cells and tissues, replicate and lyse the cells, releasing the contents thereof. As shown herein, if the virus is replicating or expressing encoded gene products, these products can be detected in non-tumor tissue, thereby serving as a marker for viral colonization/infection of the tumor cell. The amount expressed and/or expression can be used to assess effectiveness of the therapy. Oncolytic viruses have been genetically altered to attenuate their virulence, to improve their safety profile, enhance their tumor specificity, and they have also been equipped with additional genes, for example cytotoxins, cytokines, or prodrug converting enzymes to improve the overall efficacy of the viruses (see, e.g., Kirn et al., (2009) *Nat Rev Cancer* 9:64-71; Garcia-Aragoncillo et al., (2010) *Curr Opin Mol Ther* 12:403-411; see U.S. Pat. Nos. 7,588,767, 7,588,771, 7,662,398 and 7,754,221 and U.S. Pat. Publ. Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650.

Vaccinia viruses, particular those that are modified to have decreased virulence or that have decreased virulence, are among those that are particularly advantageous. For example, vaccinia virus is a large DNA virus that encodes its own DNA polymerase such that it is able to replicate in the cytoplasm of infected host cells thereby minimizing the risk of DNA integration into the host genome. Vaccinia virus displays a broad host cell range, rapid spread and a high capacity (up to about 25 kbp) for genetic payload of foreign DNA (Moss et al., (1996) *Proc Natl Acad Sci USA* 93:11341-11348). Of note and importance regarding the safety of vaccinia virus, is also its billion-fold use in humans during the eradication program of smallpox, as well as the fact that vaccinia virus is not a human pathogen. Further, certain vaccinia virus strains have been shown to specifically colonize solid tumors, while not infecting other organs (Zhang et al. (2007) *Cancer Res* 67:10038-10046; Yu et al., (2004) *Nat Biotech* 22:313-320; Heo et al., (2011) *Mol Ther* 19:1170-1179; Liu et al. (2008) *Mol Ther* 16:1637-1642; Park et al., (2008) *Lancet Oncol*, 9:533-542; Pedersen et al.: Preliminary results of a Phase 1 study of intravenous administration of GL-ONC1 Vaccinia virus in patients with advanced solid cancer with real time imaging. In 6th NCRI Cancer Conference; BT Convention Center, Liverpool, UK. 2010). The methods provided herein permit reliable monitoring of successful tumor colonization in humans. This has an enormous impact, not only on clinical trials, but also for predicting outcomes of oncolytic virus therapy.

In practicing the methods herein, the presence of endogenous and/or heterologous gene products in non-target samples from treated subjects is assessed as an indicator of the effectiveness or progress of the biological therapy. Among the gene products that can be detected are various reporter genes that have been used for optical (e.g. Puhlmann et al., (2000) *Cancer Gene Ther* 7:66-73) and radiological (e.g. Bennett et al., (2001) *Nat Med* 7:859-863; Chen et al., (2009) *Mol Med* 15:144-151; Dingli et al., (2004) *Blood* 103:1641-1646; Haddad et al., (2011) *J Transl Med* 9:36) imaging. The methods herein have advantages compared to optical and radiological imaging in treated subjects. For example, optical imaging has limitations in penetration depth and radiological imaging is time consuming and requires specialized personnel and expensive equipment.

2. Beta-Glucuronidases as Reporter Proteins

Exemplary of the reporter proteins contemplated herein are beta-glucuronidases. Beta-glucuronidases (β-glucuronidase, GusA) catalyze the hydrolysis of β-D-glucuronides into the corresponding D-glucuronate and alcohol. Mammalian β-glucuronidases have a pH-optimum under acidic conditions (pH 4 to 5) and have reduced capacity at normal (neutral) tissue pH. The bacterial enzyme, *E. coli* β-glucuronidase encoded by the gene designated gusA has optimal activity in the range of pH 6.8 to 7.7 (see, e.g., Fang et al., (1995) *Vet Microbiol* 46:361-367). β-glucuronidase has been used in plant physiology studies (Jefferson et al., (1986) *Proc Natl Acad Sci USA* 83:8447-8451; and Jefferson et al., (1987) *EMBO J* 6:3901-3907). In mammals, bacterial glucuronidase has been used as a reporter in prodrug studies, due to the very low abundance of human glucuronidase in serum (Stahl and Fishman: Beta-D-glucuronidase. In Methods in enzymatic analysis. Edited by J B, M G. Weinheim, Germany: Verlag Chemie; 1984: 246-256). Several strategies have been employed, including fusion of cancer specific antibody-fragments with beta-glucuronidase (Wang et al., (1992) *Cancer Res* 52:4484-4491), and tumor selective expression of the enzyme using bacteria (Cheng et al., (2008) *Cancer Gene Ther* 15:393-401) or adenovirus (de Graaf et al., (2004) *Human Gene Ther* 15:229-238; Huang et al., (2011) *Cancer Gene Ther* 18:381-389). The reporter gene properties of β-glucuronidase have not been studied as extensively in animals. Beta-glucuronidase has been considered as a target structure for radiotracers in positron emission tomography (Tzou et al., (2009) *Radiology* 252:754-762; Antunes et al., (2010) *Bioconjug Chem* 21:911-920). In another study, a membrane-anchored form of a mouse-glucuronidase was used in combination with the substrate fluorescein di-β-D-glucuronide (FDGlcU), which was hydrolyzed to a fluorescent reporter to assess the location and persistence of gene expression in vivo (Su et al., (2007) *Gene Ther* 14:565-574).

Bacterial glucuronidase is an advantageous reporter enzyme for methods in which body fluids such as urine and blood and serum are sampled. It has a pH-optimum range of pH 6.8 to 7.7 (Fang et al., (1995) *Vet Microbiol* 46:361-367), and has higher specific activity than human beta-glucuronidase (Chen et al., (2008) *Chem Biol* 15:1277-1286). Furthermore, the possibility to direct active beta-glucuronidase into the cytoplasm (see, e.g. Jefferson et al., (1986) *Proc Natl Acad Sci USA* 83:8447-8451), attach it to a cell surface (e.g. Huang et al., (2011) *Cancer Gene Ther* 18:381-389, Heine et al., (2001) *Gene Ther* 8:1005-1010), or secrete it from producing cells (e.g. Chen et al., (2011) *Bioconjug Chem* 22:938-948; Weyel et al., (2000) *Gene Ther* 7:224-231) offers a number of different applications.

In the methods herein, this enzyme, and/or other proteins, is detected in tissue and fluid samples distinct from the therapeutic target, to assess whether a biological therapeutic has colonized or replicated in a target tissue that is distinct from the tissue and fluid sample.

3. Method

Methods for detecting colonization and/or infection of target cells and loci by biological therapeutics and for monitoring therapy are provided. As described herein, the methods detect a product of the biological therapeutic in a locus distinct from the target of the therapeutic. Thus, for example, a body fluid, such as serum or urine or CSF or saliva, can be sampled to detect a product produced by the therapeutic in another locus. Presence of the gene product in untreated tissues and body fluids or untreated or normal tissue samples indicates that the biological therapy has colonized or infected the target loci in the treated subject. As described herein, any reporter or product of the biological therapeutic can be employed, including endogenous and heterologous reporter gene products and signals. Production of such products and their presence in non-treated tissues, cells and/or body fluids is indicative of the effectiveness of the biological therapeutic and progress of treatment. Thus, the effectiveness and progress of therapy with a biological therapeutic can be monitored.

Reporter gene products, such as enzymes, are exemplary of the gene products that can be monitored. As a non-limiting example, the activity of the enzyme beta-glucuronidase is detected by contacting a sample, such as a body fluid or tissue that does not contain treated tissue or cells, from a treated host, with a substrate for the enzyme to produce a product that is detected. The detected product is correlated with the progress or status of the therapy. For exemplary purposes, vaccinia virus (rVACV), particularly an LIVP strain or LIVP, that encodes β-glucuronidase is employed as a general marker for the preclinical and clinical evaluation of biological therapies. Tumor colonization by oncolytic rVACV results in tumor-specific expression of virus encoded proteins that are shed after successful tumor colonization and replication. Successful treatment with an oncolytic rVACV that contains a β-glucuronidase gene is assessed by detecting expression of β-glucuronidase in non-treated host cells, tissues and/or body fluids, and therefore, detection of virus mediated enzyme activity. As described herein, enzyme activity was detected in serum samples of solid tumor-bearing subjects that had been treated with rVACV, thereby, non-invasively confirming successful tumor colonization. In addition, a therapeutic effect was observed as active enzyme can only get in the serum when tumor cells are lysed and the protein is released, or shed.

Thus, provided herein is a method for monitoring biological therapies by detection of reporter protein in non-treated samples or non-treated loci in treated subjects. In the methods, a subject is treated with a biological therapeutic. In some instances, the biological therapeutic encodes a reporter protein and optionally one or more additional heterologous or exogenous gene products. Any reporter protein can be used in the methods provided herein. In some examples, the reporter protein is an enzymatic reporter protein. Following or during treatment with the biological therapeutic, a sample is collected from the subject and a product encoded by the therapeutic is detected. If, for example, the product is an enzyme, the sample is contacted with a substrate, and the resulting product is detected. Following incubation of the sample and the substrate, the sample is monitored to detect the encoded reporter protein or a signal induced by the reporter protein. Detection of the reporter protein indicates that the biological therapeutic is replicating in or colonizing a target locus. Thus, detection of expression of proteins introduced by the biological therapy in loci distinct from the treatment's target is indicative of effective biological therapy.

In a particular example herein, a substrate that is activated by β-glucuronidase is added to a biological sample, for example, blood, e.g., serum, or urine, taken from a subject treated, such as by I.V. administration, with any GusA-encoding therapeutic, including, but not limited to GusA-encoding viral vectors, such as GusA-encoding vaccinia vectors, e.g., GusA-rVACV, GusA-expressing bacteria or any other GusA-encoding vector for heterologous gene expression. After a pre-determined reaction time, the sample is analyzed for GusA activated substrate. The method allows for direct diagnosis of viral tumor colonization in tumor bearing patients.

As exemplified herein, oncolytic vaccinia strains (rVACV) strains that encode a bacterial beta-glucuronidase were administered to tumor-bearing subjects. Body fluid samples were obtained and mixed with fluorogenic probe. As demonstrated herein, the use of fluorogenic probes that are specifically activated by β-glucuronidase resulted in 1) preferential activation in tumors; 2) renal excretion of the activated fluorescent compounds; and 3) reproducible detection of β-glucuronidase in the serum of oncolytic vaccinia virus treated, tumor bearing mice in several tumor models. Time course studies demonstrate reliable differentiation between tumor bearing and healthy mice is possible as early as 9 days post injection of the virus.

Further, the described method's sensitivity was demonstrated in that a single infected tumor cell was reliably detected using the assay. Thus, it was determined that as few as or about $2.4 \times 10^4$ vaccinia virus infected cancer cells are detectable in a human subject using the provided method. With a diameter of 50 μm/cell, this number corresponds to a tumor volume of only 1.6 mm$^3$. In human subjects, for example, even if not all virus infected cells release all of their enzyme product into the blood stream, e.g., serum, upon lysis, such that the number of infected cells is 10 or even 100-fold higher than detected, the tumor diameter necessary for positive detection using the methods provided herein is as small as 3.1 and 6.7 mm$^3$, respectively. Thus, the methods herein can detect tumors as small as about 1-3 mm$^3$, even assuming that only a fraction of the infected/colonized tumor cells release product.

For example, serum was obtained from tumor- and non-tumor bearing mice, to which a GusA-rVACV (a recombinant vaccinia virus containing the GusA gene) or controls that were either mock or control-rVACV (vaccinia virus not encoding GusA) were administered. Subsequently, the serum was used to assess enzyme activity by GusA-activatable fluorescent compounds (namely FDGlcU and 4-MUG). Both compounds were shown to be specifically activated in GusA-rVACV-injected tumor bearing mice but not in control rVACV-injected mice.

Further, as described herein, using *E. coli* Nissle 1917 to produce products for fluorescent compound activation, e.g., FDGlcU or 4-MUG activation, fluorescent activation was observed in serum derived from tumor bearing mice that were injected with *E. coli* Nissle 1917×pBR322DESTinv-PS10-gusA-luxABCDE (-SgusAL) but not in serum derived from mice that were either mock or *E. coli* Nissle 1917× pBR322DESTinv-PS10-luxABCDE-term (-SLT) injected mice.

Thus, it has been demonstrated that a reporter product, such beta-glucuronidase in combination with fluorogenic substrates cannot only be used for localization of enzyme expression, but also as a general biomarker for foreign protein expression in serum samples. Consequently, the described method can be applied to any biological therapeutic.

C. Methods for Detecting Replication or Colonization of a Biological Therapeutic Provided herein is a method for detecting replication or colonization of a biological therapy or biological therapeutic. Biological therapies include, but are not limited to, cell therapy, gene therapy, immunotherapy, adoptive immunotherapy, viral therapy and bacterial therapy. Thus, the provided method can be used to determine gene expression of a gene encoded by the therapeutic and/or tumor colonization of an immunoprivileged cell. Hence, the method provided herein can be used, for example, to determine the presence of a tumor or tumor cells, such as circulating tumor cells and metastasizing cells, tumor colonization by an oncolytic viral therapy, or expression of a gene introduced by gene therapy or cell therapy.

Provided herein is a method for detecting replication or colonization of a target locus in a subject by a biological therapeutic. A sample is obtained from a subject to whom the therapeutic is administered from a locus in the subject other than a target of the biological therapeutic and the sample is tested to detect a protein encoded by the biological therapeutic. Detection of the protein indicates that the biological therapeutic is replicating or colonizing the target locus. The protein encoded by the biological therapeutic appears in biological tissues and fluids because of replication and colonization by the biological therapeutic, that is, the protein is shed. The provided method involves: 1) treating a subject with a biological therapeutic; 2) collecting a sample from the subject to whom the biological therapeutic was administered from a locus other than the target locus or collecting a sample that is not targeted tissue; and 3) detecting the presence of a protein encoded by the biological therapeutic in the sample, thereby determining the status or progress of therapy by the biological therapeutic. If, for example, the biological therapeutic encodes an enzyme, a substrate for the enzyme is added to the sample under conditions appropriate for enzymatic activity, and the converted substrate (product) is detected either by its detection or detecting a signal produced by the reaction of the enzyme and substrate. Detection of the signal or protein product is indicative of gene expression of a protein encoded by the therapeutic, thereby indicating infection of a cell or colonization of the subject by the biological therapeutic. For example, if the therapeutic is an oncolytic virus, detection of a viral-encoded protein in a body fluid sample is indicative of infection of tumor cells, including circulating tumor cells (or other cells in which such viruses accumulate).

Treatment with the biological therapeutic can be monitored once or periodically or intermittently and before, during or after treatment. Monitoring the production of such protein during treatment is indicative of the progress of therapy. Therapy can be monitored over time to indicate the progress of the therapy. For example, the biological therapeutic can be monitored shortly after treatment, wherein enzyme detection indicates viral replication. Over time, the treatment with the biological therapeutic can be monitored to detect, for example, tumor shrinkage, wherein less enzyme is detected as the tumor volume decreases, due to a decrease in shed reporter enzyme.

The biological therapeutic can be administered by any method known to one of skill in the art. In one example, the biological therapeutic can be administered systemically. In another example, the biological therapeutic is administered topically, locally, enterally or parenterally. For example, the biological therapeutic is administered topically, such as epicutaneously (onto the skin) or intranasally, enterally, such as orally, by gastric feeding tube, duodenal feeding tube, or gastrostomy, or rectally, parenterally, such as intravenously, intraarterially, intramuscularly, intracardiacly, subcutaneously, by intraosseous infusion (into the bone marrow), intradermally, intraperitoneally, intrapleurally, transdermally, transmucosally, or by other administration including epidurally, intrathecally, intraventricularly or intratumorally.

Also provided herein is a method for rapidly diagnosing bacteria involved in infection, for example, bacteria involved in sepsis and bladder or urinary tract infections. In the provided method, β-glucuronidase is detected in a sample from a subject suspected of having an infection. A sample is obtained, a substrate for β-glucuronidase is added, and a signal induced by the β-glucuronidase is detected. Positive detection of β-glucuronidase activity indicates an *Escherichia*, *Shigella* and *Salmonella* infection due to the fact that β-glucuronidase activity only occurs in bacteria of the genera

*Escherichia, Shigella* and *Salmonella* (Kilian and Bulow (1976) *Acta Pathol Microbiol Scand B.* 84B(5):245-251). Thus, using the described method, one can analyze, for example, blood or urine samples using a β-glucuronidase substrate and rapidly determine if the infection is from *E. coli*, for example, as opposed to a different bacteria, such as *Staphylococcus*. Positive detection of an infection allows treatment with an antibiotic appropriate specific to the identified infection before the bacterial strain can be identified via PCR (currently in clinical tests) or culture.

The following sections describe exemplary biological therapeutics that can be monitored using the methods provided herein, including viruses, bacteria, cell therapies and gene therapies. Also described are reporter proteins and substrates, samples and detection methods for use in practicing the methods.

1. Biological Therapeutics

The methods provided herein allow for detection of replication or colonization of a biological therapeutic in a subject. Any biological therapeutic can be used in the methods provided. In some examples, the biological therapeutic contains a vector that encodes or is modified to encode a reporter protein. The vector can be an eukaryotic or prokaryotic vector, such as a viral vector, mammalian vector, bacterial vector, plant vector or insect vector. In some examples, the reporter protein is encoded by an artificial chromosome. Typically, the biological therapeutic is a virus or viral vector, bacterium, gene therapy vector or nucleic acid for gene therapy, cells for immunotherapy and/or adoptive immunotherapy, autologous cell therapy or cell therapy. Thus, biological therapeutics for use in the methods provided herein include, for example, viruses, e.g. oncolytic viruses, bacteria, e.g. *E. coli* strain Nissle 1917, gene therapy, immunotherapy or adoptive immunotherapy, and cell therapy. The biological therapeutics provided herein can be used to treat diseases and disorders, such as cancer, genetic disorders, and immune disorders.

a. Viruses

The biological therapy for use in the methods provided herein can be a virus, typically an oncolytic virus for use in oncolytic viral therapy. While the protein for detection can be an endogenous protein, the viruses optionally contain heterologous nucleic acid encoding a reporter protein, e.g., an enzyme, and optionally additionally contain one more additional heterologous nucleic acid sequences for the expression of additional heterologous genes. The heterologous nucleic acid is typically operably linked to a regulatory sequences, including a suitable promoter for expression of the heterologous nucleic acid in the infected cells. Expression can be constitutive or inducible.

Viruses whose therapies can be monitored include oncolytic viruses, including viruses that accumulate in tumor cells and viruses modified to do so, and viruses for delivery of gene therapy products either by accumulation in target cells or provided in the infected cell. Viruses and viral vectors include, but are not limited to, poxviruses, herpesviruses, adenoviruses, adeno-associated viruses, lentiviruses, retroviruses, rhabdoviruses, papillomaviruses, vesicular stomatitis virus, measles virus, Newcastle disease virus, picornavirus, sindbis virus, papillomavirus, parvovirus, reovirus, coxsackievirus, influenza virus, mumps virus, poliovirus, and semliki forest virus. Typically, the virus is a cytoplasmic virus which does not require entry of viral nucleic acid molecules into the nucleus of the host cell during the viral life cycle. A variety of cytoplasmic viruses are known, including, but not limited to, poxviruses, African swine flu family viruses, and various RNA viruses such as picornaviruses, caliciviruses, togaviruses, coronaviruses and rhabdoviruses. Exemplary cytoplasmic viruses provided herein are viruses of the poxvirus family, including orthopoxviruses. Exemplary of poxviruses are vaccinia viruses.

i. Poxviruses

In some examples, the therapeutic virus is from the poxvirus family. Poxviruses include Chordopoxyiridae, such as orthopoxvirus, parapoxvirus, avipoxvirus, capripoxvirus, leporipoxvirus, suipoxvirus, molluscipoxvirus and yatapoxvirus, as well as Entomopoxyirinae such as entomopoxvirus A, entomopoxvirus B, and entomopoxvirus C. One skilled in the art can select a particular genera or individual chordopoxyiridae according to the known properties of the genera or individual virus, and according to the selected characteristics of the virus (e.g., pathogenicity, ability to elicit an immune response, preferential tumor localization), the intended use of the virus, the tumor type and the host organism. Exemplary chordopoxyiridae genera are orthopoxvirus and avipoxvirus. Avipoxviruses infect a variety of different birds and have been administered to humans. Exemplary avipoxviruses include canarypox, fowlpox, juncopox, mynahpox, pigeonpox, psittacinepox, quailpox, peacockpox, penguinpox, sparrowpox, starlingpox, and turkeypox viruses.

Orthopoxviruses infect a variety of different mammals including rodents, domesticated animals, primates and humans. Several orthopoxviruses have a broad host range, while others have narrower host range. Exemplary orthopoxviruses include buffalopox, camelpox, cowpox, ectromelia, monkeypox, raccoon pox, skunk pox, tatera pox, uasin gishu, vaccinia, variola, and volepox viruses. In some embodiments, the orthopoxvirus selected can be an orthopoxvirus known to infect humans, such as cowpox, monkeypox, vaccinia, or variola virus. Optionally, the orthopoxvirus known to infect humans can be selected from among orthopoxviruses with a broad host range, such as cowpox, monkeypox, and vaccinia virus.

(1) Vaccinia Viruses

One exemplary orthopoxvirus for therapy that can be monitored and detected by the methods provided herein is vaccinia virus. Vaccinia is a cytoplasmic virus, thus, it does not insert its genome into the host genome during its life cycle. The linear dsDNA viral genome of vaccinia virus is approximately 200 kb in size, encoding a total of approximately 200 genes. A variety of vaccinia virus strains are available for therapy and/or diagnostics. These include, but are not limited to strains of or derived from, Western Reserve (WR) (SEQ ID NO:104), Copenhagen (SEQ ID NO:105), Tashkent, Tian Tan, Lister, Wyeth, IHD-J, and IHD-W, Brighton, Ankara, MVA, Dairen I, LIPV, LC16M8, LC16MO, LIVP, WR 65-16, Connaught, New York City Board of Health strains. Exemplary vaccinia viruses are Lister, particularly LIVP, vaccinia viruses. In one embodiment, the Lister strain can be an attenuated Lister strain, such as the LIVP (Lister virus from the Institute of Viral Preparations, Moscow, Russia) strain, which was produced by further attenuation of the Lister strain. The LIVP strain was used for vaccination throughout the world, particularly in India and Russia, and is widely available. In another embodiment, the viruses and methods provided herein can be based on modifications to the Lister strain of vaccinia virus.

Lister (also referred to as Elstree) vaccinia virus is available from any of a variety of sources. For example, the Elstree vaccinia virus is available at the ATCC under Accession Number VR-1549. The Lister vaccinia strain has high transduction efficiency in tumor cells with high levels of gene expression. LIVP and its production are described in U.S. Pat. Nos. 7,588, 767, 7,588,771, 7,662,398 and 7,754,221 and U.S. Patent Publication Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650 and SEQ ID NOS:82-91.

Vaccinia virus, particularly strains modified or identified as having reduced toxicity, possesses a variety of features advantageous in cancer gene therapy and vaccination including broad host and cell type range, a large carrying capacity for foreign genes (up to 25 kb of exogenous DNA fragments (approximately 12% of the vaccinia genome size) can be inserted into the vaccinia genome), high sequence homology among different strains for designing and generating modified viruses in other strains, and techniques for production of modified vaccinia strains by genetic engineering are well established (Moss (1993) Curr. Opin. Genet. Dev. 3: 86-90; Broder and Earl (1999) Mol. Biotechnol. 13: 223-245; Timiryasova et al. (2001) Biotechniques 31: 534-540). A variety of vaccinia virus strains are available, including Western Reserve (WR), Copenhagen, Tashkent, Tian Tan, Lister, Wyeth, IHD-J, and H-ID-W, Brighton, Ankara, MVA, Dairen I, LIPV, LC16M8, LC16MO, LIVP, WR 65-16, Connaught, New York City Board of Health. Exemplary therapeutic vaccinia viruses include, but are not limited to, Lister strain or LIVP strain of vaccinia viruses.

LIVP strains that can be used in the methods provided herein include LIVP clonal strains derived from LIVP that have a genome that is or is derived from or is related to a the parental sequence set forth in SEQ ID NO:91 (see U.S. patent application Ser. No. 13/506,369 which is incorporated herein by reference). These include the strain designed vaccinia viruses GLV-1h68 and all strains and modified forms thereof (see, e.g., U.S. Pat. Nos. 7,588,767, 7,588,771, 7,662,398, 7,754,221, 8,021,662, 8,052,962 and 8,066,984 and U.S. Patent Publication Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650). These also include LIVP clonal strains that have been shown to exhibit greater anti-tumorigenicity and/or reduced toxicity compared to the recombinant or modified virus strain designated GLV-1h68 (having a genome set forth in SEQ ID NO:90; and U.S. patent application Ser. No. 13/506,369). In particular, the clonal strains are present in a virus preparation propagated from LIVP.

The LIVP and clonal strains for use in the methods provided herein have a sequence of nucleotides that have at least 70%, such as at least 75%, 80%, 85% or 90% sequence identity to SEQ ID NO:91. For example, the clonal strains have a sequence of nucleotides that is at or at least 91%, 92%, 93%, 94%, 95%, 95%, 97%, 98%, 99%, 99.1%, 99.2%, 99.3%, 99.4%, 99.5%, 99.6%, 99.7%, 99.8%, 99.9%, or 100% identical to SEQ ID NO:91. Such LIVP clonal viruses include viruses that differ in one or more open reading frames (ORF) compared to the parental LIVP strain that has a sequence of nucleotides set forth in SEQ ID NO:91. The LIVP clonal virus strains provided herein can contain a nucleotide deletion or mutation in any one or more nucleotides in any ORF compared to SEQ ID NO:91, or can contain an addition or insertion of viral DNA compared to SEQ ID NO:91.

(2) Modified Vaccinia Viruses

Exemplary for use as therapeutics in the methods herein include vaccinia viruses with insertions, mutations or deletions. Exemplary insertions, mutations or deletions include those that result in an attenuated vaccinia virus relative to the wild type strain. For example, vaccinia virus insertions, mutations or deletions can decrease pathogenicity of the vaccinia virus, for example, by reducing the toxicity, reducing the infectivity, reducing the ability to replicate, or reducing the number of non-tumor organs or tissues to which the vaccinia virus can accumulate. Other exemplary insertions, mutations or deletions include, but are not limited to, those that increase antigenicity of the virus, those that permit detection, monitoring, or imaging, those that alter attenuation of the virus, and those that alter infectivity. For example, the ability of vaccinia viruses provided herein to infect and replicate within tumors can be enhanced by mutations that increase the extracellular enveloped form of the virus (EEV) that is released from the host cell. Modifications can be made, for example, in genes that are involved in nucleotide metabolism, host interactions and virus formation or at other nonessential gene loci. Any of a variety of insertions, mutations or deletions of the vaccinia virus known in the art can be used herein, including insertions, mutations or deletions of: the thymidine kinase (TK) gene, the hemagglutinin (HA) gene, and F14.5L gene, among others (e.g., E2L/E3L, K1L/K2L, superoxide dismutase locus, 7.5K, C7-K1L, J2R, B13R+B14R, A56R, A26L or 14L gene loci). The vaccinia viruses for use in the methods provided herein also can contain two or more insertions, mutations or deletions. Thus, included are vaccinia viruses containing two or more insertions, mutations or deletions of the loci provided herein or other loci known in the art. The viruses can be based on modifications to the Lister strain and/or LIVP strain of vaccinia virus. Any known vaccinia virus modification, or modifications that correspond to those provided herein or known to those of skill in the art to reduce toxicity of a vaccinia virus, can be included a modified vaccinia virus used in the methods herein. Generally, however, the mutation will be a multiple mutant and the virus will be further selected to reduce toxicity.

The modified viruses for use in the methods provided herein can encode heterologous gene products. The heterologous nucleic acid is typically operably linked to a promoter for expression of the heterologous gene in the infected cells. Suitable promoter include viral promoters, such as a vaccinia virus natural and synthetic promoters. Exemplary vaccinia viral promoters include, but are not limited to, P11k, P7.5k early/late, P7.5k early, P28 late, synthetic early $P_{SE}$, synthetic early/late $P_{SEL}$ and synthetic late $P_{SL}$ promoters.

The viruses can express one or more genes whose products are useful for tumor therapy. For example, a virus can express proteins that cause cell death or whose products cause an anti-tumor immune response. Such genes can be considered therapeutic genes. A variety of therapeutic gene products, such as toxic or apoptotic proteins, or siRNA, are known in the art, and can be used with the viruses provided for use as biological therapeutics herein. The therapeutic genes can act by directly killing the host cell, for example, as a channel-forming or other lytic protein, or by triggering apoptosis, or by inhibiting essential cellular processes, or by triggering an immune response against the cell, or by interacting with a compound that has a similar effect, for example, by converting a less active compound to a cytotoxic compound. Exemplary proteins useful for tumor therapy include, but are not limited to, tumor suppressors, toxins, cytostatic proteins, antiangiogenic proteins, antitumor antibodies, and costimulatory molecules, such as cytokines and chemokines among others provided elsewhere herein and known in the art. The viruses used in the methods provided herein also can be effective against tumors without the introduction of additional exogenous therapeutic genes.

The viruses used in the methods provided herein can express one or more additional genes whose products are useful for tumor detection and/or imaging. Exemplary gene products for imaging or detection include detectable proteins or proteins that induce detectable signals. Exemplary of detectable proteins or proteins that induce detectable signals are proteins, such as luciferases, fluorescent proteins, receptors that can bind imaging agents, or proteins linked to imaging or diagnostic moieties. The viruses used as therapeutic proteins in the methods provided herein also can encode proteins, such as transporter proteins (e.g., the human norepinephrine transporter (hNET) or the human sodium iodide symporter (hNIS)), which can provide increase uptake of diagnostic and therapeutic moieties across the cell membrane of infected cells for therapy, imaging or detection.

Imaging or diagnostic moieties include those that can emit a signal that is detectable by optical or non-optical imaging methods. Detection of the signal by imaging modalities such as, for example, by positron emission tomography (PET) and, thereby allows visualization of the infected tissues, such as a tumor or an inflammation.

One skilled in the art can select a virus for use as a biological therapeutic herein from any of a variety of viruses, according to a variety of factors, including, but not limited to, the intended use of the virus, such as a diagnostic and/or therapeutic use (e.g., tumor therapy or diagnosis, vaccination, antibody production, or heterologous protein production), the host organism, and the type of tumor. An oncolytic virus for use in the methods provided herein can exhibit one or more desired characteristics for use as a therapeutic agent, such as, for example attenuated pathogenicity, reduced toxicity, preferential accumulation in immunoprivileged cells and tissues, such as tumor, ability to activate an immune response against tumor cells, immunogenic, replication competent, and ability to express exogenous proteins, and combinations thereof (3) Exemplary Modified Vaccinia Viruses Exemplary therapeutic vaccinia viruses include those derived from vaccinia virus strain GLV-1h68 (also named RVGL21, SEQ ID NO:90), which has been described in U.S. Pat. Pub. No. 2005-0031643 and U.S. Pat. No. 7,588,767 which are incorporated herein by reference in their entirety. GLV-1h68 contains DNA insertions gene loci of the vaccinia virus LIVP strain (SEQ ID NO: 91, a vaccinia virus strain, originally derived by adapting the Lister strain (ATCC Catalog No. VR-1549) to calf skin (Institute of Viral Preparations, Moscow, Russia, Al'tshtein et al., (1983) Dokl. Akad. Nauk USSR 285:696-699)). GLV-1h68 contains expression cassettes encoding detectable marker proteins in the F14.5L (also designated in LIVP as F3), thymidine kinase (TK) and hemagglutinin (HA) gene loci. An expression cassette containing a Ruc-GFP cDNA molecule (a fusion of DNA encoding *Renilla* luciferase and DNA encoding GFP) under the control of a vaccinia synthetic early/late promoter $P_{SEL}$ (($P_{SEL}$)RUC-GFP) is inserted into the F14.5L gene locus; an expression cassette containing a DNA molecule encoding beta-galactosidase under the control of the vaccinia early/late promoter $P_{7.5k}$ (($P_{7.5k}$)LacZ) and DNA encoding a rat transferrin receptor positioned in the reverse orientation for transcription relative to the vaccinia synthetic early/late promoter $P_{SEL}$ (($P_{SEL}$)rTrfR) is inserted into the TK gene locus (the resulting virus does not express transferrin receptor protein since the DNA molecule encoding the protein is positioned in the reverse orientation for transcription relative to the promoter in the cassette); and an expression cassette containing a DNA molecule encoding β-glucuronidase under the control of the vaccinia late promoter $P_{11k}$(($P_{11k}$)gusA) is inserted into the HA gene locus. The GLV-1h68 virus exhibits a strong preference for accumulation in tumor tissues as compared to non-tumorous tissues following systemic administration of the virus to tumor bearing subjects. This preference is significantly higher than the tumor selective accumulation of other vaccinia viral strains, such as WR (see, e.g. U.S. Pat. Pub. No. 2005-0031643 and Zhang et al. (2007) *Cancer Res.* 67(20): 10038-10046). Modified viruses for use in the methods provided herein can be derived from GLV-1h68. Exemplary viruses are generated by replacement of one or more expression cassettes of the GLV-1h68 strain with heterologous DNA encoding gene products for therapy and/or imaging.

Non-limiting examples of viruses that are derived from attenuated LIVP viruses, such as GLV-1h68, and that are therapeutic viruses for which therapy can monitored, include, but are not limited to, LIVP viruses described in U.S. Pat. Nos. 7,588,767, 7,588,771, 7,662,398 and 7,754,221 and U.S. Patent Publication Nos. 2007/0202572, 2007/0212727, 2010/0062016, 2009/0098529, 2009/0053244, 2009/0155287, 2009/0117034, 2010/0233078, 2009/0162288, 2010/0196325 and 2009/0136917, which are incorporated herein by reference in their entirety. For example, the vaccinia virus can be selected from among GLV-1h22, GLV-1h68, GLV-1i69 (SEQ ID NO:84), GLV-1h70, GLV-1h71, GLV-1h72, GLV-1h73, GLV-1h74, GLV-1h81, GLV-1h82, GLV-1h83, GLV-1h84, GLV-1h85, or GLV-1h86, which are described in U.S. Patent Publication No. 2009/0098529 and GLV-1h104, GLV-1h105, GLV-1h106, GLV-1h107, GLV-1h108 and GLV-1h109, which are described in U.S. Patent Publication No. 2009/0053244; GLV-1h99, GLV-1h100, GLV-1h101, GLV-1h139, GLV-1h146, GLV-1h151, GLV-1h152 and GLV-1h153, which are described in U.S. Patent Publication No. 2009/0117034.

Exemplary of viruses which have one or more expression cassettes removed from GLV-1h68 and replaced with a heterologous non-coding DNA molecule include GLV-1h70, GLV-1h71, GLV-1h72, GLV-1h73, GLV-1h74, GLV-1h85, and GLV-1h86. GLV-1h70 contains ($P_{SEL}$)Ruc-GFP inserted into the F14.5L gene locus, ($P_{SEL}$)rTrfR and ($P_{7.5k}$)LacZ inserted into the TK gene locus, and a non-coding DNA molecule inserted into the HA gene locus in place of ($P_{11k}$)gusA. GLV-1h71 contains a non-coding DNA molecule inserted into the F14.5L gene locus in place of ($P_{SEL}$)Ruc-GFP, ($P_{SEL}$)rTrfR and ($P_{7.5k}$)LacZ inserted into the TK gene locus, and ($P_{11k}$)gusA inserted into the HA gene locus. GLV-1h72 contains ($P_{SEL}$)Ruc-GFP inserted into the F14.5L gene locus, a non-coding DNA molecule inserted into the TK gene locus in place of ($P_{SEL}$)rTrfR and ($P_{7.5k}$)LacZ, and $P_{11k}$gusA inserted into the HA gene locus. GLV-1h73 contains a non-coding DNA molecule inserted into the F14.5L gene locus in place of ($P_{SEL}$)Ruc-GFP, ($P_{SEL}$)rTrfR and ($P_{7.5k}$)LacZ inserted into the TK gene locus, and a non-coding DNA molecule inserted into the HA gene locus in place of ($P_{11k}$)gusA. GLV-1h74 contains a non-coding DNA molecule inserted into the F14.5L gene locus in place of ($P_{SEL}$)Ruc-GFP, a non-coding DNA molecule inserted into the TK gene locus in place of ($P_{SEL}$)rTrfR and ($P_{7.5k}$)LacZ, and a non-coding DNA molecule inserted into the HA gene locus in place of ($P_{11k}$)gusA. GLV-1h85 contains a non-coding DNA molecule inserted into the F14.5L gene locus in place of ($P_{SEL}$)Ruc-GFP, a non-coding DNA molecule inserted into the TK gene locus in place of ($P_{SEL}$)rTrfR and ($P_{7.5k}$)LacZ, and ($P_{11k}$)gusA inserted into the HA gene locus. GLV-1h86 contains ($P_{SEL}$)Ruc-GFP inserted into the F14.5L gene locus, a non-coding DNA molecule inserted into the TK gene locus in place of ($P_{SEL}$)rTrfR and ($P_{7.5k}$)LacZ, and a non-coding DNA molecule inserted into the HA gene locus in place of ($P_{11k}$)gusA.

Other exemplary viruses include, but are not limited to, LIVP viruses that express one or more therapeutic gene products, such as angiogenesis inhibitors (e.g., GLV-1h81, which contains DNA encoding the plasminogen K5 domain under the control of the vaccinia synthetic early-late promoter in place of the gusA expression cassette at the HA locus in GLV-1h68; GLV-1h104, GLV-1h105 and GLV-1h106, which contain DNA encoding a truncated human tissue factor fused to the $\alpha_v\beta_3$-integrin RGD binding motif (tTF-RGD) under the control of a vaccinia synthetic early promoter, vaccinia synthetic early/late promoter or vaccinia synthetic late promoter, respectively, in place of the LacZ/rTFr expression cassette at the TK locus of GLV-1h68; GLV-1h107, GLV-1h108 and GLV-1h109, which contain DNA encoding an anti-VEGF single chain antibody G6 under the control of a vaccinia synthetic early promoter, vaccinia synthetic early/late promoter or vaccinia synthetic late promoter, respectively, in place of the LacZ/rTFr expression cassette at the TK locus of GLV-1h68) and proteins for tumor growth suppression (e.g., GLV-1h90, GLV-1h91 and GLV-1h92, which express a fusion protein containing an IL-6 fused to an IL-6 receptor (sIL-6R/IL-6) under the control of a vaccinia synthetic early promoter, vaccinia synthetic early/late promoter or vaccinia synthetic late promoter, respectively, in place of the gusA expression cassette at the HA locus in GLV-1h68; and GLV-1h96, GLV-1h97 and GLV-1h98, which express IL-24 (melanoma differentiation gene, mda-7) under the control of a vaccinia synthetic early promoter, vaccinia synthetic early/late promoter or vaccinia synthetic late promoter, respectively, in place of the Ruc-GFP fusion gene expression cassette at the F14.5L locus of GLV-1h68). Additional therapeutic gene products that can be engineered in the viruses provided herein also are described elsewhere herein.

Exemplary transporter proteins that can be encoded by the viruses provided herein include, for example, the human norepinephrine transporter (hNET) and the human sodium iodide symporter (hNIS). Exemplary viruses that can be employed in the methods and use provided herein that encode the human norepinephrine transporter (hNET) include, but are not limited to, GLV-1h99, GLV-1h100, GLV-1h101, GLV-1h139, GLV-1h146, and GLV-1h150. GLV-1h99 encodes hNET under the control of a vaccinia synthetic early promoter in place of the Ruc-GFP fusion gene expression cassette at the F14.5L locus of GLV-1h68. GLV-1h100 and GLV-1h101 encode hNET under the control of a vaccinia synthetic early promoter or vaccinia synthetic late promoter, respectively, in place of the LacZ/rTFr expression cassette at the TK locus of GLV-1h68. GLV-1h139 encodes hNET under the control of a vaccinia synthetic early promoter in place of the gusA expression cassette at the HA locus in GLV-1h68. GLV-1h146 and GLV-1h150, encode hNET under the control of a vaccinia synthetic early promoter or vaccinia synthetic late promoter, respectively, in place of the LacZ/rTFr expression cassette at the TK locus of GLV-1h100 and GLV-101, respectively. Thus, GLV-1h146 and GLV-1h150 encode both hNET and IL-24. Exemplary viruses that can be employed in the methods and use provided herein that encode the human sodium iodide transporter (hNIS) include, but are not limited to, GLV-1h151, GLV-1h152 and GLV-1h153. GLV-1h151, GLV-1h152 and GLV-1h153 encode hNIS under the control of a vaccinia synthetic early promoter, vaccinia synthetic early/late promoter or vaccinia synthetic late promoter, respectively, in place of the gusA expression cassette at the HA locus in GLV-1h68.

Other exemplary viruses include, but are not limited to, LIVP viruses that encode additional imaging agents such as ferritin and/or a transferrin receptor (e.g., GLV-1h82 and GLV-1h83 which encode *E. coli* ferritin at the HA locus; GLV-1h82 addition encodes the human transferrin receptor at the TK locus) or a click beetle luciferase-red fluorescent protein fusion protein (e.g., GLV-1h84, which encodes CBG99 and mRFP1 at the TK locus). During translation, the two proteins are cleaved into two individual proteins at picornavirus 2A element (Osborn et al., (2005) *Mol. Ther.* 12: 569-574). CBG99 produces a more stable luminescent signal than does *Renilla* luciferase with a half-life of greater than 30 minutes, which makes both in vitro and in vivo assays more convenient. mRFP1 provides improvements in in vivo imaging relative to GFP since mRFP1 can penetrate tissue deeper than GFP.

ii. Other Cytoplasmic Viruses

Other therapeutic viruses whose therapy can be detected and monitored as described herein include cytoplasmic viruses that are not poxviruses. A variety of such cytoplasmic viruses are known in the art, and include African swine flu family viruses and various RNA viruses such as arenaviruses, picornaviruses, caliciviruses, togaviruses, coronaviruses, paramyxoviruses, flaviviruses, reoviruses, and rhaboviruses. Exemplary togaviruses include Sindbis viruses. Exemplary arenaviruses include lymphocytic choriomeningitis virus. Exemplary rhaboviruses include vesicular stomatitis viruses. Exemplary paramyxoviruses include Newcastle Disease viruses and measles viruses. Exemplary picornaviruses include polio viruses, bovine enteroviruses and rhinoviruses. Exemplary flaviviruses include Yellow fever virus; attenuated Yellow fever viruses are known in the art, as exemplified in Barrett et al. (*Biologicals* 25: 17-25 (1997)), and McAllister et al. (*J. Virol.* 74: 9197-9205 (2000)).

Also provided for use as a biological therapeutic herein are modified viruses that have one or more enhanced characteristics relative to the wild type virus. Such characteristics can include, but are not limited to, attenuated pathogenicity, reduced toxicity, preferential accumulation in tumor, increased ability to activate an immune response against tumor cells, increased immunogenicity, increased or decreased replication competence, and are able to express exogenous proteins, and combinations thereof. In some embodiments, the modified viruses have an ability to activate an immune response against tumor cells without aggressively killing the tumor cells. In other embodiments, the viruses can be modified to express one or more detectable genes, including genes that can be used for imaging. In other embodiments, the viruses can be modified to express one or more genes for harvesting the gene products and/or for harvesting antibodies against the gene products.

iii. Adenovirus, Herpes, Retroviruses

Other viruses for use as a biological therapeutic in the methods herein include viruses that include in their life cycle entry of a nucleic acid molecule into the nucleus of the host cell. A variety of such viruses is known in the art, and includes herpesviruses, papovaviruses, retroviruses, adenoviruses, parvoviruses and orthomyxoviruses. Exemplary herpesviruses include herpes simplex type 1 viruses, cytomegaloviruses, and Epstein-Barr viruses. Exemplary papovaviruses include human papillomavirus and SV40 viruses. Exemplary retroviruses include lentiviruses. These viruses have been employed in a variety of gene therapy can be cell-based therapeutic methods. Exemplary orthomyxoviruses include influenza viruses. Exemplary parvoviruses include adeno associated viruses. Adenoviruses have been employed for cell therapy. In addition, adenoviruses, such as the onyx viruses and others, have been modified, such as by deletion of EA1 genes, so that they replicate in cancerous cells, and, thus, are oncolytic. Adenoviruses also have been engineered to have modified tropism for tumor therapy and also as gene therapy vectors. Oncolytic viruses for use as a biological therapeutic in the methods provided herein are well known to one skill in the art and include, for example, vesicular stomatitis virus, see, e.g., U.S. Pat. Nos. 7,731,974, 7,153,510, 6,653,103 and U.S. Pat. Pub. Nos. 2010/0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos. 2011/0177032, 2011/0158948, 2010/0092515, 2009/0274728, 2009/0285860, 2009/0215147, 2009/0010889, 2007/0110720, 2006/0039894 and 20040009604; retroviruses, see, e.g., U.S. Pat. Nos. 6,689,871, 6,635,472, 5,851,529, 5,716,826, 5,716,613 and U.S. Pat. Pub. No. 20110212530; and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

b. Bacteria

The biological therapy monitored in the methods herein can be bacteria, such as an attenuated or non-pathogenic bacterium, that accumulates at sites of cellular proliferation, including tumors, tumor tissues, metastases, areas of inflammation, immunoprivileged sites or tissues, wounds and/or infections (see, e.g., U.S. Pat. Nos. 7,763,420, 7,820,184, 7,514,089, 7,452,531, 7,354,592, 6,962,696, 6,923,972, 6,863,894, 6,685,935, 6,475,482, 7,687,474, 7,255,851 and 6,638,752; U.S. Pat. Publ. Nos. 2003/0059400, 2004/0234455, 2005/0069491, 2009/0117049, 2009/0117048, 2009/0117047, 2009/0123382, 2003/0228261, 2004/0213741, 2005/0249670, 2011/0223241, 2010/0136048, 2009/0169517, 2008/0124355 and 2007/0009489; and Pawelek et al., (2003) *Lancet Oncol* 4:548-556, King et al., (2002) *Hum Gene Ther* 13:1225-1233, Soghomonyan et al., (2005) *Cancer Gene Ther* 12:101-108, Friedlos et al., (2008) *Clin Cancer Res* 14:4259-4266, King et al., (2009) *Methods Mol Biol* 542:649-659, Kapoor et al., (2011) *Antimicrob Agents Chemother* 55:3058-3062, Barak et al., (2010) *BMC Cancer* 10:146, and Contag (2007) *Annu Rev Pathol* 2:277-305. Thus, the bacteria are used to treat diseases and disorders, including, for example, proliferative conditions, neoplastic diseases, tumors, tumor tissue, cancer, metastasis, inflammation, wounds and infections. The bacterium used in the methods provided herein can be modified to express the reporter protein, e.g., reporter enzyme, and additionally can be modified to contain one or more additional exogenous genes. In some examples, the bacterium is modified to contain one or more regulatory sequences to regulate expression of an exogenous gene.

Generally, the therapeutic bacteria monitored in the methods herein are attenuated or non-pathogenic, and they generally replicate in the host or target tissue. Bacteria include mutual, commensal and/or probiotic strains of bacteria. For example the bacteria include strains of bacteria that coexist in a commensal or mutualistic relationship with a subject such as, for example, an animal, including human and non-human animals. Exemplary bacteria for use in the methods include mutual, commensal and/or probiotic strains of *Escherichia coli, Bacteroides, Eubacterium, Streptococcus, Actinomyces, Veillonella, Nesseria, Prevotella, Campylobacter, Fusobacterium, Eikenella, Porphyromonas* and *Priopionibacteria*. Exemplary of probiotic bacteria are *Escherichia coli* strain Nissle 1917. Other exemplary probiotic strains include, but are not limited to, *Bacillus cereus, Bacillus licheniformis, Bacillus pumilus, Bacillus clausii, Bacillus coagulans, Bacillus polyfermenticus, Brevibacillus laterosporus, Lactococcus, Lactobacillus reuteri, Lactobacillus amylovorus, Lactobacillus crispatus, Lactobacillus gallinarum, Lactobacillus gasseri, Lactobacillus johnsonii, Lactobacillus bifidum, Lactobacillus helveticus, Bifidobacterium lactis, Bifidobacterium breve, Leuconostoc mesenteroides, Enterococcus faecium, Pediococcus* and *Sporolactobacillus inulinu*. Other exemplary bacteria for use in the methods provided herein include strains that are not probiotic, including but not limited to, *Clostridia, Salmonella, Shigella, Bifidobacteria* and *Staphylococci*.

Therapeutic bacteria are those that tend to accumulate in a certain area or areas of a subject to whom the bacteria are administered. Bacteria used in the methods typically are capable of selectively accumulating in proliferative sites or condition (including, for example, a tumor, tumor tissue, cancer, metastasis, neoplasm, neoplastic disease, site of inflammation, wound, wound tissue and infection) or in immunoprivileged sites relative to other locations in a subject. Because bacteria selectively accumulate at such sites, they can be used to specifically deliver substances and compositions to the sites, including therapeutic substances and compositions for use in treating diseases, disorders and conditions associated with proliferation sites and conditions, including, for example, tumors, cancers, neoplasms, neoplastic diseases, inflammation, wounds and other diseases, conditions and disorders as described herein. Also there are bacteria that provide a therapeutic benefit in the treatment of diseases, disorders and/or conditions without necessarily providing for delivery of a separate therapeutic substance or composition. These include, but are not limited, to probiotic bacteria such as the Nissle strain of *E. coli*.

The probiotic bacteria monitored by the methods herein can be modified from their wild-type form. Modifications can include any of a variety of changes, and typically include changes to the genome or nucleic acid molecules of the bacteria. For example, modifications of bacteria can include one or more modifications of the bacterial genome to add, delete or replace nucleic acid. Such modifications can alter one or more properties of the bacteria including, but not limited to, pathogenicity, toxicity, ability to preferentially accumulate in tumors, ability to lyse cells or cause cell death, replication competence, increased capacity to capture iron or other metals, increased capacity to transport iron, increased capacity to store iron, bind a ligand, or a combination thereof. Exemplary modifications include, but are not limited to deletion of one or more endogenous genes, addition of one or more exogenous genes, mutation of one or more endogenous gene products or alteration of gene expression of one or more endogenous genes.

In some examples, the bacterium can be modified to express one or more exogenous genes in addition to the reporter protein. Exemplary exogenous gene products include proteins and RNA molecules. The modified bacteria can express gene products that are useful for diagnostic or therapeutic uses. Exemplary exogenous gene products that can be expressed by the modified bacteria include, but are not limited to, a detectable gene product (e.g., fluorescent proteins, luminescent proteins), a gene product that induces a detectable signal (e.g. luciferases, ferritin, siderophore), a therapeutic gene product, a protein that serves as a binding site for a ligand (e.g., receptors (e.g., transferrin receptor) or other transmembrane or membrane associated proteins), proteins useful for tumor therapy (e.g., *Pseudomonas* A endotoxin, diphtheria toxin, p53, Arf, Bax, tumor necrosis factor alfa, HSV TK, *E. coli* purine nucleoside phosphorylase and derivatives thereof, cytosine deaminases, uracil, phosphoribosyltransferase and fusions thereof (e.g. FCU1), angiostatin, endostatin, different cytokines) and many other proteins.

In some examples, the bacterium is modified to contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene. In some examples, inducible expression can be under the control of cellular or other factors present in a tumor cell, present in a bacterially-infected tumor cell, or present in/on extracellular bacteria localized in a tumor environment. In other examples, inducible expression can be under the control of an administrable substance, including sugars such as arabinose, xylose, IPTG, RU486 or other known induction compounds. Any of a variety of regulatory sequences are available to one skilled in the art according to known factors and design preferences. In some examples, the regulatory sequence can result in constitutive, high levels of gene expression. In tumor therapy examples, a therapeutic protein can be under the control of an internally inducible promoter or an externally inducible promoter. In some examples, the inducible promoter is a sugar-inducible promoter, such as an arabinose- or xylose-inducible promoter. Recombinant bacteria that contain a sugar-inducible promoter for the expression of exogenous genes can be modified to decrease or abolish the metabolic breakdown of the inducing sugar. For example, bacteria, such as *E. coli*, can be modified such that the breakdown and/or utilization of arabinose in the bacteria is reduced or abolished, which allows for greater accumulation of arabinose in the cells leading to higher gene induction of and longer gene expression from arabinose-inducible promoters in the recombinant bacteria. In one example of the methods provided, inducible promoters can be used to initiate expression of a gene product once the bacteria have accumulated to a particular concentration at the accumulation.

i. *E. coli* Strain Nissle 1917

Exemplary of a bacteria that can be used as a biological therapeutic in the provided methods is *E. coli* strain Nissle 1917, as described in Schultz et al. (2005) *J. Microbiol. Methods* 61(3): 389-398 and U.S. Pat. Nos. 7,763,420 and 7,820,184 and U.S. Patent Publication No. 2009/0180955, all of which are incorporated herein by reference. *E. coli* strain Nissle 1917 lacks defined virulence factors such as alpha-hemolysin and other toxins, mannose-resistant hemagglutinating adhesins, P-fimbrial adhesins, and the semi-rough lipopolysaccharide phenotype (Blum et al. (1996) *Infection*. 23(4):234-236). The unique LPS structure furthermore contributes to its decreased immunotoxicity while maintaining serum sensitivity. Serum sensitivity can contribute to selective colonization of Nissle 1917 in immunoprivileged areas such as tumors, since the bacteria colonize those sites, such as tumors, that are sequestered from the immune system. Nissle 1917 possesses enhanced properties for its use as a therapeutic in part due to the expression of at least six different iron uptake systems, including siderophores such as aerobactin, salmochelin, enterobactin, and yersiniabactin; chu heme transport locus and a ferric dicitrate transport system. The lack of pathogenicity and probiotic properties have lead to its use for the treatment of gut disorders, such as ulcerative colitis, chronic constipation, Crohn's disease, pouchitis, irritable bowel syndrome, and other forms of colitis and gut perturbations. The fact that it accumulates in tumor cells and also can participate in uptake of detectable compounds for imaging and/or therapeutic compounds for treatment has led to its use treating tumors.

*E. coli* strain Nissle 1917 bacteria used in the methods provided herein can be modified. Exemplary nucleic acid molecular modifications include truncations, insertions, deletions and mutations. In an exemplary modification, a microorganism or cell can be modified by truncation, insertion, deletion or mutation of one or more genes. In an exemplary insertion, an exogenous gene can be inserted into the genome of the microorganism or cell or provided on a plasmid. In an exemplary modification, an endogenous gene, an exogenous gene or a combination thereof can be inserted into a plasmid which is inserted into the *E. coli* strain Nissle 1917 bacterium using any of the methods known in the art.

ii. Other Bacteria

Exemplary bacteria that can be used in the methods provided herein include, but are not limited to, strains *Clostridia, Salmonella, Shigella, Bifidobacteria* and *Staphylococci*. In one example, the bacteria for use in the methods provided herein is a *Salmonella typhimurium*, such as *S. typhimurium* strain SL7838, *S. typhimurium* strain VNP20009 and *S. typhimurium* strain TAPET-CD (see, e.g, Barak et al., (2010) *BMC Cancer* 10:146, Friedlos et al., (2008) *Clin Cancer Res* 14:4259-4266, Low et al., (2004) *Methods Mol Med* 90:47-60, Soghomonyan et al., (2005) *Cancer Gene Ther* 12:101-108 and King et al., (2009) *Methods Mol Biol* 542:649-659). *Bifidobactera* for use in the methods provided herein include, but are not limited to, *B. infantis* (Zhu et al., (2011) *Cancer Gene Ther* 18, 884-896) *B. breve* (Cronin et al., (2010) *Mol Ther* 18:1397-1407), *B. adolescentis* (Hu et la., (2009) *Cancer Gene Ther* 16:655-663) and *B. longum* (Taniguchi et al., (2010) *Cancer Sci* 101:1952-1932). *Clostridia* for use in the methods provided herein include, but are not limited to, *C. perfringens* (Li et al., (2009) *Human Gene Ther* 20:75.1-758, Li et al., (2008) *J Natl Cancer Inst* 100:1389-1400) and *C. butyricum* (Mose et al., (1964) *Cancer Res* 24:212-216), *C. acetobutylicum* (Barbe et al., (2005) *FEMS Microbiol Lett* 246:67-73, Theys et al., (2001) *Cancer Detect Prev* 25:548-557) and *C. novyi*-NT (Wei et al., (2008) *Cancer Lett* 259: 16-27).

c. Other Biological Therapies

As noted, the methods herein can be used to monitor therapy with any biological therapeutic in which a gene product is produced. In some examples, the biological therapies include, but are not limited to, gene therapies, immunotherapies, adoptive immunotherapies and other cell therapies.

i. Gene Therapy

In some examples, the method provided herein is used to detect colonization or replication of a gene therapy vector. Gene therapy or genetic therapy involves the transfer of nucleic acid, such as DNA, into certain cells, e.g., target cells, of a mammal, particularly a human, with a disorder or condition for which such therapy is sought. The nucleic acid, such as DNA, is introduced into the selected target cells, such as directly or in a vector or other delivery vehicle, in a manner such that the heterologous nucleic acid, such as DNA, is expressed and a therapeutic product encoded thereby is produced resulting in amelioration or elimination the symptoms, or manifestations of an inherited or acquired disease or curing of the disease. Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy also can be used to deliver nucleic acid encoding a gene product that replaces a defective gene or supplements a gene product produced by the mammal or the cell in which it is introduced. The introduced nucleic acid can encode a therapeutic compound, such as a growth factor or inhibitor thereof, or a tumor necrosis factor or inhibitor thereof, such as a receptor therefore, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy also can involve delivery of an inhibitor or repressor or other modulator of gene expression.

Typically, for detection by the methods provided herein, gene therapy involves administration of a vector encoding the reporter protein to a subject. The vector can any vector, including prokaryotic and mammalian vectors, such as viral vectors, mammalian vectors, bacterial vectors, insect vectors, plant vectors and artificial chromosomes. In some examples, the vector is administered in a virus, such as, but not limited to, a retrovirus, adenovirus, adeno-associated virus and herpes simplex virus. In other examples, the vector is administered in a liposome, PEGylated liposome, nanoparticle, lipid-based nanoparticle or lymphocyte. In yet other example, the vector is delivered administered directly to the subject. In other examples of gene therapy used in the methods provided herein, biologically active nucleic acid molecules, such as RNAi and antisense, are administered to a subject.

ii. Cell Therapy

In some examples, the method provided herein is used to detect colonization or replication of cells introduced for cell therapy. Cell therapy includes cell transplants, including, but not limited to, pancreatic islet, bone marrow, endothelial, epidermal, myoblast, neural and stem cell transplants. Typically, the cell therapy contains a vector encoding a reporter protein. In some examples, the vector contained in the cell therapy encodes an additional heterologous protein, such as a therapeutic protein. A vector for use in a cell therapy provided herein can be a viral vector, mammalian vector, bacterial vector, insect vector, plant vector or artificial chromosome encoding the reporter gene. In some examples, the cell is infected with a virus encoding a reporter protein prior to administration to the subject.

iii. Immunotherapy

In some examples, the methods provided herein are used to detect colonization or replication of colonization/replication of cells used in immunotherapy or adoptive immunotherapy. Immunotherapy is used to stimulate the immune system, for example, to stimulate the immune system to eliminate cancer cells. Active immunotherapy involves injection of cells or proteins, for example, cancer or tumor cells, to generate either new or enhance systemic immune responses to the administered cell or protein. Passive immunotherapy involves the administration of an antibody. Adoptive immunotherapy is a therapeutic approach for treating cancer or infectious diseases in which immune cells are administered to a host with the aim that the cells mediate either directly or indirectly specific immunity to tumor cells and/or antigenic components or regression of the tumor or treatment of infectious diseases, as the case can be. As used in the methods provided herein, immunotherapy or adoptive immunotherapy can include administration of antibodies, proteins or cells for either active or passive immunotherapy. In some examples, the proteins are contained in nanoparticles. In other examples, the immunotherapy involves administration of immune cells or a vaccine. The methods herein, detect, in distinct loci from the targeted tissues or cells, expression of a protein introduced by the therapy or encoded thereby.

2. Reporter Proteins

The biological therapeutics for use in the methods provided herein can encode a reporter protein, which is a detectable protein or a protein that induces a detectable signal. The reporter protein can be endogenous to the therapeutic, such as an endogenous detectable or enzymatic viral product, or can be heterologous. The reporter protein can be a product that normally occurs in the host, in which case increased expression is assessed, or it can be a non-native product, in which any amount of expression is detected, or it can be a product not normally expressed in the sample that is tested.

Upon expression of the reporter gene, the protein or a signal induced by the protein can be detected. Typically, the reporter genes for use in the methods provided herein encode enzymes that catalyze the reaction of a substrate into a detectable product. For example, enzyme reporter genes can catalyze the reaction of a substrate to produce a detectable product or signal, such as a fluorescent, luminescent, chromogenic or spectrophotometric response. Any enzyme is contemplated as long as the protein is capable of being expressed in the biological therapeutic, for example, the oncolytic virus or bacteria. In one example, enzymatic reporter proteins used in the methods herein are human enzymes, including mitochondrial enzymes. In another example, enzymatic reporter proteins used in the methods provided herein are prokaryotic, insect, or plant enzymes. Exemplary reporter enzymes that can be used in the provided method include, but are not limited to, β-glucuronidases, luciferases, beta-galactosidases, chloramphenicol acetyltransferases (CAT) and alkaline phosphatases.

A reporter protein substrate is any substrate upon which interaction with the reporter protein induces a product or signal that can be detected. The signal can be detected directly or indirectly. Typically, the reporter proteins are enzymatic reporter proteins that catalyze production of a product from a substrate. A reporter enzyme substrate is any substrate, for example, any compound, that is a substrate for the reporter enzyme. A reporter enzyme is capable of reacting with the substrate causing a change in the substrate, or a signal, that can be monitored or detected either directly or indirectly. Typically, a reporter enzyme substrate is a compound that is modified upon reaction with the reporter enzyme resulting in a modified compound that can be directly monitored. For example, reporter enzyme substrates typically are colorless or non-fluorescent substrates or compounds that are transformed into colored or fluorescent products upon reaction with the reporter enzyme. For example, in the method provided herein, a reporter enzyme substrate can be a fluorescent, luminescent, chromogenic or spectrophotometric substrate. Reporter enzyme substrates are well known and it is understood that a person of skill in the art can select a suitable substrate for use in the methods provided herein.

a. Reporter Enzymes

Enzymatic reporter genes that can be used in the provided methods include, but are not limited, any protein that exhibits enzymatic activity, e.g., lipases, phospholipases, sulfatases, ureases, peptidases, proteases, esterases, phosphatases, acid phosphatases, glycosidases, glucosidases, glucuronidases, galactosidases, carboxylesterases, luciferases, peroxidases, hydrolases, oxidoreductases, lyases, transferases, isomerases, ligases, synthases, protein kinases, esterases, isomerases, glycosylases, synthetases, dehydrogenases, oxidases, reductases, methylases, oxidases, P450 enzymes, monoamine oxidases (MAOs), flavin monoamine oxidases (FMOs), transferases, glutathione S transferases (GSTs), xanthineguanine phosphoribosyl-transferase, alkaline phosphatases (AP), invertases, luciferases, acetyltransferases, beta-glucuronidases, exo-glucanases, glucoamylases, beta-glucosidases, horseradish peroxidases, alkaline phosphatases, beta-lactamases, alpha-amylases, alpha-glucosidases, catalases, beta-xylosidases, beta-galactosidases, chondroitinsulfatases, gelatinases, collagenases, caseinases, nitroreductases, azoreductases, demethylases, deacetylases, deformylases, phosphatases, kinases, peroxidases, sulfotases, acetylcholinesterases, dehydrogenases, dealkylases and oxygenases. The enzyme reporter genes employed in the methods encode both recombinant and endogenous (native) enzymes. In one embodiment, the enzyme reporter gene encodes an endogenous enzyme. In another embodiment, the enzyme reporter gene encodes a recombinant enzyme. Enzyme reporter genes can easily be determined by one of ordinary skill in the art.

In one embodiment, the enzyme reporter gene encodes a hydrolytic enzyme. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, β-D-mannosidase, β-D-mannosidase, β-D-fructofuranosidase, and β-D-glucosiduronase. Exemplary enzymatic reporter proteins that can be used in the methods provided herein, include, but are not limited to, β-glucuronidases, β-galactosidases, luciferases, chloramphenicol acetyltransferases (CAT) and alkaline phosphatases.

i. β-Glucuronidases

Beta-glucuronidases (β-glucuronidases; Gus; EC 3.2.1.31) are members of the glycosidase family of enzymes that catalyze the breakdown of complex carbohydrates. Beta-glucuronidases are part of the glycosyl hydrolase 2 family of glycosidases. Beta-glucuronidases catalyze the hydrolysis of β-D-glucuronides into the corresponding D-glucuronate and alcohol.

Human β-glucuronidase catalyzes the hydrolysis of β-D-glucuronic acid residues from the non-reducing end of mucopolysaccharides, such as heparin sulfate. Human β-glucuronidase is found in the lysosome where it converts conjugated bilirubin into an unconjugated form for reabsorption. Human β-glucuronidase is also found in breast milk, and contributes to neonatal jaundice. The gene encoding β-glucuronidase is located on chromosome 7. The β-glucuronidase transcript (SEQ ID NO:1) is normally translated to form a 651 amino acid precursor polypeptide (SEQ ID NO:5) containing a 22 amino acid signal sequence at the N-terminus (amino acid residues 1-22). The mature β-glucuronidase therefore, is a 629 amino acid polypeptide set forth in SEQ ID NO:121 (Oshima et al., (1987) *Proc Natl Acad Sci USA* 84:685-689). Beta-glucuronidase is N-linked glycosylated with 3-4 oligosaccharide chains at residues N173, N272, N420 and N631 of SEQ ID NO:5.

Structural analysis reveals human β-glucuronidase is synthesized as an 80 kDa monomer that undergoes proteolysis in the lysosome to remove a signal sequence from the C-terminal end to form a 78 kDa monomer (Islam et al., (1993) 268:22627-22633; Shipley et al., (1993) *J Biol Chem* 268: 12193-12198). Biologically, β-glucuronidase exists as a 332 kDa homotetramer (Kim et al., (2008) *Acta Crystallogr Sect F Struct Biol Cryst Commun* 64(Pt. 12):1169-1171). The tetramer has approximate dihedral symmetry and each promoter includes three structural domains with topologies similar to a jelly roll barrel, an immunoglobulin constant domain and a TIM barrel respectively. The active site of the enzyme is formed from a large cleft at the interface of two monomers. Residues Glu 451 and Glu 540 of SEQ ID NO:5 are proposed to be important for catalysis (Jain et al., (1996) *Nat Struct Biol* 3(4):375-381). β-cholinesterases of this type include, but are not limited to, β-cholinesterases from mouse (SEQ ID NO:115, DNA set forth in SEQ ID NO:2), rat (SEQ ID NO:114, DNA set forth in SEQ ID NO:6), dog (SEQ ID NO:116, DNA set forth in SEQ ID NO:7), cat (SEQ ID NO:117, DNA set forth in SEQ ID NO:8), pig (SEQ ID NO:120, DNA set forth in SEQ ID NO:11), green monkey (SEQ ID NO:118, DNA set forth in SEQ ID NO:9) and Sumatran orangutan (SEQ ID NO:119, DNA set forth in SEQ ID NO:10). Mammalian β-glucuronidases with a pH-optimum under acidic conditions (pH 4 to 5) have strongly reduced capacity at normal (neutral) tissue pH, whereas E. coli β-glucuronidase encoded by gusA works optimal in the range of pH 6.8 to 7.7 (Fang et al., (1995) *Vet Microbiol* 46:361-367).

β-glucuronidases occur in various bacteria, including, but not limited to, *E. coli, Shigella, Salmonella, Lactobacillus, Streptococcus, Clostridium, Roseburia, Anaerococcus, Victivallis, Congregibacter* and *Aspergillus* (Kilian and Bulow (1976) *Acta Pathol Microbiol Scand B.* 84B(5):245-251). β-glucuronidase from *E. coli* strain K12 (gene set forth in SEQ ID NO:3) is normally translated into a 603 amino acid protein set forth in SEQ ID NO:4. Residue E413 of SEQ ID NO:4 is an active site proton donor. Bacterial β-glucuronidases of this type include, but are not limited to, β-glucuronidases from *E. coli* K12 (SEQ ID NO:4, DNA set forth in SEQ ID NO:3), *Shigella flexneri* strain K-18 (SEQ ID NO:128, DNA set forth in SEQ ID NO:127), *Salmonella enterica* (SEQ ID NO:136, DNA set forth in SEQ ID NO:135), *Lactobacillus brevis* strain RO1 (SEQ ID NO:130, DNA set forth in SEQ ID NO:129), *Streptococcus agalactiae* (SEQ ID NO:132, DNA set forth in SEQ ID NO:131), *Clostridium perfringens* (SEQ ID NO:134, DNA set forth in SEQ ID NO:133), *Roseburia intestinalis* (SEQ ID NO:138, DNA set forth in SEQ ID NO:137), *Anaerococcus tetradius* (SEQ ID NO:140, DNA set forth in SEQ ID NO:139), *Victivallis vadensis* (SEQ ID NO:142, DNA set forth in SEQ ID NO:141), *Congregibacter litoralis* (SEQ ID NO:144, DNA set forth in SEQ ID NO:143) and *Aspergillus terreus* (SEQ ID NO:146, DNA set forth in SEQ ID NO:145). Exemplary of a β-glucuronidases used in the provided methods are human and bacterial β-glucuronidases. A β-glucuronidase set forth in any of SEQ ID NOS: 1-11, 114-121 and 127-146, active fragments thereof, or variants thereof can be used in the provided methods.

Also included in the methods provided herein are variants of any of SEQ ID NOS:1-11, 114-121 and 127-146 that have at least or about at least or about or 60%, 70%, 80%, 90%, 91%, 92%, 93%, 94%, 95%, 96%, 97%, 98%, 99% or more sequence identity to any of SEQ ID NOS: 1-11, 114-121 and 127-146. Amino acid variants include variants that contain conservative and non-conservative mutations. It is understood that residues that are important or otherwise required for the activity of a β-glucuronidase, such as any described above or known to skill in the art, are generally invariant and cannot be changed. These include, for example, active site residues. Thus, for example, amino acid residues 451 and 540 (corresponding to residues in the human β-glucuronidase set forth in SEQ ID NO:5) of a human β-glucuronidase are generally invariant and are not altered, or amino acid residue E413 (corresponding to residues in the *E. coli* K12 β-glucuronidase set forth in SEQ ID NO:4) of a bacterial β-glucuronidase are not altered.

For example, there are several alternative splicing forms of human β-glucuronidase, including for example, a short form that does not contain amino acid residues 305-355 of SEQ ID NO:5. β-glucuronidases for use as reporter proteins in the methods provided herein also include variants that have an amino acid modification and that exhibit an altered, such as improved, activity compared to an β-glucuronidase not including the modification. Such variants include those that contain an at least one amino acid modification that enhances the catalytic activity of the β-glucuronidase. Such modified β-glucuronidases include any β-glucuronidase described in the art, including, but not limited to, β-glucuronidases containing at least one mutation corresponding to P30S, C38G, G136R, P148S, E150K, D152G, D152N, L176F, R216W, L243P, Y320C, Y320S, N339S, K350N, H351Y, A354V, D362N, P364L, L376F, R382C, R382H, P408S, P415L, R435P, R477W, Y495C, Y508C, E540K, G572D, K606N, G607A, A619V, Y626H, W627C and L649P in the sequence of amino acids set forth in SEQ ID NO:5.

β-glucuronidases that can be used as a reporter protein in the methods provided herein include modified human beta-glucuronidases with enhanced activity at neutral pH (Chen et al., (2008) *Chem Biol* 15:1277-1286). Also included are β-glucuronidases that have been fused to single chain humanized antibodies for enhanced antibody-directed enzyme prodrug therapy (Chen et al., (2011) *Bioconjug Chem* 22:938-948). β-glucuronidase substrates are set forth in section b below and Table 3.

ii. β-Galactosidases

Beta-galactosidases (β-galactosidases; EC 3.2.1.23) are hydrolase enzymes that catalyze the hydrolysis of β-galactosides into monosaccharides. β-galactosidases belong to the glycosyl hydrolase 35 family. Beta-galactosidases cleave beta-linked terminal galactosyl residues from gangliosides, glycosaminoglycans, lactosylceramides, lactose, and other various glycoproteins. Beta-galactosidases also catalyze hydrolysis of terminal non-reducing beta-D-galactose residues in beta-D-galactosides. The active site of β-galactosidase catalyzes the hydrolysis of its disaccharide substrate via "shallow" and "deep" binding. Monovalent potassium ions ($K^+$) as well as divalent magnesium ions ($Mg^{2+}$) are required for the enzyme's optimal activity. The beta-linkage of the substrate is cleaved by a terminal carboxyl group on the side chain of a glutamic acid.

The human β-galactosidase transcript (SEQ ID NO:12) is normally translated to form a 677 amino acid precursor polypeptide containing a 23 amino acid signal peptide (amino acids 1-23 of SEQ ID NO:13) and a 4 amino acid propeptide (amino acids 24-28 of SEQ ID NO:13). The mature form therefore is a 649 amino acid polypeptide set forth in SEQ ID NO:122 (Oshima et al., (1988) *Biochem Biophys Res Commun* 157:238-244, Yamamoto et al., (1990) *DNA Cell Biol* 9:119-127). Amino acid residue E188 is an active site proton donor and residue E268 is the nucleophile of the hydrolysis reaction (of SEQ ID NO: 13). There are 7 potential N-linked glycosylation sites, including at residues N26, N247, N464, N498, N542, N545 and N555 of SEQ ID NO:13. N-linked glycosylation has been shown at N464 and N555. B-galactosidases of this type include, but are not limited to, mouse (SEQ ID NO:29, DNA set forth in SEQ ID NO:28) and dog (SEQ ID NO:33, DNA set forth in SEQ ID NO:32).

B-galactosidases occur in various bacteria, including, but not limited to, *E. coli, Lactobacillus acidophilus, Sulfolobus solfataricus, Lactococcus lactis, Geobacillus kaustiophilus, Thermus thermophilus, Bacillus subtilis* and *Clostridium perfringens*. Bacterial β-galactosidase from *E. coli* K12 is a 464 kDa homotetramer with 2,2,2-point symmetry that requires magnesium or manganese and sodium cofactors for activity. Each unit of β-galactosidase contains five domains, the third of which is an active site domain (Matthews (2005) *C R Biol*. 328:549-556). The enzyme can be split in two peptides, LacZα and LacZΩ, neither of which is active by itself but both spontaneously reassemble into a functional enzyme. *E. coli* K12 β-galactosidase (SEQ ID NO:15) is normally translated to form a 1024 amino acid polypeptide (SEQ ID NO:14) from which Met1 is removed to form a 1023 amino acid mature protein. Amino acids 538-541 of SEQ ID NO:14 form the substrate binding site, with an active site proton donor at residue 462, a nucleophile at residue 538, sodium binding sites at residues 202, 602 and 605, magnesium 1 binding site at residues 417, 419 and 462 and a magnesium 2 binding site at residue 598. Bacterial β-galactosidases of this type include, but are not limited to, β-galactosidases from *E. coli* K12 (SEQ ID NO:14, DNA set forth in SEQ ID NO:15), *Lactobacillus acidophilus* (SEQ ID NO:16, DNA set forth in SEQ ID NO:17), *Sulfolobus solfataricus* (SEQ ID NO:18, DNA set forth in SEQ ID NO:19), *Lactococcus lactis* (SEQ ID NO:20, DNA set forth in SEQ ID NO:21), *Geobacillus kaustiophilus* (SEQ ID NO:22, DNA set forth in SEQ ID NO:23), *Thermus thermophilus* (SEQ ID NO:24, DNA set forth in SEQ ID NO:25), *Bacillus subtilis*(SEQ ID NO:26, DNA set forth in SEQ ID NO:27) and *Clostridium perfringens* (SEQ ID NO:30, DNA set forth in SEQ ID NO:31). Exemplary of a β-galactosidase is *E. coli* β-galactosidase (set forth in SEQ ID NO:13). A β-galactosidase set forth in any of SEQ ID NOS: 12-33 and 122, active fragments thereof, or variants thereof can be used in the methods provided herein.

Also included in the methods provided herein are variants of any of SEQ ID NOS:12-33 and 122 that have at least or about at least or about or 60%, 70%, 80%, 90%, 91%, 92%, 93%, 94%, 95%, 96%, 97%, 98%, 99% or more sequence identity to any of SEQ ID NOS: 12-33 and 122. Amino acid variants include variants that contain conservative and non-conservative mutations. It is understood that residues that are important or otherwise required for the activity of a β-galactosidase, such as any described above or known to skill in the art, are generally invariant and cannot be changed. These include, for example, active site residues. Thus, for example, amino acid residues 188 and 268 (corresponding to residues in the human β-galactosidase set forth in SEQ ID NO:13) of a human β-galactosidase are generally invariant and are not altered, or amino acid residues 462 and 538 (corresponding to residues in the *E. coli* K12 β-galactosidase set forth in SEQ ID NO:14) of a bacterial β-galactosidase are not altered.

B-galactosidases also can include variants that have an amino acid modification and that exhibits an altered, such as improved, activity compared to a β-galactosidase not including the modification. Such variants include those that contain an at least one amino acid modification that enhances the catalytic activity of the β-galactosidase. Such modified β-galactosidases include any β-galactosidase described in the art, including, but not limited to, β-galactosidases containing at least one mutation corresponding to P10L, R49C, R49H, 151T, R59Q, K73E, T82M, Y83C, Y83H, H89Y, R109W, R121S, G123R, M132T, G134V, P136S, R148c, R148S, S149F, D151V, D151Y, L155R, L162S, L173P, G190D, D198Y, Y199C, R201C, R201H, R201A, D214Y, V216A, V240M, Q255H, P263S, L264S, N266S, Y270D, G272D, W273L, H281Y, Y316C, N318H, T329I, D332E, D332N, Y333H, K346N, Y347C, P297A, Q408P, T420K, T420P, L422R, S434L, L436F, G438E, D441N, R4421, Y444C, R457Q, R482C, R482H, N484K, D491N, D491Y, G494C, G494S, T5001, R521C, S532G, P549L, G554E, K578R, G579D, R590C, R590H, R595W, P597S and E632G in a human beta-galactosidase set forth in SEQ ID NO:13; and D202E, D202N, H358D, H358F, H358L, H358N, E462H, E538Q, H541E, H541F, H541N, F602A, G795A, E798A, E798L, E798D, E798Q, W1000F, W1000G, W1000L and W1000T in a bacterial beta-galactosidase set forth in SEQ ID NO:14. B-galactosidase substrates are set forth in section b below and Table 3.

iii. Luciferases

Luciferases are a class of oxidative enzymes (EC 1.13.12.7) used in bioluminescence. Luciferases produce light by catalyzing the reaction of luciferin and oxygen resulting in the production of oxyluciferin, light and carbon dioxide. In some instances, a cofactor such as calcium ions or ATP is necessary for the luciferase reaction. A variety of organisms have been identified that regulate light production using luciferases. For example, bacterial luciferase lux genes have been identified in *Photorhabdus luminescens* and *Vibrio harveyi*, and eukaryotic luciferase luc and ruc genes have been identified in firefly species (*Photinus* sp.), green click beetle (*Pyrophorus plagiophthalamus*), *Gaussia*, railroad worm (*Phrixothrix hirtus*) and sea pansy (*Renilla reniformis*).

Luciferases that can be used in the method provided herein include, but are not limited to, luciferases from North American firefly (*Photinus pyralis*) (SEQ ID NO:123, DNA set forth in SEQ ID NO:124), North American firefly variant I423L (*Photinus pyralis*) (SEQ ID NO:34, DNA set forth in SEQ ID NO:35), Southern Russian firefly (*Luciola mingrelica*) (SEQ ID NO:37, DNA set forth in SEQ ID NO:36), Japanese firefly (*Luciola cruciata*) (SEQ ID NO:39, DNA set forth in SEQ ID NO:38), Pennsylvania firefly (*Photuris pennsylvanica*) (SEQ ID NO:41, DNA set forth in SEQ ID NO:40), Sea firefly (*Vargula hilgendorfii*) (SEQ ID NO:43, DNA set forth in SEQ ID NO:42), Sea Pansy (*Renilla reniformis*) (SEQ ID NO:45, DNA set forth in SEQ ID NO:44), Green Click Beetle (*Pyrophorus plagiophthalamus*) (SEQ ID NO:47, DNA set forth in SEQ ID NO:46), marine copepod (*Gaussia princeps*) (SEQ ID NO:49, DNA set forth in SEQ ID NO:48) and Railroad worm (*Phrixothrix hirtus*) (SEQ ID NO:51, DNA set forth in SEQ ID NO:50). Bacterial Lux genes that can be included in the methods provided herein include *Vibrio fischeri* ES114 Lux R (SEQ ID NO:93), LuxA (SEQ ID NO:94), LuxB (SEQ ID NO:95), LuxC (SEQ ID NO:96), LuxD (SEQ ID NO:97), LuxE (SEQ ID NO:98, DNA set forth in SEQ ID NO:102), LuxAB (SEQ ID NO:100), LuxCD (SEQ ID NO:101), LuxABCDE (SEQ ID NO:103) Exemplary of luciferases that can be used in the provided methods are firefly, *Renilla*, *Gaussia* and green click beetle luciferases. Any luciferase set forth in any of SEQ ID NOS:34-51, 93-98, 100-103 and 123-124, active fragments thereof, or variants thereof can be used as a reporter gene in the methods provided herein.

Also included in the methods provided herein are variants of any of SEQ ID NOS: 34-51, 93-98, 100-103 and 123-124 that have at least or about at least or about or 60%, 70%, 80%, 90%, 91%, 92%, 93%, 94%, 95%, 96%, 97%, 98%, 99% or more sequence identity to any of SEQ ID NOS: 34-51, 93-98, 100-103 and 123-124. Variants include variants that contain conservative and non-conservative mutations. It is understood that residues that are important or otherwise required for the activity of a luciferase, such as any described above or known to skill in the art, are generally invariant and cannot be changed. Luciferases for use in the methods provided herein also can include variants that have an amino acid modification and that exhibits an altered, such as improved, activity compared to a luciferase not including the modification. Such variants include those that contain an amino acid modification that enhances the catalytic activity of the luciferase. For example, the amino acid modification can be an amino acid replacement (substitution), deletion or insertion.

In the luciferase reaction, light is emitted when luciferase acts on the appropriate luciferin substrate. Photon emission can be detected by light sensitive apparatus such as a luminometer or modified optical microscopes. Luciferase substrates, e.g., luciferins, are set forth in section b below and Table 3.

iv. Chloramphenicol Acetyltransferases

Chloramphenicol acetyltransferase (CAT) are bacterial enzymes (EC 2.3.1.28) that detoxify the antibiotic chloramphenicol and are responsible for chloramphenicol resistance in bacteria. These enzymes covalently attach an acetyl group from acetyl-CoA to chloramphenicol, resulting in acetylated chloramphenicol. A histidine residue, located in the C-terminal section of the enzyme, plays a central role in its catalytic mechanism.

The crystal structure of the type III enzyme from *Escherichia coli* with chloramphenicol bound has been determined. CAT is a trimer of identical subunits (monomer Mr 25,000) and the trimeric structure is stabilized by a number of hydrogen bonds, some of which result in the extension of a beta-sheet across the subunit interface. Chloramphenicol binds in a deep pocket located at the boundary between adjacent subunits of the trimer, such that the majority of residues forming the binding pocket belong to one subunit while the catalytically essential histidine belongs to the adjacent subunit. The active site contains a histidine that is appropriately positioned to act as a general base catalyst in the reaction, and the required tautomeric stabilization is provided by an unusual interaction with a main-chain carbonyl oxygen (Leslie AG (1990) *J Mol Biol* 213:167-186).

Chloramphenicol acetyltransferases that can be used in the methods provided herein include, but are not limited to, those from *E. coli* strain DJ33-16 (SEQ ID NO:53, DNA set forth in SEQ ID NO:52), *Pseudomonas aeruginosa* (SEQ ID NO:55, DNA set forth in SEQ ID NO:54), *Staphylococcus aureus* (SEQ ID NO:57, DNA set forth in SEQ ID NO:56), *Agrobacterium tumefaciens* (SEQ ID NO:59, DNA set forth in SEQ ID NO:58), *Clostridium perfingens* (SEQ ID NO:61, DNA set forth in SEQ ID NO:60), *Klebsiella pneumoniae* (SEQ ID NO:63, DNA set forth in SEQ ID NO:62), *Haemophilus influenzae* (SEQ ID NO:65, DNA set forth in SEQ ID NO:64), *Streptococcus agalactiae* (SEQ ID NO:67, DNA set forth in SEQ ID NO:66), *Bacillus pumilus* (SEQ ID NO:69, DNA set forth in SEQ ID NO:68), *Proteus mirabilis* (SEQ ID NO:71, DNA set forth in SEQ ID NO:70), *Salmonella enterica* (SEQ ID NO:73, DNA set forth in SEQ ID NO:72), *Staphylococcus intermedius* (SEQ ID NO:75, DNA set forth in SEQ ID NO:74), *Listonella anguillarum* (SEQ ID NO:77, DNA set forth in SEQ ID NO:76), *Campylobacter coli* (SEQ ID NO:79, DNA set forth in SEQ ID NO:78) and *Acinetobacter baumannii* (SEQ ID NO:81, DNA set forth in SEQ ID NO:80).

Also included in the methods provided herein are variants of any of SEQ ID NOS:52-81 that have at least or about at least or about or 60%, 70%, 80%, 90%, 91%, 92%, 93%, 94%, 95%, 96%, 97%, 98%, 99% or more sequence identity to any of SEQ ID NOS: 52-81. Variants include variants that contain conservative and non-conservative mutations. It is understood that residues that are important or otherwise required for the activity of a chloramphenicol acetyltransferase, such as any described above or known to skill in the art, are generally invariant and cannot be changed. Chloramphenicol acetyltransferases for use in the methods provided herein also can include variants that have an amino acid modification and that exhibits an altered, such as improved, activity compared to a chloramphenicol acetyltransferase not including the modification. Such variants include those that contain an amino acid modification that enhances the catalytic activity of the chloramphenicol acetyltransferase. For example, the amino acid modification can be an amino acid replacement (substitution), deletion or insertion. Chloramphenicol acetyltransferase substrates include both acetyl coenzyme A (acetyl CoA) and chloramphenicol and are set forth in section b below and Table 3.

v. Alkaline Phosphatases

Alkaline phosphatases (ALP, ALKP) (EC 3.1.3.1) are hydrolase enzymes responsible for removing phosphate groups, e.g., dephosphorylating, from many types of molecules, including nucleotides, proteins, and alkaloids. Alkaline phosphatases are most effective in an alkaline environment. Alkaline phosphatase (ALP) catalyzes the hydrolysis of phosphate esters in alkaline buffer and produces an organic radical and inorganic phosphate.

Exemplary alkaline phosphatases include, but are not limited to, shrimp alkaline phosphatase (SAP), from a species of Arctic shrimp (*Pandalus borealis*) (SEQ ID NO:109, DNA set forth in SEQ ID NO:108), Intestinal Alkaline Phosphatase (AIP; SEQ ID NO:111, DNA set forth in SEQ ID NO:110) and Placental alkaline phosphatase (PALP; SEQ ID NOS: 113, DNA set forth in SEQ ID NO:99 and 112) and secreted alkaline phosphatase (SEAP; SEQ ID NO:126), a C terminally truncated version of PALP.

Also included in the methods provided herein are variants of any of SEQ ID NOS:108-113 and 126 that have at least or about at least or about or 60%, 70%, 80%, 90%, 91%, 92%, 93%, 94%, 95%, 96%, 97%, 98%, 99% or more sequence identity to any of SEQ ID NOS: 108-113 and 126. Variants include variants that contain conservative and non-conservative mutations. It is understood that residues that are important or otherwise required for the activity of an alkaline phosphatase, such as any described above or known to skill in the art, are generally invariant and cannot be changed. Alkaline phosphatases for use in the methods provided herein also can include variants that have an amino acid modification and that exhibits an altered, such as improved, activity compared to an alkaline phosphatase not including the modification. Such variants include those that contain an amino acid modification that enhances the catalytic activity of the alkaline phosphatase. For example, the amino acid modification can be an amino acid replacement (substitution), deletion or insertion. Alkaline phosphatase substrates are set forth in section b below and Table 3.

b. Reporter Enzyme Substrates

A reporter enzyme substrate is any substrate, for example, any compound, that is a substrate for the reporter enzyme. A reporter enzyme is capable of reacting with the substrate causing a change in the substrate that can be monitored directly or indirectly. Typically, a reporter enzyme substrate is a compound that is modified upon reaction with the reporter enzyme resulting in a modified compound that can be directly monitored. For example, reporter enzyme substrates typically are colorless or non-fluorescent substrates or compounds that are transformed into colored or fluorescent products upon reaction with the reporter enzyme. For example, in the method provided herein, a reporter enzyme substrate can be a fluorescent, fluorogenic, luminescent, luminogenic, chromogenic or spectrophotometric substrate or contrast agent. Reporter enzyme substrates are well known and it is understood that a person of skill in the art can select a suitable substrate for use in the methods provided herein.

Exemplary reporter enzymes include, but are not limited to, β-glucuronidases, β-galactosidases, luciferase, chloramphenicol acetyltransferase (CAT) and alkaline phosphatase. One of skill in the art recognizes each reporter enzyme reacts with a substrate specific to the reporter enzyme. Exemplary reporter enzymes and their substrates are set forth in Table 3 below. Typically, reporter enzyme substrates used in the methods provided herein are fluorogenic substrates.

TABLE 3

Exemplary Reporter Enzymes and Substrates

| Reporter Enzyme | Substrate (Abs/Em of the products) * | |
| --- | --- | --- |
| β-D-Glucuronide (β-Glucuronidase, GUS; E.C. 3.2.1.31) | Blue-fluorescent product | 4-Methylumbelliferyl-β-D-glucuronide(4-MUG) (360/449) carboxyumbelliferyl β-D-glucuronide (CuGlcU) (386/445) |
| | Green-fluorescent product | Fluorescein di-β-D-glucuronide (FDGlcU) (490/514) 5-(Pentafluorobenzoylamino)fluorescein β-D-glucuronide (PFB-FDGlcU) (490/514) $C_{12}$-Fluorescein β-D-glucuronide (ImaGene Green ™) (490/514) |
| | Chromogenic substrate | 5-Bromo-4-chloro-3-indoyl β-D-glucuronide (X-GlcU or BCIG) (615/NA) p-nitrophenyl-β-D-glucuronide phenyl-β-D-glucuronide Red-β-D-GlcU, CHA (Magenta-b-D-GlcA; 5-bromo-6-chloro-3-indolyl-b-D-glucuronide, cyclohexylammmonium salt) Rose-β-D-GlcU, CHA (Salmon-β-D-GlcUA; 5-bromo-6-chloro-3-indolyl-β-D-glucuronide, cyclohexylammonium salt) |
| β-D-Galactopyranoside (β-Galactosidase, E.C. 3.2.1.23) | Blue-fluorescent product | 4-Methylumbelliferyl β-D-galactopyranoside (360/449) |
| | Green-fluorescent product | Fluorescein β-D-galactopyranoside (FDG) (490/514) 5-(Pentafluorobenzoylamino)-fluorescein β-D-galactopyranoside (490/514) $C_2$-Fluorescein β-D-galactopyranoside (490/514) |

TABLE 3-continued

Exemplary Reporter Enzymes and Substrates

| Reporter Enzyme | | Substrate (Abs/Em of the products) * |
|---|---|---|
| | Red-fluorescent product | $C_{12}$-Fluorescein β-D-galactopyranoside (490/514)<br>5-Chloromethylfluorescein β-D-galactopyranoside (490/514)<br>$C_{12}$-Resorufin (571/585)<br>DDAO (646/659)<br>Resorufin (571/585) |
| | Chromogenic substrate | 5-Bromo-4-chloro-3-indoyl-β-D-galactopyranoside (615/NA) |
| Luciferases (E.C. 1.13.12.7) | Luminescent | coelenterazine h<br>coelenterazine fcp<br>coelenterazine hcp<br>coelenterazine ip<br>coelenterazine f<br>coelenterazine native<br>D-luciferin ((S)-2-(6-Hydroxy-2-benzothiazolyl)-2-thiazoline-4-carboxylic acid)<br>D-luciferin 6'-O-phosphate<br>luciferin 6'-ethyl ether<br>cypridina luciferin (6-(4-Methoxyphenyl)-2-methyl-3,7-dihydroimidazo[1,2-a]pyrazin-3(7H)-one hydrochloride)<br>click beetle luciferin |
| Chloramphenicol acetyltransferases (E.C. 2.3.1.28) | Radioactive | [$^{14}$C]-chloramphenicol<br>[$^{14}$C]-acetyl CoA |
| | Fluorescent | BODIPY ® FL Chloramphenicol<br>BODIPY ® FL 1-deoxychloramphenicol |
| Alkaline phosphatase (ALP, ALKP, E.C. 3.1.3.1) | Chromogenic | p-nitrophenyl phosphate (pNPP) (405/NA)<br>5-bromo-4-chloro-3-indolyl phosphate (BCIP)<br>5-bromo-4-chloro-3-indolyl phosphate/p-iodonitrotetrazolium Violet (BCIP/INT)<br>5-bromo-4-chloro-3-indolyl phosphate/nitroblue tetrazolium (BCIP/NBT)<br>5-bromo-4-chloro-3-indolyl phosphate/tetranitroblue tetrazolium (BCIP/TNBT)<br>4-Chloro-2-methylbenzenediazonium/3-Hydroxy-2-naphthoic acid 2,4-dimethylanilide phosphate (Fast Red)<br>3-Hydroxy-2-naphthoic acid 2,4-dimethylanilide phosphate/New Fuchsin<br>2-hydroxy-3-naphthoic acid anilide phosphate (Naphthol AS phosphate) |
| | Fluorescent | 4-Methylumbelliferyl phosphate disodium salt (MUP) (360 nm/440)<br>fluorescein diphosphate tetraamonium salt (FDP)<br>Ap-New Magenta<br>AP-orange<br>FirePhos |

* Approximate absorption (Abs) and fluorescence emission (Em) maxima of enzymatic hydrolysis product, in nm i. β-Glucuronidase Substrates An exemplary reporter enzyme for use in the methods herein is β-glucuronidase. Beta-glucuronidase substrates, include but are not limited to, fluorescent, spectrophotometric, or chromogenic substrates that contain the sugar D-glucopyranosiduronic acid attached by glycosidic linkage to a hydroxyl group of a chromogenic, fluorogenic, or other detectable molecule. Fluorescent β-glucuronidase substrates that can be used in the methods provided herein include, but are not limited to, fluorescein di-β-D-glucuronide (FDGlcU), 4-methylumbelliferyl-β-D-glucuronide (4-MUG), carboxyumbelliferyl β-D-glucuronide (CUGlcU), 5-(Pentafluorobenzoyl-amino)fluorescein di-β-D-glucuronide (PFB-FDGlcU), and ImaGene Green™ $C_{12}$-Fluorescein β-D-Glucuronidase Substrate (Invitrogen). Spectrophotometric or chromogenic β-glucuronidase substrates that can be used in the methods provided herein, include, but are not limited to, 5-bromo-4-chloro-3-indolyl β-D-glucuronide (X-GlcU or BCIG), p-nitrophenyl-β-D-glucuronide, Red-β-D-GlcU, CHA (Magenta-b-D-GlcA; 5-bromo-6-chloro-3-indolyl-β-D-glucuronide, cyclohexylammonium salt), Rose-β-D-GlcU,CHA (Salmon-β-D-GlcUA; 5-bromo-6-chloro-3-indolyl β-D-glucuronide, cyclohexylammonium salt), phenyl-β-D-glucuronide, and suitable salts thereof. Exemplary β-glucuronidase substrates for use in the methods provided herein include fluorescein di-β-D-glucuronide (FDGlcU) and 4-methylumbelliferyl-β-D-glucuronide (4-MUG or MUGlcU). It is understood that one of skill in the art can select a suitable β-glucuronidase substrate for use in the methods provided herein.

ii. β-Galactosidase Substrates

An exemplary reporter enzyme for use in the methods herein is β-galactosidase. B-Galactosidase substrates, include but are not limited to, fluorescent, spectrophotometric, or chromogenic substrates that contain the sugar D-galactose attached by glycosidic linkage to a hydroxyl group of a chromogenic, fluorogenic, or other detectable molecule. Fluorescent β-galactosidase substrates that can be used in the methods provided herein include, but are not limited to, 4-Methylumbelliferyl β-D-galactopyranoside, Fluorescein β-D-galactopyranoside (FDG), 5-(Pentafluorobenzoylamino)-fluorescein β-D-galactopyranoside, C2-Fluorescein β-D-galactopyranoside, C12-Fluorescein β-D-galactopyranoside, 5-Chloromethylfluorescein β-D-galactopyranoside, C12-Resorufin, DDAO and Resorufin. Spectrophotometric or chromogenic β-galactosidase substrates that can be used in the methods provided herein, include, but are not limited to, 5-bromo-4-chloro-3-indolyl-β-D-galactopyranoside (X-gal, BCIG) and suitable salts thereof. It is understood that one of skill in the art can select a suitable β-galactosidase substrate for use in the methods provided herein.

iii. Luciferases

Luciferins are a class of small-molecule substrates that are oxidized in the presence of the enzyme luciferase to produce oxyluciferin and energy in the form of light. *Renilla* and *Gaussia* luciferases use coelenterazine as a substrate, whereas firefly luciferases used D-luciferin. Luciferins that can be used as enzyme substrates in the methods provided herein include, but are not limited to, firefly luciferin, latia luciferin, bacterial luciferin, including *Renilla* luciferin, coelenterazine luciferin, dinoflagellate luciferin and virgule or cypridina luciferin. For example, luciferins that can be used in the provided methods include coelenterazine luciferins, such as coelenterazine h, coelenterazine fcp, coelenterazine hcp, coelenterazine ip, coelenterazine f and coelenterazine native, luciferins, such as D-luciferin ((S)-2-(6-Hydroxy-2-benzothiazolyl)-2-thiazoline-4-carboxylic acid), D-luciferin 6'-O-phosphate, and luciferin 6'-ethyl ether, including suitable salts, vargulin or cypridina luciferin (6-(4-Methoxyphenyl)-2-methyl-3,7-dihydroimidazo[1,2-a]pyrazin-3(7H)-one hydrochloride), VivoGlo™ (Promega), EnduRen™ (Promega) and click beetle luciferin.

iv. Chloramphenicol Acetyltransferase (CAT)

Chloramphenicol acetyltransferase requires both chloramphenicol and acetyl coenzyme A (Acetyl CoA) for its activity. CAT activity can be measured using either radioactive or fluorescent substrates. Radioactive substrates that can be used in the methods provided herein include, for example, [$^{14}$C]-chloramphenicol and [$^{14}$C]-acetyl CoA. Fluorescent substrates that can be used in the methods provided herein include, but are not limited to, BODIPY® FL (borondipyrromethene difluoride fluorophore) chloramphenicol and BODIPY® FL 1-deoxychloramphenicol. Exemplary substrates for chloramphenicol acetyltransferases as used in the methods provided herein include fluorescent substrates, such as BODIPY® FL chloramphenicol and BODIPY® FL 1-deoxychloramphenicol.

v. Alkaline Phosphatase

Alkaline phosphatase (ALP) catalyzes the hydrolysis of phosphate esters in alkaline buffer and produces an organic radical and inorganic phosphate. Chromogenic alkaline phosphatase substrates that can be used in the methods provided herein include, but are not limited to, p-nitrophenyl phosphate (pNPP), VECTOR® Red (Vector Labs), VECTOR® Blue (Vector Labs), 5-bromo-4-chloro-3-indolyl phosphate (BCIP), 5-bromo-4-chloro-3-indolyl phosphate/p-iodonitrotetrazolium Violet (BCIP/INT), 5-bromo-4-chloro-3-indolyl phosphate/nitroblue tetrazolium (BCIP/NBT), 5-bromo-4-chloro-3-indolyl phosphate/tetranitroblue tetrazolium (BCIP/TNBT), 4-Chloro-2-methylbenzenediazonium/3-Hydroxy-2-naphthoic acid 2,4-dimethylanilide phosphate (Fast Red), 3-Hydroxy-2-naphthoic acid 2,4-dimethylanilide phosphate/New Fuchsin, 2-hydroxy-3-naphthoic acid anilide phosphate (Naphthol AS phosphate) and suitable salts thereof. Exemplary fluorescent alkaline phosphatase substrates include 4-Methylumbelliferyl phosphate disodium salt (MUP), fluorescein diphosphate, tetraammonium salt (FDP), Ap-New Magenta, AP-orange, FirePhos and suitable salts thereof.

3. Sample

In the methods provided herein, a biological therapeutic, e.g., a virus, bacterium, cell therapy, immunotherapy, adoptive immunotherapy or gene therapy, is administered to a target locus in a subject. The subject can be a human subject or a non-human subject, including mammals, such as a gorilla, chimpanzee, bovine, ovine, horse, swine, goat or ferret, or fowl, such as chicken, a domestic animal such as a feline or canine, or a rodent, such as a rat, mouse, guinea pig, or any human or mammal to whom a biological therapeutic is administered.

In the provided methods, a sample is obtained from the subject to whom the biological therapeutic was administered. The sample is obtained from a locus in the subject other than the target of the biological therapy or the sample is not the targeted or administered cell. In other examples, the sample does not contain the biological therapeutic. In some examples, the sample is from tumor tissue or cells that are treated such that the biological therapeutic is not present in the sample or are normalized to eliminate any contribution from the tumor or target cells or tissue or therapeutic. For example, the sample can be a blood sample or bone marrow sample from a patient with leukemia, as long as the sample does not contain the biological therapeutic or is normalized to eliminate any contribution from the biological therapeutic. Samples for use in the methods herein include body fluids, including but not limited to blood, plasma, serum, lymph, ascetic fluid, bone marrow, cystic fluid, urine, nipple exudates, sweat, tears, saliva, mouth gargle, peritoneal fluid, cerebrospinal fluid (csf), synovial fluid, aqueous humour, vitreous humour, amniotic fluid, bile, cerumen (earwax), Cowper's fluid (pre-ejaculatory fluid), Chyle, Chyme, female ejaculate, interstitial fluid, lymph fluid, menses, breast milk, mucus (including snot and phlegm), pleural fluid, pus, sebum, semen, vaginal lubrication, and feces. In exemplary embodiments, the sample is blood or serum or urine. In some examples, the sample is a tissue sample, such as, for example, a tumor biopsy or fine needle aspirate. The sample can be collected in any clinically acceptable manner, but must be collected such that expressed enzyme reporter proteins are preserved. For example, blood collection for routine clinical testing is generally carried out by venepuncture and varying amounts of blood ranging from 5 mL to 20 mL are collected in vaccutainer tubes having color-coded stoppers.

One skilled in the art will recognize that the time period for effective treatment with the biological therapeutic will vary. For example, the time period for infection of a virus will vary depending on the virus, the organ(s) or tissue(s), the immunocompetence of the host and dosage of the virus. Such times can be empirically determined if necessary. Generally, accumulation of expressed reporter protein can be determined at time points from about less than 1 day, about or 1 day to about 2, 3, 4, 5, 6 or 7 days, about or 1 week to about 2, 3 or 4 weeks, about or 1 month to about 2, 3, 4, 5, 6 months or longer after infection with the virus. Thus, samples can be collected between or between about or at 12 hours to 1 month, 12 hours to 2 weeks, 12 hours to 7 days, 1 day to 7 days, 1 day to 5 days, 1 day to 3 days, 1 day to 2 days, 1 week to 4 weeks, 1 week to 3 weeks, 1 week to 2 weeks after treatment with the biological therapy, or can be collected on or on about 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 4 weeks, 5 weeks, 6 weeks, 7 weeks or 8 weeks after treatment with the biological therapy. In some examples, samples are collected hours after treatment, for example, at at least, at about or at 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours after treatment. In other examples, samples are collected days after treatment, for example at at least, at about or at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days after treatment. In some examples, samples are collected at multiple time points, such as at more than one time point, including, for example, at 1, 2, 3, 4, 5, 6, 7, 8, 9, 10, 15, 20 or more time points.

4. Addition of Reporter Protein Substrates

It is understood by one of skill in the art that the amount of reporter protein substrate added to the sample can be varied based on the reporter protein, the amount of sample to be detected, the incubation time and the intensity of the generated signal, and that the amount of reporter protein substrate added can be increased or decreased as necessary. It is well within the level of skill in the art to select a suitable substrate and amounts thereof.

In some examples, the reporter enzyme substrate is added to the sample at an amount between about or at 1 pg to 1 mg, or between, for example, 1 pg to 1 mg, 1 pg to 1 μg, 1 pg to 1 ng, 1 pg to 500 pg, 50 pg to 1 mg, 50 pg to 1 μg, 50 pg to 1 ng, 50 pg to 500 pg, 250 pg to 1 μg, 250 pg to 1 ng, 250 pg to 750 pg, 500 pg to 1 mg, 500 pg to 1 μg, 500 pg to 1 ng, 1 ng to 1 mg, 1 ng to 500 μg, 1 ng to 1 gig, 1 ng to 500 ng, 250 ng to 1 mg, 250 ng to 500 μg, 250 ng to 250 μg, 250 ng to 1 μg, 250 ng to 750 ng, 500 ng to 1 mg, 500 ng to 500 μg, 500 ng to 1 μg, 1 μg to 1 mg, 1 μg to 500 μg, 1 μg to 250 μg, 1 μg to 100 μg, 1 μg to 50 μg, 1 μg to 10 μg, 10 μg to 1 mg, 10 μg to 500 μg, 10 μg to 250 μg, 10 μg to 100 μg, 10 μg to 50 μg, 25 μg to 500 μg, 25 μg to 250 μg, 25 μg to 100 μg, 50 μg to 1 mg, 50 μg to 500 μg, 50 μg to 250 μg, 50 μg to 100 μg, 100 μg to 1 mg, 100 μg to 500 μg, 100 μg to 300 μg, 300 μg to 700 μg, 300 μg to 500 μg, 500 μg to 1 mg, or is about or at least about or is 1 pg, 5 pg, 10 pg, 20 pg, 30 pg, 40 pg, 50 pg, 100 pg, 150 pg, 200 pg, 250 pg, 300 pg, 350 pg, 400 pg, 500 pg, 550 pg, 600 pg, 650 pg, 700 pg, 750 pg, 800 pg, 850 pg, 900 pg, 950 pg, 1 ng, 10 ng, 20 ng, 30 ng, 40 ng, 50 ng, 100 ng, 150 ng, 200 ng, 250 ng, 300 ng, 350 ng, 400 ng, 450 ng, 500 ng, 550 ng, 600 ng, 650 ng, 700 ng, 750 ng, 800 ng, 850 ng, 900 ng, 950 ng, 1 μg, 1.25 μg, 1.5 μg, 1.75 μg, 2 μg, 2.25 μg, 2.5 μg, 2.75 μg, 3 μg, 3.25 μg, 3.5 μg, 3.75 μg, 4 μg, 4.25 μg, 4.5 μg, 4.75 μg, 5 μg, 5.5 μg, 6 μg, 6.5 μg, 7 μg, 7.5 μg, 8 μg, 8.5 μg, 9 μg, 9.5 μg, 10 μg, 11 μg, 12 μg, 13 μg, 14 μg, 15 μg, 16 μg, 17 μg, 18 μg, 19 μg, 20 μg, 25 μg, 30 μg, 35 μg, 40 μg, 45 μg, 50 μg, 60 μg, 70 μg, 80 μg, 90 μg, 100 μg, 150 μg, 200 μg, 250 μg, 500 μg or 1 mg per sample or any such ranges or amounts.

A sample for use in the methods provided herein can be all or part of a sample obtained from a subject. For example, a sample tested in the methods provided herein can be the entire sample taken from the subject, or can be a portion of the sample taken from the subject. Typically, the sample tested in the methods provided herein is a portion of the sample taken from the subject. For example, the sample for use in the methods can be a volume between 1 μL to 5 mL, typically between 1 μL and 1 mL, for example, from 1 μL to 500 μL, 1 μL to 250 μl, 1 μL to 100 μL, 1 μL to 75 μL, 1 μL to 50 μL, 1 μL to 25 μL, 1 μL to 20 μL, 1 μL to 15 μL, 1 μL to 10 μL, 1 μL to 5 μL, 5 μL to 500 μL, 5 μL to 250 μL, 5 μL 50 100 μL, 5 μL to 50 μL, 5 μL to 25 μL, 5 μL to 15 μL, 5 μL to 10 μL, 10 μL to 500 μL, 10 μL to 250 μL, 10 μL to 100 μL, 10 μL to 50 μL, 10 μL to 25 μL, 10 μL to 20 μL, 15 μL to 500 μL, 15 μL to 250 μL, 15 μL to 100 μL, 15 μL to 75 μL, 15 μL to 50 μL, 15 μL to 25 μL, 20 μL to 500 μL, 20 μL to 250 μL, 20 μL to 200 μL, 20 μL to 100 μL, 20 μL to 50 μL, 50 μL to 500 μL, 50 μL to 250 μL, 50 μL to 200 μL, 50 μL to 150 μL, 50 μL to 100 μL, 100 μL to 1000 μL, 100 μL to 250 μL, 100 μL to 200 μL, 100 μL to 150 μL, 250 μL to 750 μL, or 500 μL to 1 mL, or the sample is at least or is about or is 1 μL, 2 μL, 3 μL, 4 μL, 5 μL, 6 μL, 7 μL, 8 μL, 9 μL, 10 μL, 11 μL, 12 μL, 13 μL, 14 μL, 15 μL, 16 μL, 17 μL, 18 μL, 19 μL, 20 μL, 25 μL, 30 μL, 35 μL, 40 μL, 45 μL, 50 μL, 60 μL, 70 μL, 75 μL, 80 μL, 90 μL, 100 μL, 110 μL, 120 μL, 130 μL, 140 μL, 150 μL, 160 μL, 170 μL, 180 μL, 190 μL, 200 μL, 250 μL, 300 μL, 350 μL, 400 μL, 450 μL, 500 μL, 600 μL, 700 μL, 800 μL, 900 μL, or 1 mL or more. In an exemplary example, 20 μL of sample was used in the method provided herein.

In other examples, the amount of substrate added is varied in relation to the amount of sample. For example, the ratio of substrate to sample is from 1:1,000,00 to 1:1, such as, for example, 1:1,000,000 to 1:100,000; 1:1,000,000 to 1:10,000; 1:1,000,000 to 1:1,000; 1:500,000 to 1:100,000; 1:500,000 to 1:50,000; 1:500,000 to 1:10,000; 1:100,000 to 10,000; 1:100,000 to 1:1,000; 1:100,000 to 1:500; 1:50,000 to 1:10,000; 1:50,000 to 1:1,000; 1:50,000 to 1:500; 1:10,000 to 1:1,000; 1:10,000 to 1:500; 1:10,000 to 1:100; 1:10,000 to 1:1; 1:1000 to 1:500; 1:1000 to 1:100; 1:1000 to 1:1; 1:500 to 1:100; 1:500 to 1:1, or the ratio of substrate to sample is at least or at least about or is 1:1,000,000, 1:500,000, 1:250,000, 1:100,000, 1:75,000, 1:50,000, 1:25,000, 1:10,000, 1:5,000, 1:2,500, 1:1,000, 1:900, 1:800, 1:700, 1:600, 1:500, 1:400, 1:300, 1:200, 1:100, 1:50, 1:45, 1:40, 1:35, 1:30, 1:25, 1:20, 1:15, 1:10, 1:5, 1:4, 1:3, 1:2, 1:1 or less, weight to volume (w/v) of the substrate to sample. In an exemplary example, 3.75 μg of reporter substrate was added to 20 μL of sample.

5. Incubation of the Sample and the Reporter Protein Substrate

In the method in which enzymes are detected, after the substrate is added to the sample, the sample and the reporter protein substrate are incubated for a sufficient period of time to allow reaction of the reporter protein and the substrate. For example, the sample and the substrate can be incubated for minutes, hours or days, depending on the reporter protein and the substrate. The time periods and conditions therefore, if necessary, can be empirically determined. In one example, the sample and the substrate are incubated for 10, 20, 30, or 60 minutes prior to detection or other such time period. In another example, the sample and the substrate are incubated for 30 minutes or less prior to detection. In yet another example, the sample and the substrate are incubated for more than one hour prior to detection.

In some examples of the methods provided herein, a sufficient period of time is from or from about 1 minute to 2 hours, 1 minute to 1 hour, 1 minute to 30 minutes, 1 minute to 15 minutes, 15 minutes to 2 hours, 15 minutes to 1 hour, 15 minutes to 45 minutes, 15 minutes to 30 minutes, 30 minutes to 6 hours, 30 minutes to 4 hours, 30 minutes to 2 hours, 30 minutes to 1 hour, 1 hour to 24 hours, 1 hour to 18 hours, 1 hour to 12 hours, 1 hour to 6 hours, 1 hour to 3 hours, 1 hour to 2 hours, 6 hours to 24 hours, 6 hours to 18 hours, 6 hours to 12 hours, 12 hours to 24 hours, 12 hours to 18 hours, or is at least or is about or is 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 12 hours, 18 hours or 24 hours or more. It is understood that reaction times can vary based on reporter protein and substrate, and that one of skill in the art can select a suitable reaction time.

6. Detection of Activated Substrate or Signal

In the method provided herein, after the sample is incubated with the substrate, the activated substrate or signal can be detected using any method known to one of skill in the art, including, but not limited, to chromogenic, spectrophotometric, fluorimetric, radioactive and luminescent methods of detection. In one example, a chromogenic or spectrophotometric substrate or signal is detected with a spectrophotometer. In another example, a fluorescent product derived from a fluorogenic substrate or signal is detected with a fluorometer or by fluorescence imaging. In another example, a radioactive substrate or signal is detected by scintillation counter, scintigraphy, gamma camera, a β+ detector, a γ detector, or a combination thereof. In yet another example, photon emission, such as that emitted by a luciferase, can be detected by light sensitive apparatus such as a luminometer or modified optical microscopes. In another example, signal can be detected with a Raman spectrometer. In yet other examples, substrate is detected when changes in fluorescent or optical properties, such as wavelength changes, intensity changes or changes in absorption, occur upon activation or cleavage by the reporter protein. In some examples, detection is effected by capturing with an antibody presented on a nanoparticle (see, e.g., Wang et al., (2011) *Analyst.* 136:4295-4300).

It is understood that the above discussion and following discussion are exemplary only, and, that any biological therapeutic and any protein or product encoded thereby, particularly enzyme products, is contemplated herein, as long as the sample is different from the administered therapeutic or does not contain the administered therapeutic or, if it does, enhanced amounts of production of the product, are assessed. The methods herein assess and detect replication of and/or expression of products encoded by a biological therapeutic at a locus or in a tissue or sample that is not the target for the therapy. In particular, the body fluids, such as any known to those of skill in the art or noted herein, is/are sampled, and a product encoded by the biological therapeutic is detected or signal induced thereby is detected.

D. Methods of Preparing Biological Therapeutics Encoding A Reporter Protein

Biological therapeutics can be prepared by any method known to those of skill in the art or obtained from commercial sources or by methods to be developed. In some embodiments, in which a heterologous encoded product is detected, the biological therapeutic can be modified or selected to encode such product by any of the well known methods. For example, if the detected product is a reporter gene product, such as an enzyme, the reporter gene product can be encoded by the biological therapeutic, such as a therapeutic vector or microorganism. Typically, genes encoding the reporter proteins are contained within vectors, such as prokaryotic and eukaryotic vectors, including viral vectors, mammalian vectors, bacterial vectors, plant vectors and insect vectors. Alternatively, the gene can be contained in artificial chromosomes. Methods for generating vectors, including cloning, isolating or modifying nucleic acid molecules are well known to one of skill in the art.

Any method known to those of skill in the art for identification, selection or production of nucleic acids that encode desired genes, such as reporter proteins, can be used. Any method available in the art can be used to obtain a full length (i.e., encompassing the entire coding region) cDNA or genomic DNA clone encoding a reporter protein, such as from a cell or tissue source. Methods for amplification of nucleic acids can be used to isolate nucleic acid molecules encoding a desired polypeptide, including for example, polymerase chain reaction (PCR) methods. A nucleic acid containing material can be used as a starting material from which a desired polypeptide-encoding nucleic acid molecule can be isolated. For example, DNA and mRNA preparations, cell extracts, tissue extracts, fluid samples (e.g. blood, serum, saliva), samples from healthy and/or diseased subjects can be used in amplification methods. Nucleic acid libraries also can be used as a source of starting material. Primers can be designed to amplify a gene encoding a desired polypeptide. For example, primers can be designed based on expressed sequences from which a desired polypeptide is generated. Primers can be designed based on back-translation of a polypeptide amino acid sequence. Nucleic acid molecules generated by amplification can be sequenced and confirmed to encode a desired polypeptide.

Additional nucleotide sequences can be joined to a polypeptide-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a polypeptide-encoding nucleic acid molecule. Examples of such sequences include, but are not limited to, promoter sequences designed to facilitate intracellular protein expression, and secretion sequences, for example heterologous signal sequences, designed to facilitate protein secretion. Such sequences are known to those of skill in the art.

The identified and isolated nucleic acids then can be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pCMV4, pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. Insertion can be effected using TOPO cloning vectors (Invitrogen, Carlsbad, Calif.). If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized oligonucleotides encoding restriction endonuclease recognition sequences. In an alternative method, the cleaved vector and protein gene can be modified by homopolymeric tailing. Recombinant molecules can be introduced into host cells via, for example, transformation, transfection, infection, electroporation and sonoporation, so that many copies of the gene sequence are generated.

1. Vectors

For generation of a vector containing a gene encoding a reporter protein for use in a biological therapeutic to be detected by the methods provided herein, the nucleic acid containing all or a portion of the nucleotide sequence encoding the reporter protein can be inserted into an appropriate expression vector, i.e., a vector that contains the necessary elements for the transcription and translation of the inserted protein coding sequence. The necessary transcriptional and translational signals also can be supplied by the native promoter for enzyme genes, and/or their flanking regions. Provided are vectors that contain a sequence of nucleotides that encodes a reporter protein, such as a β-glucuronidase, coupled to the native or heterologous signal sequence, as well as multiple copies thereof. The vectors can be selected for expression of the protein in the cell or such that the protein is expressed as a secreted protein.

A variety of host-vector systems can be used to express the protein coding sequence. These include but are not limited to mammalian cell systems infected with virus (e.g. vaccinia virus, adenovirus and other viruses); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding protein, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a desired protein. Promoters which can be used include but are not limited to the SV40 early promoter (Bernoist and Chambon, *Nature* 290:304-310 (1981)), the promoter contained in the 3' long terminal repeat of Rous sarcoma virus (Yamamoto et al. *Cell* 22:787-797 (1980)), the herpes thymidine kinase promoter (Wagner et al., *Proc. Natl. Acad. Sci.* USA 78:1441-1445 (1981)), the regulatory sequences of the metallothionein gene (Brinster et al., *Nature* 296:39-42 (1982)); prokaryotic expression vectors such as the β-lactamase promoter (Jay et al., (1981) *Proc. Natl. Acad. Sci. USA* 78:5543) or the tac promoter (DeBoer et al., *Proc. Natl. Acad. Sci. USA* 80:21-25(1983)); see also "Useful Proteins from Recombinant Bacteria": in Scientific American 242:79-94 (1980)); plant expression vectors containing the nopaline synthetase promoter Herrera-Estrella et al., *Nature* 303:209-213 (1984)) or the cauliflower mosaic virus 35S RNA promoter (Gardner et al., *Nucleic Acids Res.* 9:2871 (1981)), and the promoter of the photosynthetic enzyme ribulose bisphosphate carboxylase (Herrera-Estrella et al., *Nature* 310:115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639-646(1984); Ornitz et al., *Cold Spring Harbor Symp. Quant. Biol.* 50:399-409 (1986); MacDonald, *Hepatology* 7:42S-51S (1987)); insulin gene control region which is active in pancreatic beta cells (Hanahan et al., *Nature* 315:115-122 (1985)), immunoglobulin gene control region which is active in lymphoid cells (Grosschedl et al., *Cell* 38:647-658(1984); Adams et al., *Nature* 318:533-538 (1985); Alexander et al., *Mol. Cell Biol.* 7:1436-1444(1987)), mouse mammary tumor virus control region which is active in testicular, breast, lymphoid and mast cells (Leder et al., *Cell* 45:485-495 (1986)), albumin gene control region which is active in liver (Pinkert et al., *Genes and Devel* 1:268-276 (1987)), alpha-fetoprotein gene control region which is active in liver (Krumlauf et al., *Mol. Cell. Biol.* 5:1639-1648 (1985); Hammer et al., *Science* 235:53-58 1987)), alpha-1 antitrypsin gene control region which is active in liver (Kelsey et al., *Genes and Devel.* 1:161-171 (1987)), beta globin gene control region which is active in myeloid cells (Magram et al., *Nature* 315:338-340 (1985); Kollias et al., *Cell* 46:89-94 (1986)), myelin basic protein gene control region which is active in oligodendrocyte cells of the brain (Readhead et al., *Cell* 48:703-712(1987)), myosin light chain-2 gene control region which is active in skeletal muscle (Shani, *Nature* 314: 283-286 (1985)), and gonadotrophic releasing hormone gene control region which is active in gonadotrophs of the hypothalamus (Mason et al., *Science* 234:1372-1378(1986)).

For example, a vector is used that contains a promoter operably linked to nucleic acids encoding a reporter protein, one or more origins of replication, and optionally, one or more selectable markers (e.g., an antibiotic resistance gene). Exemplary plasmid vectors for transformation of *E. coli* cells, include, for example, the pQE expression vectors (available from Qiagen, Valencia, Calif.; see also literature published by Qiagen describing the system). pQE vectors have a phage T5 promoter (recognized by *E. coli* RNA polymerase) and a double lac operator repression module to provide tightly regulated, high-level expression of recombinant proteins in *E. coli*, a synthetic ribosomal binding site (RBS II) for efficient translation, a 6×His tag coding sequence, $t_0$ and T1 transcriptional terminators, ColE1 origin of replication, and a beta-lactamase gene for conferring ampicillin resistance. The pQE vectors enable placement of a 6×His tag at either the N- or C-terminus of the recombinant protein. Such plasmids include pQE 32, pQE 30, and pQE 31 which provide multiple cloning sites for all three reading frames and provide for the expression of N-terminally 6×His-tagged proteins. Other exemplary plasmid vectors for transformation of *E. coli* cells, include, for example, the pET expression vectors (see, U.S. Pat. No. 4,952,496; available from Novagen, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator.

In other embodiments, organ or tissue-specific expression of a reporter protein within a biological therapeutic can be controlled by regulatory sequences. In order to achieve expression only in the target organ, for example, a tumor to be treated, the foreign nucleotide sequence can be linked to a tissue specific promoter and used for gene therapy. Such promoters are well known to those skilled in the art (see e.g., Zimmermann et al., (1994) *Neuron* 12, 11-24; Vidal et al.; (1990) *EMBO J.* 9, 833-840; Mayford et al., (1995), *Cell* 81, 891-904; Pinkert et al., (1987) *Genes & Dev.* 1, 268-76).

2. Viruses

The viruses for use in the methods provided herein can be formed by standard methodologies well known in the art for producing and/or modifying viruses. Briefly, the methods can include introducing into viruses one or more genetic modifications, followed by screening the viruses for properties reflective of the modification or for other desired properties.

a. Genetic Modifications

Standard techniques in molecular biology can be used to generate the modified viruses for use in the methods provided herein. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis. Alternatively, homologous recombination can be used to introduce a mutation or exogenous sequence into a target sequence of interest. In an alternative mutagenesis protocol, point mutations in a particular gene also can be selected for using a positive selection pressure. See, e.g., Current Techniques in Molecular Biology, (Ed. Ausubel, et al.). Nucleic acid amplification protocols include but are not limited to the polymerase chain reaction (PCR). Use of nucleic acid tools such as plasmids, vectors, promoters and other regulating sequences, are well known in the art for a large variety of viruses and cellular organisms. Nucleic acid transfer protocols include calcium chloride transformation/transfection, electroporation, liposome mediated nucleic acid transfer, N-[1-(2,3-Dioloyloxy) propyl]-N,N,N-trimethylammonium methylsulfate meditated transformation, and others. Further a large variety of nucleic acid tools are available from many different sources including ATCC, and various commercial sources. One skilled in the art will be readily able to select the appropriate tools and methods for genetic modifications of any particular virus according to the knowledge in the art and design choice.

Any of a variety of modifications can be readily accomplished using standard molecular biological methods known in the art. The modifications will typically be one or more truncations, deletions, mutations or insertions of the viral genome. In one embodiment, the modification can be specifically directed to a particular sequence. The modifications can be directed to any of a variety of regions of the viral genome, including, but not limited to, a regulatory sequence, to a gene-encoding sequence, or to a sequence without a known role. Any of a variety of regions of viral genomes that are available for modification are readily known in the art for many viruses, including the viruses specifically listed herein. As a non-limiting example, the loci of a variety of vaccinia genes provided herein and elsewhere exemplify the number of different regions that can be targeted for modification in the viruses provided herein. In another embodiment, the modification can be fully or partially random, whereupon selection of any particular modified virus can be determined according to the desired properties of the modified the virus. These methods include, for example, in vitro recombination techniques, synthetic methods and in vivo recombination methods as described, for example, in Sambrook et al., Molecular Cloning: A Laboratory Manual, 2nd edition, Cold Spring Harbor Laboratory Press, cold Spring Harbor N.Y. (1989), and in the Examples disclosed herein.

The viruses for use as therapeutics detected by the methods provided herein encode a reporter protein, for example, an enzyme, including for example, β-glucuronidase, β-galactosidase, luciferases, chloramphenicol acetyltransferases or alkaline phosphatase. In some embodiments, the virus can be modified to express an additional exogenous gene. Exemplary exogenous gene products include proteins and RNA molecules. The modified viruses can express a detectable gene product, a therapeutic gene product, a gene product for manufacturing or harvesting, or an antigenic gene product for antibody harvesting. The characteristics of such gene products are described herein and elsewhere. In some embodiments of modifying an organism to express an exogenous gene, the modification can also contain one or more regulatory sequences to regulate expression of the exogenous gene. As is known in the art, regulatory sequences can permit constitutive expression of the exogenous gene or can permit inducible expression of the exogenous gene. Further, the regulatory sequence can permit control of the level of expression of the exogenous gene. In some examples, inducible expression can be under the control of cellular or other factors present in a tumor cell or present in a virus-infected tumor cell. In other examples, inducible expression can be under the control of an administrable substance, including IPTG, RU486 or other known induction compounds. Any of a variety of regulatory sequences are available to one skilled in the art and can be selected according to known factors and design preferences. In some embodiments, such as gene product manufacture and harvesting, the regulatory sequence can result in constitutive, high levels of gene expression. In some embodiments, such as anti-(gene product) antibody harvesting, the regulatory sequence can result in constitutive, lower levels of gene expression. In tumor therapy embodiments, a therapeutic protein can be under the control of an internally inducible promoter or an externally inducible promoter.

In other embodiments, organ or tissue-specific expression can be controlled by regulatory sequences. In order to achieve expression only in the target organ, for example, a tumor to be treated, the foreign nucleotide sequence can be linked to a tissue specific promoter and used for gene therapy. Such promoters are well known to those skilled in the art (see e.g., Zimmermann et al., *Neuron* 12: 11-24 (1994); Vidal et al., *EMBO J.* 9: 833-840 (1990); Mayford et al., *Cell* 81: 891-904 (1995); and Pinkert et al., *Genes & Dev.* 1: 268-76 (1987)).

In some embodiments, the viruses can be modified to express two or more proteins, where any combination of the two or more proteins can be one or more detectable gene products, therapeutic gene products, gene products for manufacturing or harvesting or antigenic gene products for antibody harvesting. In one embodiment, a virus can be modified to express a detectable protein and a therapeutic protein. In another embodiment, a virus can be modified to express two or more gene products for detection or two or more therapeutic gene products. For example, one or more proteins involved in biosynthesis of a luciferase substrate can be expressed along with luciferase. When two or more exogenous genes are introduced, the genes can be regulated under the same or different regulatory sequences, and the genes can be inserted in the same or different regions of the viral genome, in a single or a plurality of genetic manipulation steps. In some embodiments, one gene, such as a gene encoding a detectable gene product, can be under the control of a constitutive promoter, while a second gene, such as a gene encoding a therapeutic gene product, can be under the control of an inducible promoter. Methods for inserting two or more genes in to a virus are known in the art and can be readily performed for a wide variety of viruses using a wide variety of exogenous genes, regulatory sequences, and/or other nucleic acid sequences.

Methods of producing recombinant viruses are known in the art. Provided herein for exemplary purposes are methods of producing a recombinant vaccinia virus. A recombinant vaccinia virus with an insertion in the F14.5L gene (NotI site of LIVP) can be prepared by the following steps: (a) generating (i) a vaccinia shuttle plasmid containing the modified F14.5L gene inserted at restriction site X and (ii) a dephosphorylated wt VV (VGL) DNA digested at restriction site X; (b) transfecting host cells infected with PUV-inactivated helper VV (VGL) with a mixture of the constructs of (i) and (ii) of step a; and (c) isolating the recombinant vaccinia viruses from the transfectants. One skilled in the art knows how to perform such methods, for example by following the instructions given in U.S. Publication Nos. 2005-0031643 and 2006-051370 and U.S. Pat. Nos. 7,588,767 and 7,588, 771; see also Timiryasova et al. (*Biotechniques* 31: 534-540 (2001)). In one embodiment, restriction site X is a unique restriction site. A variety of suitable host cells also are known to the person skilled in the art and include many mammalian, avian and insect cells and tissues which are susceptible for vaccinia virus infection, including chicken embryo, rabbit, hamster and monkey kidney cells, for example, HeLa cells, $RK_{13}$, CV-1, Vero, BSC40 and BSC-1 monkey kidney cells.

b. Control of Heterologous Gene Expression

In some embodiments, expression the therapeutic product can be controlled by a regulatory sequence. Suitable regulatory sequences which, for example, are functional in a mammalian host cell are well known in the art. In one example, the regulatory sequence contains a poxvirus promoter. In another embodiment, the regulatory sequence can contain a natural or synthetic vaccinia virus promoter. Strong late promoters can be used to achieve high levels of expression of the foreign genes. Early and intermediate-stage promoters also can be used. In one embodiment, the promoters contain early and late promoter elements, for example, the vaccinia virus early/late promoter P7.5k, vaccinia late promoter P11k, a synthetic early/late vaccinia PSEL promoter (Patel et al., (1988) *Proc. Natl. Acad. Sci. USA* 85: 9431-9435; Davison and Moss, (1989) *J Mol Biol* 210: 749-769; Davison et al. (1990) *Nucleic Acids Res.* 18: 4285-4286; Chakrabarti et al. (1997), *BioTechniques* 23: 1094-1097). As described elsewhere herein, the viruses provided can exhibit differences in characteristics, such as attenuation, as a result of using a stronger promoter versus a weaker promoter. For example, in vaccinia, synthetic early/late and late promoters are relatively strong promoters, whereas vaccinia synthetic early, P7.5k early/late, P7.5k early, and P28 late promoters are relatively weaker promoters (see e.g., Chakrabarti et al. (1997) *BioTechniques* 23(6) 1094-1097). Combinations of different promoters can be used to express different gene products in the same virus or two different viruses. In one embodiment, different therapeutic or detectable gene products are expressed from different promoters, such as two different vaccinia synthetic promoters.

3. Bacteria

The bacteria used in the methods provided herein can be formed by standard methodologies well known in the art for producing or modifying bacteria. Briefly, the methods include introducing into the bacteria one or more genetic modification(s), followed by screening the bacteria for properties reflective of the modification(s) or for other desired properties. Exemplary nucleic acid molecular modifications include truncations, insertions, deletions and mutations. In an exemplary modification, bacteria can be modified by truncation, insertion, deletion or mutation of one or more genes. In some examples, nucleic acid carrying multiple genes can be inserted into the genome of the bacterium or provided on a plasmid. The bacteria for use in the methods provided herein are modified to encode a reporter gene, including for example, β-glucuronidase, β-galactosidase, luciferases, chloramphenicol acetyltransferases or alkaline phosphatase. In one example, a bacterium can be modified to carry the lux operon for the production of bacterial luciferase and proteins for the generation of the bacterial luciferase substrate. In an exemplary modification, an endogenous gene, an exogenous gene or a combination thereof can be inserted into a plasmid which is inserted into the bacteria using any of the methods known in the art. Methods for optimizing expression genes are known in the art and include, for example, modification of copy number, promoter strength, deletion of genes that encode inhibitory proteins, or movement of essential genes to a plasmid in order to maintain the plasmid in the transformed bacteria. The modifications can be directed to any of a variety of regions of the bacterial genome or endogenous plasmids, including, but not limited to, a regulatory sequence, to a gene-encoding sequence, or to a sequence without a known role. Any of a variety of regions of bacterial genomes that are available for modification are readily known in the art for many bacteria, including the bacteria specifically listed herein.

Standard techniques in molecular biology can be used to generate the modified bacteria for use in the methods provided. Such techniques include various nucleic acid manipulation techniques, nucleic acid transfer protocols, nucleic acid amplification protocols, and other molecular biology techniques known in the art. For example, point mutations can be introduced into a gene of interest through the use of oligonucleotide mediated site-directed mutagenesis. Alternatively, homologous recombination techniques can be used to introduce a mutation or exogenous sequence into a target sequence of interest; or can be used to inactivate a target sequence of interest. Nucleic acid transfer protocols include calcium chloride transformation/transfection, transduction, electroporation, liposome mediated nucleic acid transfer and others. In an alternative mutagenesis protocol, point mutations in a particular gene also can be selected for using a positive selection pressure. See, e.g., *Current Protocols in Molecular Biology*, (ed. Ausubel, et al.). Nucleic acid amplification protocols include but are not limited to the polymerase chain reaction (PCR). Use of nucleic acid tools such as plasmids, vectors, promoters and other regulating sequences, are well known in the art for a large variety of organisms for use in bacterial expression systems. Plasmids can be created to carry genes using methods known to one skilled in the art. High copy plasmids can be used to cause over-expression of endogenous or heterologous proteins in a bacterium. Further, a large variety of nucleic acid tools are available from many different sources including the American Type Culture Collection (ATCC), and various commercial sources. One skilled in the art will be readily able to select the appropriate tools and methods for genetic modifications of any particular bacterium according to the knowledge in the art and design choice.

Expression of exogenous genes can be controlled by a constitutive promoter, or by an inducible promoter. Expression also can be influenced by one or more proteins or RNA molecules expressed by the bacteria. Genes can be encoded in a bacterial chromosome or on a plasmid. Over-expression of a gene or gene product can be achieved by insertion of a gene into the bacterial chromosome under the control of a strong promoter. Plasmids can be created to carry genes using methods known to one skilled in the art. High copy plasmids can be used to cause over-expression of exogenous proteins in bacteria. Plasmids for expression of proteins include, but are not limited to ColE1, pBR322, p15A, pEMBLex2, pMAL-p2, pUC18A2 (a pUC18-derived plasmid containing the ftn gene), pUC118, pGS281, pMK4, pUNK1, pAMβ1 and pTA1060. Choice of a plasmid for expression at desired levels is well-known in the art as well as techniques to introduce genes into the plasmids (Sambrook et al. *Molecular Cloning: A Laboratory Manual.* $2^{nd}$ ed. Cold Spring Harbor Laboratory Press, New York, N.Y. 1989; *Current Protocols in Molecular Biology.* Ed. Ausubel et al. John Wiley & Sons, Inc. Cambridge, Mass., 1995).

E. Methods for Detecting and Monitoring Therapy

Methods for detecting, assessing and/or monitory therapy by a biological therapeutic are provided. The methods can detect and/or monitor the effectiveness of therapy. For example, the methods for detecting colonization or replication of or by a biological therapeutic can be used, for example, for detecting and/or diagnosing diseases and disorders, evaluating the efficacy or progress of a treatment or therapy for a disease or disorder, evaluating or determining an optimal time of induction of therapeutic gene expression for a bacterial- or viral-mediated treatment or therapy for a disease or disorder, developing non-human animal models for diseases and disorders, assaying or screening compositions for potential use as therapeutic agents for the treatment of diseases and disorders and for tracking or monitoring delivery of compositions to cells and tissues, including, sites of cellular proliferation, tumors, tumor tissues, tumor cells, including circulating tumor cells, metastases, areas of inflammation, wounds and infections.

The methods for detecting colonization or replication of a biological therapeutic provided herein, such as an oncolytic virus or adoptive immunotherapy, can used to monitor treatment of cancers and tumors, such as, but not limited to, bladder tumors, breast tumors, prostate tumors, glioma tumors, adenocarcinomas; ovarian carcinomas, and pancreatic carcinomas, liver tumors and skin tumors, pancreatic cancer, non-small cell lung cancer, multiple myeloma, or leukemia; cancer-forming solid tumors, such as lung and bronchus, breast, colon and rectum, kidney, stomach, esophagus, liver and intrahepatic bile duct, urinary bladder, brain and other nervous system, head and neck, oral cavity and pharynx, cervix, uterine corpus, thyroid, ovary, testes, prostate, malignant melanoma, cholangiocarcinoma, thymoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. In addition, treatment of other metastatic diseases can be monitored by the methods provided herein.

The methods for detecting colonization or replication of a biological therapeutic provided herein, such as an oncolytic virus or adoptive immunotherapy, can be used to detect the presence of tumors or tumor cells, including circulating tumor cells and metastasizing cells. Metastasis involves the formation of progressively growing tumor foci at sites secondary to a primary lesion (Yoshida et al. (2000) *J. Natl. Cancer Inst.* 92(21):1717-1730; Welch et al. (1999) *J. Natl. Cancer Inst.* 91:1351-1353) and is a major cause of morbidity and mortality in human malignancies (Nathoo et al. *J. Clin. Pathol.* 58:237-242 (2005); Fidler et al. *Cell* 79:185-188 (1994)). In vivo metastasis follows a series of steps known as the metastatic cascade, in which tumor cells invade local tissue, intravasate through the bloodstream or lymphatics as emboli or single tumor cells (i.e. circulating tumor cells (CTCs)), and are transported to secondary sites, where they can lodge into the microvasculature and form metastatic lesions (Kauffman et al. *J. Urology* 169:1122-1133 (2003).

Circulating tumor cells were first observed in blood samples of deceased patients with advanced cancers as early as 1869 (Ashworth (1869) *Aust Med J* 14:146-149). More recently, studies on clinical samples, particularly in breast, colon and prostate cancer patients, have shown a correlation between the presence of CTCs in the peripheral blood and cancer prognosis. Detection of CTCs is predictive of metastatic disease, and the quantity of CTCs detected correlates with the severity of metastatic disease. The presence of CTCs in patient samples after therapy also has been associated with tumor progression and spread, poor response to therapy, relapse of disease, and/or decreased survival over a period of several years. Detection of CTCs can provide a means for early detection and treatment of metastatic disease and monitoring of disease therapy.

Because circulating tumor cells (CTCs) have the potential to form tumors and their quantity in circulation correlates with metastatic disease, the ability to accurately identify and quantify CTCs in patient samples would aid in the early diagnosis and prognosis of many types of cancers and the monitoring of cancer treatments. Effective detection of CTCs in bodily samples, such as in the blood, lymph or other bodily fluids, also would aid in staging of particular tumors and evaluating metastatic activity.

Detection of proteins produced by and, secreted by cells containing, the biological therapeutic can be used as a simple marker to indicate cell survival. Genetically altered cells secrete active enzyme as long as they are viable. A small number of cells is sufficient for detection and the amount of reporter protein in the blood correlates with the amount of cells producing the enzyme. Therefore, cell therapies and tissue regeneration are monitored by the methods herein. The detection of cell surface associated reporter protein can aid in studies relying on transfection of cells or following bacteria or parasite infections in which blood-borne pathogens express a membrane- or cell-wall-anchored reporter protein. Also, non-membrane passing prodrug therapies benefit from detection of a reporter protein, such as β-glucuronidase in the blood as the reporter protein is only observed upon successful prodrug treatment as only then, the active protein is released from the tumor. Other benefits and applications of the methods provided herein will be apparent to the skilled artisan and are contemplated herein.

A tumor or metastasis can be detected by physical examination of subject, laboratory tests, such as blood or urine tests, imaging and genetic testing, such as testing for gene mutations that are known to cause cancer. For example, a tumor or metastasis can be detected using in vivo imaging techniques, such as digital X-ray radiography, mammography, CT (computerized tomography) scanning, MRI (magnetic resonance imaging), ultrasonography and PET (positron emission tomography) scanning. Alternatively, a tumor can be detected using tumor markers in blood, serum or urine, that is by monitoring substances produced by tumor cells or by other cells in the body in response to cancer. For example, prostate specific antigen (PSA) levels are used to detect prostate cancer in men. Additionally, tumors can be detected and monitored by biopsy.

The effectiveness of a biological therapy for treatment of a tumor can be externally monitored (e.g., external measurement of tumor size) or by monitoring the animal (e.g., monitoring animal weight, blood panel, antibody titer, spleen size, or liver size). Any of a variety of monitoring steps can be used to monitor a biological therapeutic, including, but not limited to, monitoring tumor size, monitoring anti-(tumor antigen) antibody titer, monitoring the presence and/or size of metastases, monitoring the subject's lymph nodes, monitoring the subject's weight or other health indicators including blood or urine markers, monitoring anti-(microorganism antigen) antibody titer, monitoring expression of a detectable gene product, and directly monitoring titer of a microorganism, such as a virus, in a tumor, tissue or organ of a subject.

F. Examples

The following examples are included for illustrative purposes only and are not intended to limit the scope of the invention.

Example 1

Vaccinia Viruses

A. GLV-1668

The attenuated vaccinia virus strain GLV-1h68 (SEQ ID NO:90), encoding β-galactosidase and β-glucuronidase, was purified as previously described (Zhang et al., (2007) *Cancer Res* 67:10038-10046). This genetically engineered strain, which has been described in U.S. Patent Publication No. 2005/0031643, contains DNA insertions in the F14.5L, thymidine kinase (TK) and hemagglutinin (HA) genes. GLV-1h68 was prepared from the vaccinia virus strain designated LIVP (a vaccinia virus strain, originally derived by adapting the vaccinia Lister strain (ATCC Catalog No. VR-1549) to calf skin (Research Institute of Viral Preparations, Moscow, Russia, Al'tshtein et al. (1983) *Dokl. Akad. Nauk USSR* 285: 696-699). The LIVP strain, whose genome sequence is set forth in SEQ ID NO: 91 and from which GLV-1h68 was generated, contains a mutation in the coding sequence of the TK gene, in which a substitution of a guanine nucleotide with a thymidine nucleotide (nucleotide position 80207 of SEQ ID NO: 91) introduces a premature STOP codon within the coding sequence.

As described in U.S. Patent Publication No. 2005/0031643 (see particularly, Example 1 of the application), GLV-1h68 was generated by inserting expression cassettes encoding detectable marker proteins into the F14.5L (also designated in LIVP as F3) gene, thymidine kinase (TK) gene, and hemagglutinin (HA) gene loci of the vaccinia virus LIVP strain. Specifically, an expression cassette containing a Ruc-GFP cDNA (a fusion of DNA encoding *Renilla* luciferase and DNA encoding GFP; SEQ ID NO:92) under the control of a vaccinia synthetic early/late promoter $P_{SEL}$ was inserted into the F14.5L gene; an expression cassette containing DNA encoding beta-galactosidase (vector psC65; SEQ ID NO:106) under the control of the vaccinia early/late promoter $P_{7.5k}$ (denoted ($P_{7.5k}$)LacZ) and DNA encoding a rat transferrin receptor positioned in the reverse orientation for transcription relative to the vaccinia synthetic early/late promoter $P_{SEL}$ (denoted ($P_{SEL}$)rTrfR) was inserted into the TK gene (the resulting virus does not express transferrin receptor protein since the DNA encoding the protein is positioned in the reverse orientation for transcription relative to the promoter in the cassette); and an expression cassette containing DNA encoding β-glucuronidase (pLacGus Plasmid; SEQ ID NO:107) under the control of the vaccinia late promoter $P_{11k}$ (denoted ($P_{11k}$)gusA) was inserted into the HA gene. Insertion of the expression cassettes into the LIVP genome to generate the GLV-1h68 strain resulted in disruption of the coding sequences for each of the F14.5L, TK and HA genes; accordingly, all three genes in the resulting strains are non-functional in that they do not encode the corresponding full-length proteins.

An additional gusA encoding virus used was GLV-1h80, a derivative of GLV-1 h68, in which the lacZ gene was replaced by the murine MCP-1 gene under control of the promoter $P_{SL}$ (see Table 4 below).

Recombinant viruses were generated by transformation of shuttle plasmid vectors using the FuGENE 6 transfection reagent (Roche Applied Science) into CV-1 cells, which were preinfected with the LIVP parental virus or one of its mutant derivatives. The expression of RUC-GFP fusion protein by the recombinant viruses was confirmed by luminescence assay and fluorescence microscopy. Expressions of β-galactosidase and β-glucuronidase A were confirmed by blue plaque formation upon addition of 5-bromo-4-chloro-3-indolyl-h-D-galactopyranoside (X-gal, Stratagene) and 5-bromo-4-chloro-3-indolyl-h-D-glucuronic acid (X-GlcA, Research Product International Corporation), respectively. Positive plaques formed by the recombinant virus were isolated and purified. The clonal purity each mutant virus isolate was verified by expression of the corresponding marker gene(s) in the F14.5L, J2R, and A56R loci, which was also confirmed by PCR and DNA sequencing. Viruses were propagated in CV-1 cells, and up to $7 \times 10^9$ plaque-forming unit (pfu)/mL of GLV-1h68 can be purified from $2 \times 10^8$ infected CV-1 cells through sucrose gradients (Joklik W K (1962) *Virology* 18:9-18).

B. Generation of Control Viruses rVACV-LacZ⁻ and rVACV-gusA⁻

For generation of control viruses, lacZ and gusA of GLV-1h68 were replaced by nonrelevant gene constructs to create viruses negative for beta-galactosidase (rVACV-LacZ⁻) and beta-glucuronidase (rVACV-gusZ⁻) respectively. The rVACV-LacZ⁻ virus strain was GLV-1h143, in which the lacZ gene was replaced by the human Cyp11B2 gene (see, U.S. Pat. Pub. No. 2009/0117034). The rVACV-GusA⁻ virus strains that were used were either GLV-1h90 (gusA replaced by Hyper-IL-6 encoding gene; see, U.S. Pat. Pub. Nos. 2009/0098529 and 2009/0053244) or GLV-1h189 (gusA replaced by gene encoding the TurboFP635 encoding gene). Viruses were propagated in CV-1 cells were purified through sucrose gradients (Joklik WK (1962) *Virology* 18:9-18).

TABLE 4

Generation of engineered vaccinia viruses.

| Name of Virus | Parental Virus | Genotype |
|---|---|---|
| GLV-1h68 | — | F14.5L: ($P_{SEL}$)Ruc-GFP<br>TK: ($P_{SEL}$)rTrfR-($P_{7.5k}$)LacZ<br>HA: ($P_{11k}$)gusA |
| GLV-1h80 | GLV-1h68 | F14.5L: ($P_{SEL}$)Ruc-GFP<br>TK: ($P_{SLL}$)mMCP-1<br>HA: ($P_{11k}$)gusA |
| GLV-1h90 | GLV-1h68 | F14.5L: ($P_{SEL}$)Ruc-GFP<br>TK: ($P_{SEL}$)rTrfR-($P_{7.5k}$)LacZ<br>HA: ($P_{SE}$)sIl-6R/IL-6 |
| GLV-1h143 | GLV-1h68 | F14.5L: ($P_{SEL}$)Ruc-GFP<br>TK: ($P_{SE}$)CYP11B2<br>HA: ($P_{11k}$)gusA |
| GLV-1h189 | GLV-1h68 | F14.5L: ($P_{SEL}$)Ruc-GFP<br>TK: ($P_{SEL}$)rTrfR-($P_{7.5k}$)LacZ<br>HA: ($P_{SEL}$)FUKW |

C. Activity

Heterologous gene expression of the described vaccinia virus strain was confirmed by Western blot analysis as well as immuno-staining studies in cell culture and infected tumor sections, as described in Example 2 below. The assay was tested with purified enzyme as well as with samples from vaccinia virus injected animals. Marker gene expression of β-galactosidase, β-glucuronidase and Ruc-GFP in cell culture was determined by Western Blot analysis at 6, 12, 24 and 48 hours post A549 cell infection (multiplicity of infection (MOI) of 0.5), with expression of β-galactosidase observed at 12, 24 and 48 hours for GLV-1h68 and rVACV-gusA⁻ and β-glucuronidase observed at 12, 24 and 48 hours for GLV-1h68 and rVACV-LazZ⁻ GLV-1h68 encodes both beta-galactosidase and beta-glucuronidase, while rVACV-LacZ⁻ only encodes beta-glucuronidase and rVACV-gusA⁻ only encodes beta-galactosidase. In viral plaques, GLV-1h68 and rVACV-gusA⁻ were positive for beta-galactosidase activity and GLV-1h68 and rVACV-LazZ⁻ were positive for beta-glucuronidase activity.

Example 2

Materials and Methods

In this example, various materials and methods are described.

Cell Culture

Human A549 lung cancer cells (ATCC No. CCL-185) were cultured in RPMI-1640 medium containing 10% fetal bovine serum (FBS) and 1% antibiotic-antimycotic solution (PAA Laboratories, Cölbe, Germany) under standard cell culture conditions (37° C., 5% $CO_2$). MTH52c, derived from a malignant small-cell canine carcinoma of the mammary gland (Sterenczak et al., (2009) *Gene* 434:35-42), was cultured in DMEM supplemented with antibiotic-antimycotic solution and 20% FBS.

Infection of Cell Cultures

Two days before infection, cells were seeded in 6-well plates for western blot analysis or 12-well plates containing sterile cover slips for microscopy studies. 90% confluent cell layers were either mock treated or infected with GLV-1h68, rVACV-LacZ⁻ or rVACV-GusA⁻ (described in Example 1 above) at a multiplicity of infection (MOI) of 0.1 for 1 h at 37° C. and 5% CO2 in medium containing 2% FBS. Afterwards the infection medium was aspirated and replaced by standard cell culture medium.

Western Blot

For detection of proteins, infected cells were harvested and lysed in SDS sample buffer at 6, 12, 24 and 48 hours post-infection (hpi). Lysates were separated by 10% SDS-polyacrylamide gel electrophoresis and subsequently transferred onto a nitrocellulose membrane (Whatman GmbH, Dassel, Germany). After blocking in 5% skim milk in PBS, the membrane was incubated with anti-beta-glucuronidase rabbit polyclonal antibody (G5420, Sigma-Aldrich, Schnelldorf, Germany), anti-beta-galactosidase rabbit polyclonal antibody (A-11132, Molecular Probes, Leiden, Netherlands), anti-GFP rabbit polyclonal antibody (sc-8334, Santa Cruz, Heidelberg, Germany) or anti-beta-actin mouse monoclonal antibody (ab6276, Abcam, Cambridge, UK). The first antibodies were detected using horseradish peroxidase-conjugated anti-mouse (ab6728, Abcam, Cambridge, UK) or anti-rabbit (ab6721, Abcam, Cambridge, UK) secondary antibodies, followed by enhanced chemiluminescence detection.

X-Gal/X-GlcU Staining and Microscopy Studies

For the analysis of expression and activity of beta-galactosidase and beta-glucuronidase respectively, A549 cells were seeded on coverslips and infected with 200 pfu (plaque forming units) GLV-1h68, rVACV-LacZ⁻ or rVACV-GusA⁻ per well. After incubation for 2 days, cells were fixed using 4% paraformaldehyde and washed twice in PBS. Staining solutions contained of 40 µl X-Gal (5-bromo-4-chloro-3-indolyl-β-D-galactoside, Invitrogen, Karlsruhe, Germany) and X-GlcU (5-bromo-4-chloro-3-indolyl-β-D-glucuronide, Invitrogen, Karlsruhe, Germany) respectively in dimethylformamide (40 mg ml-1), ferricyanide (12 mM $K_3Fe(CN)_6$), 5.2 mM $MgCl_2$ and ferrocyanide solution (12 mM $K_4Fe(CN)_6$). Coverslips were stained with either X-Gal or X-GlcU solution and incubated for 24 h at 37° C. before mounting in Mowiol. Images were taken with a Zeiss Axiovert 200M microscope.

Histology and Immunofluorescence

For histological analysis, snap-frozen tumors were fixed in 4% paraformaldehyde/PBS overnight at 4° C. Samples were embedded in 5% (w/v) low-melt agarose (AppliChem, Darmstadt, Germany) and 100 µm sections were cut using a Leica VT1000S Vibratome (Leica, Heerbrugg, Switzerland) as described before (Stritzker et al., (2007) *Int J Med Microbiol* 297-151:162). After permeabilizing in 0.3% Triton X-100/PBS, sections were incubated with Hoechst 33342, anti-beta-glucuronidase rabbit polyclonal antibody (G5420, Sigma-Aldrich, Schnelldorf, Germany) and anti-beta-galactosidase chicken polyclonal antibody (ab9361, Abcam, Cambridge, UK) before staining with Cy-5-conjugated donkey anti-rabbit and Cy-3 conjugated donkey anti-chicken secondary antibodies (Jackson ImmunoResearch, West Grove, Pa.). Mowiol-embedded sections were examined using a Leica MZ 16 FA Stereo-Fluorescence Microscope equipped with a Leica DC500 Digital Camera. Digital Images were processed with Photoshop 7.0 (Adobe Systems, San Jose, Calif.)and merged to yield pseudocolored pictures.

Generation of Xenograft Tumors in Mice—Animal Studies

A549 and MTH52c xenograft tumors were developed in 6- to 8-week-old nude mice (NCI:Hsd:Athymic Nude Foxnl$^{nu}$, Harlan Borchem, Germany) by implanting $5 \times 10^6$ cells subcutaneously in the right abdominal flank. Two to three weeks after implantation, tumor bearing mice were anesthetized with isoflurane and injected i.v. with either PBS or virus, as described below. Blood and urine collection of mice was carried out under anesthesia by a heparinised capillary pipette (No. 554/20, Assistant, Sondheim, Germany) via the retro-orbital sinus vein and a bladder catheter (No. 381312, Becton Dickinson, Heidelberg, Germany) for blood and urine respectively.

All animal experiments were carried out in accordance with protocols approved by the Regierung von Unterfranken (Würzburg, Germany) (protocol number AZ 55.2-2531.01-17/08) and/or the Institutional Animal Care and Use Committee (IACUC) of Explora BIOLABS, located in San Diego Science Center (San Diego, USA) (protocol number: EB08-003).

Fluorogenic Probes and Detection of Fluorescence Products

The lyophilized fluorogenic probes fluorescein di-beta-D-glucuronide (FDGlcU), Fluorescein di-β-D-galactopyranoside (FDG) and 4-Methylumbelliferyl-b-D-glucuronide (4-MUG) (Invitrogen, Karlsruhe, Germany) were dissolved in DMSO (36.5 mM). For in vivo studies, 5 µL of each stock dilution was mixed with 195 µL PBS and injected intraperitoneally. Whole body and urine fluorescence analysis was performed using a Maestro EX imaging system (CRI, Woburn, Mass.). For serum analysis, the collected mouse serum was diluted 1:15 with PBS and 80 µL of each sample were mixed with of either 2.5 µg FDGlcU or 1.5 µg 4-MUG if not otherwise indicated. Human serum of healthy individuals (Zen-Bio Inc, Research Triangle, N.C.) was obtained from whole blood and 10 µL were used in the described assay. After incubation for 1 h at 37° C. (if not otherwise indicated), fluorescence was read in Lumox 384-well plates (Sarstedt, Nümbrecht, Germany) using an Infinite 200 Pro Microplate Reader (Tecan, Crailsheim, Germany) or a Spectra Max M5 (Molecular Devices, Sunnyvale, USA) and fluorescence intensities are listed as relative fluorescence units.

Example 3

Fluorogenic Compound Activation in rVACV-Colonized Tumors

In this example, the activation and pharmacokinetics of beta-galactosidase and glucuronidase substrates, Fluorescein di-β-D-galactopyranoside (FDG; substrate for the beta-galactosidase LacZ; Invitrogen) and fluorescein di-beta-D-glucuronide (FDGlcU; a glucuronidase substrate; Invitrogen) in rVACV-colonized tumors was determined.

FDG or FDGlcU (5 µL of 36.5 mM stock solution in 195 µL PBS) were intraperitoneally injected into tumor bearing mice that had previously been injected via retro-orbital sinus vein with $5 \times 10^6$ pfu of oncolytic rVACV (GLV-1h68) encoding β-galactosidase and β-glucuronidase. Animals that were previously injected with PBS or $5 \times 10^6$ pfu of control rVACV strains not expressing β-galactosidase (rVACV-LacZ⁻) and β-glucuronidase (rVACV-GusA⁻) respectively served as controls. Fluorescein, which resulted upon cleavage of either substrate, was detected using a small animal fluorescence imaging system.

Figure 2:
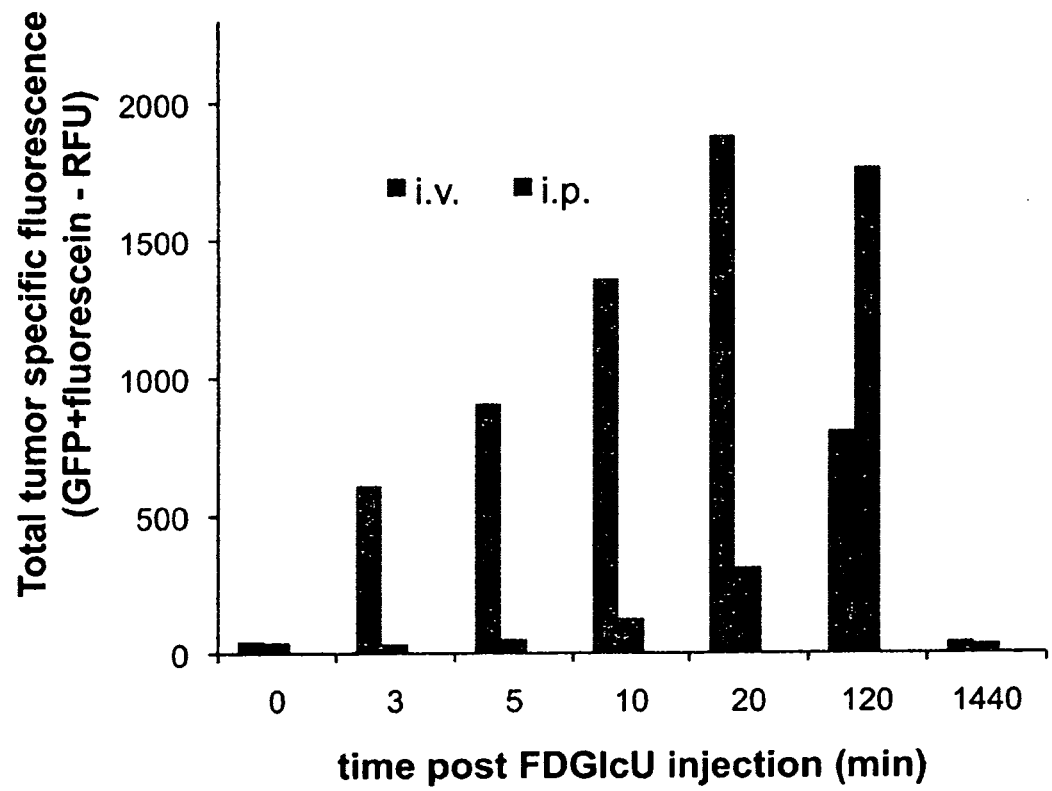
FIG. 2. Time dependent conversion of FDGlcU in the same mouse injected with GLV-1h68. An A549 Tumor-bearing mouse was injected with GLV-1h68 10 days before FDGlcU injection was performed. Intraperitoneal (i.p.) injection (lower row pictures) occurred 24 hours before intravenous (i.v.) injection (upper row pictures). This allowed the fluorescence signal to decline completely before getting the kinetics in the very same mouse.

The results show that FDG and FDGlcU were activated in the tumor, and activation was dependent on the expression of LacZ and GusA respectively. As shown in FIG. 1, maximum fluorescence in the tumor was observed 120 min after intraperitoneal injection. As shown in FIG. 2, maximum fluorescence upon intravenous FDGlcU-injection was observed 20 min post injection. Further, about 6 hours post injection (hpi), the GFP-dependent fluorescence remained while most of the compound specific fluorescence was gone.

Example 4

Analysis of Urine Samples from FDGlcU Injected Mice

In this example, urine was examined for the presence of fluorescein resulting from cleavage of fluorogenic substrates by GLV-1h68. The results show that fluorescein was detected in the urine of mice previously injected with GLV-1h68. Additionally, direct injection of fluorescein into the tumor resulted in an accumulation of fluorescein in the bladder, and subsequent secretion of the fluorescein with the urine, in addition to the disappearance of fluorescein from the tumor.

The presence of the fluorescein in the urine of GLV-1h68 injected tumor bearing mice was evaluated as a biomarker for successful tumor colonization by the virus. Mice that were injected with either PBS (control, non-colonized) or with GusA-negative control-virus (GLV-1h188) or GusA-positive (GLV-1h68) were anesthetized and urine was isolated via a bladder catheter before and 90 minutes after i.p. injection of FDGlcU. Urine fluorescence analysis on 5 µL of urine was performed using a Maestro EX imaging system (CRI, Woburn, Mass.).

Figure 3:
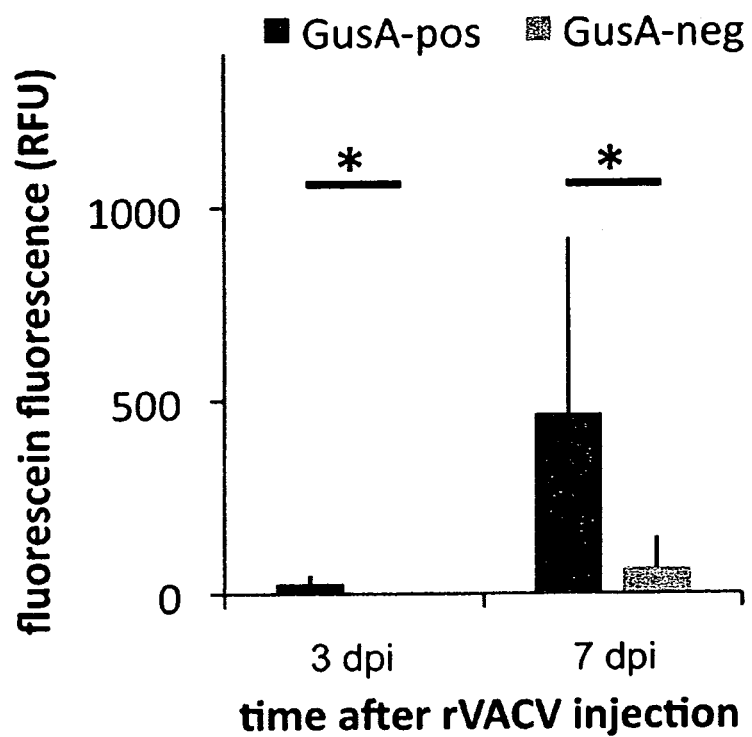
FIG. 3. Analysis of urine samples derived from mice before, 30 min and 90 min post FDGlcU injection respectively. Three and seven days post rVACV injection urine was sampled before and 90 min post FDGlcU injection. Average plus standard deviation of fluorescein specific fluorescence of GusA-positive (n=6 for 3 dpi and n=8 for 7 dpi) and GusA-negative (n=4) rVACV colonized tumors. * indicates p<0.05.

As shown in FIG. 3, fluorescein was observed in the urine of GLV-1h68 treated tumor bearing animals but was not observed in FDGlcU injected mice that had either non-colonized or rVACV-GusA⁻ colonized tumors. Thus, the presence of GLV-1h68 in tumors of live mice was determined with a simple urine test after systemic injection of FDGlcU.

Example 5

Evaluation of β-Glucuronidase Specific Fluorogenic Compound Activation in Serum of A549 Tumor Bearing Mice A. β-Glucuronidase Specific Fluorogenic Compound Activation in Serum of Tumor Bearing Mice In this example, the presence of active β-glucuronidase in the serum of GLV-1h68 injected tumor bearing mice was determined by 1) addition of fluorogenic compound FDGlcU or 4-Methylumbelliferyl-b-D-glucuronide (4-MUG; Invitrogen) to the serum; and 2) detection of fluorescence. To this end, the 5 µL serum of tumor bearing mice that were previously injected with GLV-1h68 was diluted with PBS to 75 µL and was incubated with either 2.5 µg FDGlcU or 1.5 µg 4-MUG (diluted in 5 µL), both of which are hydrolyzed by β-glucuronidase to the fluorescent products fluorescein and 4-methylumbelliferone (4-MU) respectively. Serum of tumor bearing mice that were injected with either PBS or a GusA-negative control rVACV were used as negative controls. Fluorescence was determined as described in Example 2 and was reported as relative fluorescence units (RFU). 4-MUG was determined at an excitation wavelength of 365 (9) nm and an emission wavelength of 455 (20) nm. FDGlcU was determined at an excitation wavelength of 489 (9) nm and an emission wavelength of 520 (20) nm.

Figure 4:
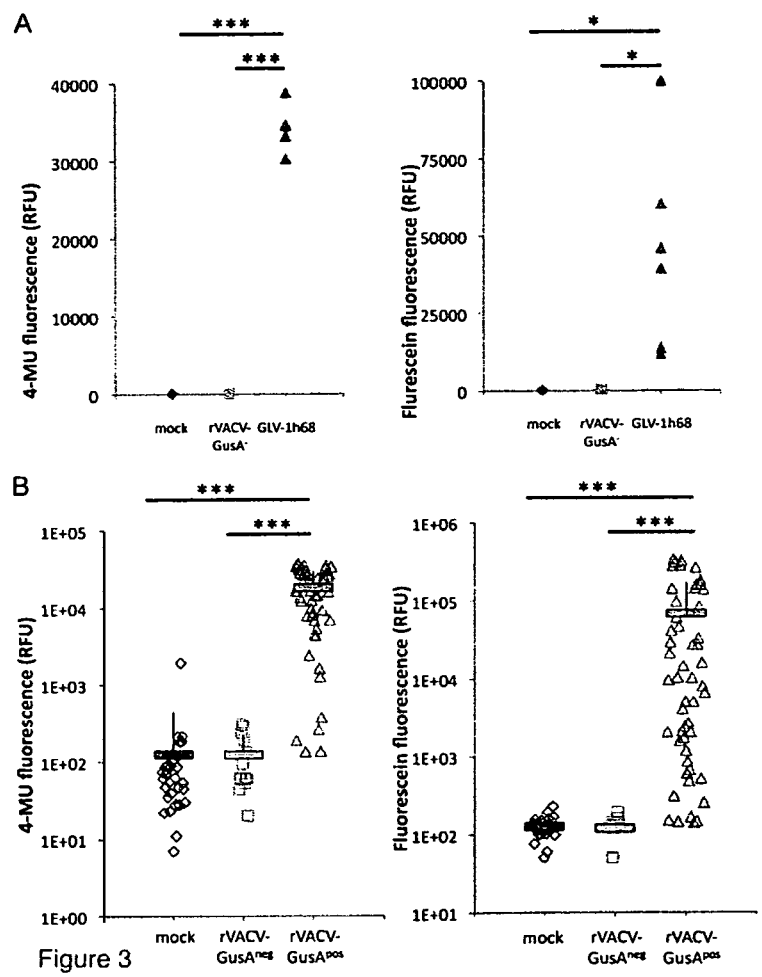
FIG. 4. Glucuronidase specific fluorogenic compound activation in serum of tumor bearing mice.

The results show that no fluorescence was observed when mice were injected with either PBS or GusA-negative control rVACV while fluorescence was detected for both fluorogenic compounds when mice were injected with GusA-positive GLV-1h68 (see FIG. 4A). Beta-glucuronidase is not secreted (no secretion signal) after production. In order to get out of the cells and into the serum, the host cell must lyse. Subsequently, the enzyme is shed to the serum. Thus, the serum contained active (non-secreted, but shed) enzymes that were produced in the tumor tissues.

B. β-Glucuronidase Specific Fluorogenic Compound Activation in Serum of Tumor Bearing Mice In this example, the assay was used to confirm the applicability of the method using a larger number of samples and different tumor models. Serum samples (n=99) that were previously collected over a 4 year period of time from different mouse tumor xenograft models, including those containing GI-101A, A549, DU-145, PANC-1 and HT-29 tumors, were analyzed for β-glucuronidase activity. The mice had previously been injected with PBS (n=33) or had previously been injected at 5×10⁶ pfu with several GusA-positive (n=53, GLV-1h68, GLV-1h80 (derived from GLV-1h68 containing MCP-1 gene instead of lacZ) or GusA-negative (n=13, GLV-1h90, GLV-1h43) rVACV strains virus for different periods of time (from 7 to 53 days). The serum was diluted 1:15 with PBS and 75 µL of each sample were mixed with either 2.5 µg FDGlcU or 1.5 µg 4-MUG (both in 5 µL) and fluorescence was determined as described in Example 2 and was reported as relative fluorescence units (RFU).

As shown in FIG. 4B, a significant (p<0.001) difference was observed between the serum from tumor bearing mice treated with GusA-positive rVACV strains (average 4-MU or fluorescein in RFU of approximately $1\times10^4$ or $1\times10^5$, respectively) and control mice that were treated with GusA-negative rVACV strains that do not express β-glucuronidase or PBS (average 4-MU in RFU of approximately $1\times10^2$).

Example 6

Blood Test to Determine Successful Tumor Colonization

In this example, the assay was demonstrated to be a way to determine tumor colonization of GusA-encoding oncolytic virus strains in mice.

Tumor bearing mice (n=6) were systemically injected with a low dose ($1\times10^5$ PFU) of GLV-1h68. This dose was selected as it has previously been shown to result in colonization of some tumors, while other tumors are not colonized. Serum was isolated 1, 3, 7, 10 and 14 days post injection and fluorescence was determined as described above. Mice were sacrificed at day 14 and tumor colonization was tested by conventional plaque assay.

After 14 days, sera from two mice (#482 and #486) generated high 4-MU fluorescence (RFU of approximately 50,000 and 10,000 respectively) while the sera of the remaining mice did not generate fluorescence when tested. As stated above, the dose of GLV-1h68 was selected as it has previously been shown to result in colonization of some tumors, while other tumors are not colonized. Viral titer analysis revealed that only the same two mice (#482 and #486) had virus colonized tumors. Thus, there was positive correlation between the positive FDGlcU/4-MUG based blood tests and virus colonized tumors.

Example 7

Suitability of the Blood Test for Glucuronidase Activity to Differentiate Between Tumor Bearing and Tumor Free Mice In this example, the suitability of the blood test to differentiate between tumor bearing and control tumor free mice is shown. In addition, background levels of glucuronidase activity were determined.
A. GLV-1h68 Induced Glucuronidase Activity in Tumor Versus Tumor-Free Mice Tumor bearing mice (n=5, Mice #7-11) and non-tumor bearing mice (n=6, Mice #1-6) were injected with 5×10⁶ pfu of GLV-1h68 in the retro-orbital sinus vein. Seven (7) days post infection blood was drawn and serum was tested for glucuronidase activity upon the addition of 4-MUG or FDGlcU.

Analysis of sera revealed conversion of the fluorogenic compounds FDGlcU and 4-MUG in all tumor bearing mice seven days post infection. Low but evident glucuronidase activity was also detected in the serum of non-tumor bearing mice after seven days post infection. Closer examination of the non-tumor bearing mice revealed GFP expression in the paws of 2 mice (mice #1 and #4).

The mice were sacrificed on day 14 and a conventional plaque assay of several organs was used to find the origin of glucuronidase production. The results of the plaque assay are set forth in Table 5 below. Apart from the two infected paws, virus was reproducibly isolated in low concentration from ovaries of non-tumor bearing mice (mice #1-#5). In contrast, ovaries of tumor bearing mice were essentially free of virus. The data show significant viral distribution in the tumors of mice #7 to #11.

Aldrich: One Sigma or modified "Fishman" unit will liberate 1.0 µg of phenolphthalein from phenolphthalein glucuronide per hr at 37° C. at pH 5.0; pH 6.8 for the *E. coli* source; 30 min assay) was incubated with fluorogenic substrate (4-MUG: 0, 0.094, 0.188, 0.375, 0.75, 1.5, 3, 6 and 12 µg; or FDGlcU: 0, 0.156, 0.312, 0.625, 1.25, 2.5, 5, 10 and 20 µg) for an incubation time of 15, 30, 60, 120 and 1080 minutes.

TABLE 5

Viral distribution in tumor bearing and non-tumor bearing mice 14 days post infection

| | pfu/g tissue | | | | | | | | | fluorescence | |
|---|---|---|---|---|---|---|---|---|---|---|---|
| mouse # | tumor | blood | ovaries | spleen | kidneys | liver | lung | brain | paw | 4-MU | fluorescein |
| 1 | NA | ND | ND | ND | ND | ND | ND | ND | 2.10E+06 | 8599 | 1179 |
| 2 | NA | ND | 2500 | ND | ND | ND | ND | 100 | ND | 4418 | 607 |
| 3 | NA | ND | 5300 | ND | ND | ND | ND | 20 | ND | 6775 | 855 |
| 4 | NA | ND | 12000 | ND | 100 | ND | ND | ND | 5.00E+05 | 14587 | 2641 |
| 5 | NA | ND | 8800 | ND | ND | 100 | ND | ND | ND | 4325 | 483 |
| 6 | NA | ND | ND | ND | ND | 0 | ND | ND | ND | 5272 | 667 |
| 7 | 2.70E+07 | ND | ND | 40 | ND | ND | 20 | ND | ND | 40812 | 168977 |
| 8 | 5.15E+07 | ND | ND | 100 | ND | ND | ND | ND | ND | 43732 | 61137 |
| 9 | 2.65E+07 | ND | ND | ND | 100 | ND | ND | ND | ND | 43866 | 43572 |
| 10 | 9.00E+06 | ND | 20 | 20 | 100 | ND | 80 | ND | ND | 38449 | 135454 |
| 11 | 8.50E+06 | ND | ND | ND | 20 | ND | ND | ND | ND | 41645 | 28754 |

NA—not applicable.
ND—not detectable. Detection limit 20 pfu/g.

B. Background Expression of Glucuronidase Activity

Time course studies were performed in male (n=12 tumor bearing and 12 tumor free) and female mice (n=24 tumor bearing and 6 tumor free) injected with $5\times10^6$ pfu GLV-1h68. Blood was collected every other day over a period of 14-16 days (in one half of the mice blood was taken on even days, in the other half, blood was taken on uneven days post virus injection). 4-MUG or FDGlcU were added and the serum was examined for glucuronidase activity by measuring the fluorescence as described in Example 2.

Glucuronidase activity was present in the serum of tumor-bearing mice. The results also showed low levels of glucuronidase present in the serum of tumor free mice. The results for non-tumor bearing mice were similar to those observed in tumor bearing mice until 8 days post virus injection, after which time changes were observed between the two groups. At day 8, the glucuronidase activity in the serum of tumor free mice decreased while the glucuronidase activity in the serum of tumor bearing mice increased, as observed by an increase in RFU. Significant differences ($p<0.05$) were detected between tumor bearing and non-tumor beating mice after 9 days post infection. Taken together, 9 days after injection of the virus, it was possible to determine with confidence whether A) an existing tumor was successfully colonized and/or B) a tumor was present in the gusA encoding rVACV injected mouse, as evidenced by the presence of β-glucuronidase activity in serum samples.

Example 8

Assay Sensitivity

In this example, sensitivity of the assay was determined using in vitro studies that measured the correlation between fluorescence signal intensity and increasing glucuronidase concentration, fluorogenic substrate concentration and incubation time. In addition, the effect of the presence of human serum on the assay was evaluated.
A. Assay Sensitivity

Figure 5:
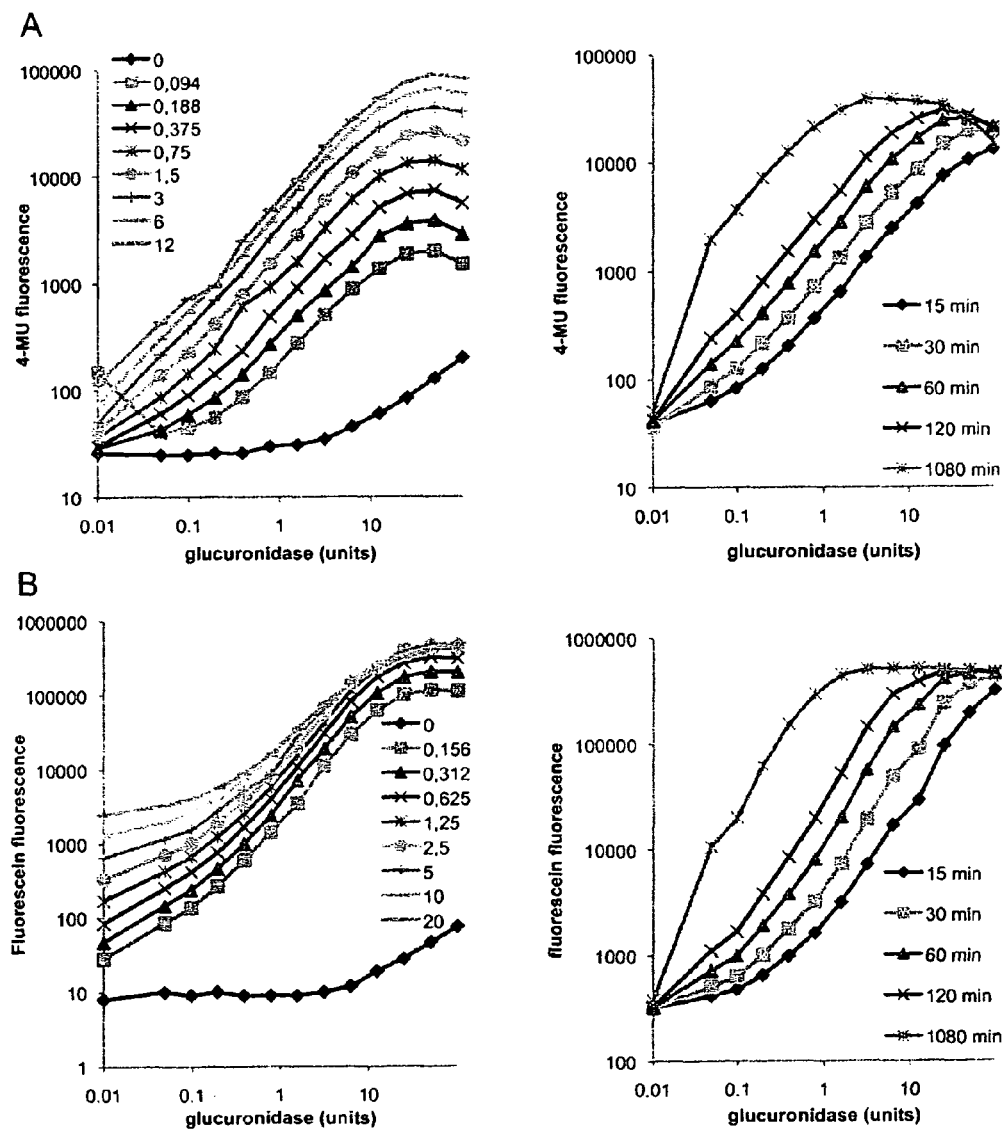
FIG. 5. Positive correlation between the fluorescence signal intensities and increasing glucuronidase concentration, fluorogenic substrate concentration (left panels, 4-MUG in FIG. 5A. FDGlcU in FIG. 5B. and incubation time (right panels).

*Helix pomatia* glucuronidase (Sigma Aldrich, #G0751; 0, 0.049, 0.098, 0.195, 0.391, 0.781, 1.563, 3.125, 6.25, 12.5, 25.0, 50.0 and 100.0 units; unit definition according to Sigma The results are set forth in FIG. 5 for substrate concentration (left panels) and incubation time (right panels). A positive correlation was observed between the fluorescence signal intensities and increasing A) glucuronidase concentration, B) substrate (FDGlcU or 4-MUG) concentration and C) incubation time. The data also revealed that very low glucuronidase concentrations can be detected using the fluorogenic FDGlcU or 4-MUG substrates (0.156 and 0.094 units respectively). This permits detection of lysed tumor cells not only in mice but also in humans.
B. Effect of Human Serum on Assay The assay in the presence of human serum was shown by co-incubating increasing amounts of *E. coli* glucuronidase (0.000141, 0.000445, 0.00141, 0.00445, 0.0141, 0.0445, 0.141, 0.445, 1.41, 4.45, 14.1, 44.5, 445 ng) and either 4-MUG or FDGluC in the presence or absence of 10 µL human serum The data revealed that neither the sensitivity nor the fluorescence intensity of the assay was changed in the presence of human serum.

Example 9

Minimal Amount of Infected Cancer Cells Required for Positive Detection

This example shows the minimal amount of infected cancer cells required to generate a positive fluorescent signal, as the presence of glucuronidase relies on the production by infected cancer cells.

A549 cells were infected at a multiplicity of infection of 2.0 of GLV-1h68 or control-rVACV (rVACV-GusA$^{neg}$). One day later, the number of infected cells was determined by counting and flow cytometry. Subsequently, the cells were diluted and seeded in half-log dilutions in 384-well plates with concentrations varying from approximately 1.0 to 1000 infected cells/well and co-incubated with 6.3 µg FDGlcU and 3.4 µg 4-MUG respectively. To obtain high sensitivity, the probes were incubated at 37° C. overnight and analyzed the next day.

Figure 6:
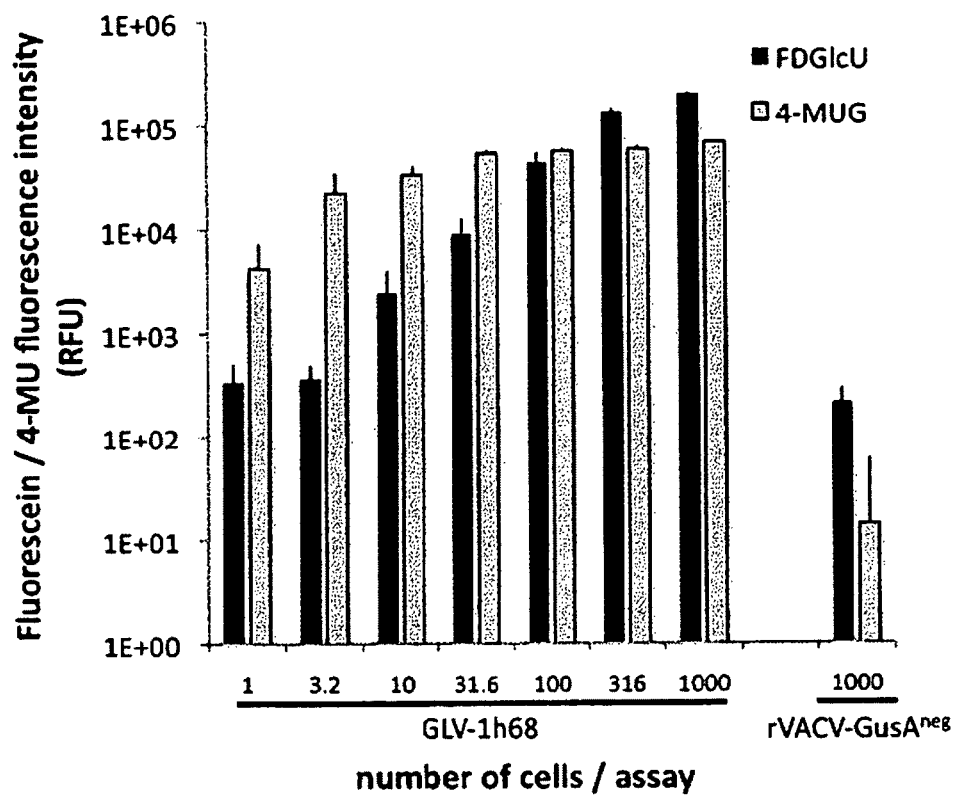
FIG. 6. Minimal amount of GLV-1h68 infected cancer cells necessary for positive detection. A549 cells were infected with GLV-1h68 or control-rVACV (rVACV-GusA$^{neg}$). One day later, the amount of infected cells was determined by flow cytometry and the cells were seeded in half-log dilutions in 384-well plates with concentrations varying from 1.0 to 1000 cells/well and co-incubated with FDGlcU and 4-MUG respectively. Data represent average plus standard deviation (n=6).

The results show that a single cancer cell infected with GLV-1h68 can be detected in the assay when using 4-MUG as a substrate (see FIG. 6). For FDGlcU as a substrate, approximately 10 infected cancer cells were required to distinguish signal over background.

The sensitivity of the described test for the detection of tumors in human patients was determined using two different approaches: 1) Assuming that a greater volume of serum (e.g. 50 µL) is used when testing the system on human patient samples, and considering an average total blood volume of about 4.7 liters, approximately $10^5$ infected cancer cells is sufficient to generate a detectable fluorescent signal. 2) The fluorescent signal generated from a single cancer cell was similar to that obtained from 0.2 units glucuronidase (see Example 8). Increasing the sensitivity by adding more fluorescent substrate resulted in the detection of 0.05 units glucuronidase. This corresponds to a concentration of 1 unit glucuronidase per mL serum (again using 50 µL serum per test) or 4700 units/average blood volume of a human patient. Therefore, as low as $2.4 \times 10^4$ infected cancer cells are sufficient for a positive signal.

Example 10

Other Tumor Colonizing Vectors

In this example, the assay was performed using other exemplary tumor colonizing vectors, namely E. coli Nissle 1917×pBR322DEST$_{inv}$-P$_{S10}$-gusA-luxABCDE (EcN-SgusAL) and E. coli Nissle 1917×pBR322DEST$_{inv}$-P$_{S10}$-luxABCDE-term (EcN-SLT).

E. coli Nissle 1917×pBR322DEST$_{inv}$-P$_{S10}$-gusA-luxABCDE (EcN-SgusAL) is an E. coli strain Nissle 1917 harboring a plasmid encoding β-glucuronidase and lux operon under a Bacillus subtilis rpsJ promoter (P$_{S10}$; GenBank Accession No. U43929; SEQ ID NO:125). E. coli Nissle 1917×pBR322DEST$_{inv}$-P$_{S10}$-luxABCDE-term (EcN-SLT) is an E. coli strain Nissle 1917 harboring a plasmid the lux operon under control of the Bacillus subtilis rpsJ promoter. This bacteria is a control bacteria that does not express β-glucuronidase.

E. coli Nissle 1917×pBR322DEST$_{inv}$-P$_{S10}$-gusA-luxABCDE (EcN-SgusAL) or E. coli Nissle 1917×pBR322DEST$_{inv}$-P$_{S10}$-luxABCDE-term (EcN-SLT) bacteria or PBS were intratumorally (i.t.) injected 2 days before serum analysis. Tumor colonization was shown by bioluminescence imaging. In P$_{S10}$-gusA encoding E. coli Nissle 1917 injected mice, activation of FDGlcU and 4-MUG was observed.

TABLE 6

T-test results for E. coli Nissle assay

|  | T-test Results |
|---|---|
| FDGlcU data |  |
| EcN -SLT vs. EcN -SgusAL | 0.165429222 |
| EcN -SgusAL vs. PBS | 0.192366995 |
| 4-MUG data |  |
| EcN -SLT vs. EcN -SgusAL | 0.251668626 |
| EcN -SgusAL vs. PBS | 0.24295584 |

Example 11

Analysis of Human Serum Samples from Individuals Treated with GLV-1h68

In this example, to monitor therapy, serum samples from cancer patients treated with GLV-1h68 were examined for β-glucuronidase activity.

Patients were treated for one to six 28 day cycles, with intravenous administration at day 1 of each cycle with GLV-1h68 in an amount between $1 \times 10^5$ to $3 \times 10^9$ pfu. Samples were collected at various time points, from 30 minutes to hours, to days. Various serum samples (20 µL) were incubated with 3.75 µg 4-MUG for one hour. Fluorescence was determined using a SpectraMax M5 fluorometer and was reported as relative fluorescence units (RFU). The data show β-glucuronidase activity was present in the serum of 8 of 12 patients tested, indicating that virus colonized tumors and were replicating. Table 7 below indicates glucuronidase activity in picograms. The different cohorts received varying amounts of GLV-1h68 as follows: Cohort 1, $2 \times 10^5$ pfu; Cohort 2, $1 \times 10^6$ pfu; Cohort 3, $1 \times 10^7$ pfu; Cohort 4, $1 \times 10^8$ pfu; Cohort 5, $1 \times 10^9$ pfu; Cohort 5a, $1 \times 10^9$ pfu; Cohort 5b, $3 \times 10^9$ pfu; Cohort 6, $5 \times 10^7$ pfu; and Cohort 7, $5 \times 10^8$ pfu. The results indicate the highest levels of glucuronidase activity were detected in serum on cycle 1, day 8 and day 9.

TABLE 7

Glucuronidase activity in human serum samples

| Cohort | | Cycle 1 | | | | | | | | Cycle 2 | | | | | | | Cycle 3 | | | | Cycle 4 | | Cycle 5 | Cycle 6 |
|---|---|---|---|---|---|---|---|---|---|---|---|---|---|---|---|---|---|---|---|---|---|---|---|---|
| | Screen | 1 | 2 | 3 | 4 | 8 | 9 | 15 | 22 | 1 | 2 | 3 | 4 | 8 | 15 | 22 | 1 | 8 | 15 | 22 | 1 | 15 | 22 | 1 | 1 |
| 1 | P102 | 0 | 1 | | | 0 | | 0 | 0 | 0 | | | | 0 | 0 | 0 | | | 0 | | | | | | |
| 1 | P103 | 3 | 3 | | | 4 | | 4 | 4 | 6 | | | | 5 | 5 | 4 | | | | | | | | | |
| 1 | P201 | 0 | 0 | 0 | | 1 | | 0 | 0 | 0 | | | | 0 | 0 | 0 | | | | | | | | | |
| 2 | P202 | 0 | 0 | | | 0 | | 0 | 0 | 0 | | | | 0 | 0 | 0 | 0 | | | | | | | | |
| 2 | P104 | 0 | 0 | | | 0 | | 0 | 0 | 0 | | | | 0 | 0 | 0 | | | | | | | | | |
| 2 | P105 | 0 | 0 | | | 0 | | 0 | 0 | 0 | | | | 0 | 0 | | | | | | | | | | |
| 3 | P106 | 0 | 0 | 2 | | 245 | | | | | | | | | | | | | | | | | | | |
| 3 | P204 | 1 | 0 | | | 4 | | 2 | 2 | 2 | | | | 3 | 3 | 2 | 2 | | | | | 3 | 1 | 2 | |
| 3 | P109 | 0 | 1 | 0 | | 0 | | 0 | 0 | 0 | 0 | | | 0 | 0 | 0 | | | | | | | | | |
| 4 | P205 | 0 | 0 | | | 1 | | 0 | 3 | 0 | | | | 6 | 5 | 0 | 2 | | | | | | | | |
| 4 | P111 | 0 | 0 | | | 0 | | 0 | 0 | 0 | | | | 0 | 1 | 2 | | | | | | | | | |
| 4 | P112 | 0 | 0 | 0 | | 1 | | 0 | 1 | 1 | 4 | | | 1 | 0 | | 0 | | | | | | | | |
| 5 | P208 | 0 | 0 | | | 0 | | 0 | 0 | 0 | 0 | | | | 0 | 0 | 0 | 0 | 0 | 0 | | | | | |
| 5 | P114 | 0 | | | 0 | 4 | 54 | 1 | 0 | 0 | 0 | 0 | 0 | 0 | 0 | 0 | 1 | | | 0 | | | | 0 | 0 |
| 5 | P116 | 0 | 0 | 0 | | 91 | 157 | 0 | 0 | 0 | | | | 0 | 0 | 0 | | | | 0 | | | | 0 | 0 |
| 5a | P121 | 0 | 0 | | | 2 | | 0 | 0 | | | | | | | | | | | | | | | | |
| 5a | P213 | 1 | 2 | | | 6 | | 3 | 3 | 5 | | | | | | | 0 | | | | | | | | |
| 5a | P215 | | | | | | | | | | | | | | | | | | | | | | | | |

TABLE 7-continued

Glucuronidase activity in human serum samples

| Cohort | | Screen | Cycle 1 | | | | | | | | Cycle 2 | | | | | | | Cycle 3 | | | | Cycle 4 | | Cycle 5 | Cycle 6 |
| --- | --- | --- | --- | --- | --- | --- | --- | --- | --- | --- | --- | --- | --- | --- | --- | --- | --- | --- | --- | --- | --- | --- | --- | --- | --- |
| | | | Day 1 | 2 | 3 | 4 | 8 | 9 | 15 | 22 | 1 | 2 | 3 | 4 | 8 | 15 | 22 | 1 | 8 | 15 | 22 | 1 | 15 | 22 | 1 | 1 |
| 5b | P120 | 0 | 0 | | | | 0 | | 0 | 0 | 0 | | | | 0 | 0 | 0 | 0 | | | | | | | | |
| 5b | P122 | 0 | 0 | | | | 0 | | 0 | 0 | 0 | | | | 0 | 0 | 0 | 0 | | | | | | | | |
| 5b | P216 | 4 | | 9 | 1 | | 17 | | | | | | | | | | | | | | | | | | | |
| 6 | P209 | 0 | 0 | | | | 0 | | 0 | 0 | | | | | 0 | 0 | 0 | 0 | | 0 | | | | | | |
| 6 | P117 | 0 | 0 | | | | 0 | | 1 | 0 | 0 | | | | 0 | | | | | | | | | | | |
| 6 | P212 | 0 | 0 | | | | 0 | | 0 | 0 | 0 | | | | | 2 | | 1 | | | 3 | | | | 2 | |
| 7 | P119 | | 1 | | | | 0 | | 0 | | 5 | | | | 6 | 3 | 1 | 0 | 0 | | 0 | | | | 4 | 0 |
| 7 | P124 | 0 | 0 | | | | 0 | | 0 | 0 | 0 | | | | 0 | 0 | 0 | 0 | | | | | | | | |
| 7 | P125 | 0 | 0 | | | | 0 | | 0 | 0 | 0 | | | | 0 | 0 | 0 | | | | | | | | | |

Since modifications will be apparent to those of skill in this art, it is intended that this invention be limited only by the scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08859256B2). An electronic copy of the "Sequence Listing" will also be available from the USPTO upon request and payment of the fee set forth in 37 CFR 1.19(b)(3).

The invention claimed is:

1. A method for treating cancer and monitoring therapeutic progress in a subject having tumors, said method comprising:
   a) administering to said subject an oncolytic virus encoding a β-glucuronidase, wherein said oncolytic virus targets and treats cancer and the β-glucuronidase activity indicates oncolytic viral colonization or replication in said cancer;
   b) obtaining a sample from a subject, wherein said sample is a body fluid or tissue sample that is not a tumor sample;
   c) detecting β-glucuronidase activity in the sample, wherein said detection is by the addition of a substrate for β-glucuronidase; and
   d) determining the presence of a product catalyzed by the reaction of the β-glucuronidase with the substrate,
   wherein the detection of the product indicates that the oncolytic virus has colonized or is replicating in a tumor tissue or cell in the subject and is treating said tumor tissue or cell and oncolytic viral therapy be continued.

2. The method of claim 1, wherein the oncolytic virus is selected from among an poxvirus, adenovirus, reovirus, herpes virus, adeno-associated virus, lentivirus, retrovirus, rhabdovirus, papillomavirus, vesicular stomatitis virus, measles virus, Newcastle disease virus, picornavirus, sindbis virus, parvovirus, coxsackievirus, influenza virus, mumps virus, poliovirus and semliki forest virus.

3. The method of claim 2 wherein the virus is a poxvirus that is selected from among an orthopoxvirus, parapoxvirus, avipoxvirus, capripoxvirus, leporipoxvirus, suipoxvirus, molluscipoxvirus, yatapoxvirus, entomopoxvirus A, entomopoxvirus B, and entomopoxvirus C.

4. The method of claim 2, wherein the virus is a poxvirus.

5. The method of claim 4, wherein the poxvirus is a vaccinia virus.

6. The method of claim 5, wherein the vaccinia virus is a Lister strain virus.

7. The method of claim 5, wherein the vaccinia virus is an LIVP virus or clonal variant of an LIVP virus.

8. The method of claim 7, wherein the virus is the variant of the LIVP virus that is the virus designated GLV-Ih68.

9. The method of claim 1, wherein the β-glucuronidase is a human or bacterial β-glucuronidase.

10. The method of claim 9, wherein the β-glucuronidase comprises the amino acid sequence set forth in SEQ ID NO: 121, or a catalytically active portion thereof, or the amino acid sequence having at least 85% sequence identity to the amino acid sequence set forth in SEQ ID NO:121.

11. The method of claim 9, wherein the β-glucuronidase comprises the amino acid sequence set forth in SEQ ID NO:4, or a catalytically active portion thereof, or the amino acid sequence having at least 85% sequence identity to the amino acid sequence set forth in SEQ ID NO:4.

12. The method of claim 9, wherein the β-glucuronidase comprises the amino acid sequence set forth in any of SEQ ID NOS: 4, 114-121, 128, 130, 132, 134, 136, 138, 140, 142, 144 and 146, or a catalytically active portion thereof, or the amino acid sequence having at least 85% sequence identity to the amino acid sequence set forth in any of SEQ ID NOS: 4, 114-121, 128, 130, 132, 134, 136, 138, 140, 142, 144 and 146.

13. The method of claim 1, wherein the substrate from the group consisting of fluorescein di-β-D-glucuronide (FDG-lcU), 4-methylumbelliferyl-β-D-glucuronide (4-MUG), carboxyumbelliferyl β-D-glucuronide (CUGlcU), 5-(pentafluorobenzoylamino)-fluorescein di-β-D-glucuronide (PFB-FDGlcU), C12-fluorescein β-D-Glucuronidase, 5-bromo-4-chloro-3-indolyl β-D-glucuronide (X-GlcU or BCIG), p-nitrophenyl- β-D-glucuronide, red-β-D-GlcU, CHA (magenta-b-D-GlcA; 5-bromo-6-chloro-3-indolyl-b-D-glucuronide, cyclohexylammonium salt), rose-β-D -GlcU, CHA (salmon-β-D-GlcUA; 5-bromo-6-chloro-3-indolyl-β-D -glucuronide, cyclohexylammonium salt), phenyl-β-D-glucuronide, and pharmaceutically acceptable salts thereof.

14. The method of claim 13, wherein the substrate is selected from among fluorescein di-β-D-glucuronide (FDGIcU) and 4-methylumbelliferyl-β-D-glucuronide (4-MUG).

15. The method of claim 1, wherein the sample is a body fluid that is selected from among blood, plasma, serum, lymph, ascetic fluid, cystic fluid, urine, nipple exudates, sweat, tears, saliva, mouth gargle, peritoneal fluid, cerebrospinal fluid (CSF), synovial fluid, aqueous humour, vitreous humour, amniotic fluid, bile, cerumen (earwax), Cowper's fluid (pre-ejaculatory fluid), Chyle, Chyme, female ejaculate, interstitial fluid, lymph fluid, menses, breast milk, mucus, snot, phlegm, pleural fluid, pus, sebum, semen, vaginal lubrication, and feces.

16. The method of claim 15, wherein the sample is collected between or between about 12 hours to 1 month after treatment with the oncolytic virus.

17. The method of claim 15, wherein the sample is obtained within 1 week of treatment with the virus, and detection of the β-glucuronidase activity in the sample indicates that the virus is replicating in tumor cells and is effective for treatment.

18. The method of claim 15, wherein the sample is obtained periodically following administration of the virus to monitor the progress of treatment by detecting an increase in amount of β-glucuronidase in the sample, indicating replication of the virus in tumors, followed by a decrease indicating that tumors are shrinking.

19. The method of claim 1, wherein the cancer comprises a bladder tumor, breast tumor, prostate tumor, glioma tumor, adenocarcinoma, ovarian carcinoma, and pancreatic carcinoma, liver tumor, skin tumor, pancreatic cancer, non-small cell lung cancer, multiple myeloma, leukemia, lung and bronchus tumor, breast tumor, colon and rectum tumor, kidney tumor, stomach tumor, esophagus tumor, liver and intrahepatic bile duct tumor, urinary bladder tumor, brain tumor and other nervous system tumor, head and neck tumor, oral cavity tumor and pharynx tumor, cervix tumor, uterine corpus tumor, thyroid tumor, ovary tumor, testes tumor, prostate tumor, malignant melanoma, cholangiocarcinoma, thymoma, non-melanoma skin cancer; hematologic tumor, malignancy, childhood leukemia and lymphoma, multiple myeloma, Hodgkin's disease, lymphomas of lymphocytic and cutaneous origin, acute and chronic leukemia, acute lymphoblastic leukemia, acute myelocytic leukemia, chronic myelocytic leukemia, plasma cell neoplasm or lymphoid neoplasm or is a cancer associated with HIV infection.

20. The method of claim 1, wherein the cancer is a solid tumor.

\* \* \* \* \*

UNITED STATES PATENT AND TRADEMARK OFFICE
CERTIFICATE OF CORRECTION

| | |
|---|---|
| PATENT NO. | : 8,859,256 B2 |
| APPLICATION NO. | : 13/573845 |
| DATED | : October 14, 2014 |
| INVENTOR(S) | : Szalay et al. |

It is certified that error appears in the above-identified patent and that said Letters Patent is hereby corrected as shown below:

IN THE SPECIFICATION:

At column 30, line 45, please replace "*Pectimidae*" with —*Pectiniidae*—;

at column 32, Table 1, row 3, column 3, please replace "phenylanine" with —phenylalanine—;

at column 34, line 14, please replace "Lipton" with —Lipman—;

at column 52, line 6, please replace "Chordopoxyiridae" with —Chordopoxviridae—;

at column 52, line 9, please replace "Entomopoxyirinae" with —Entomopoxvirinae—;

at column 52, lines 11-12, please replace "chordopoxyiridae" with —chordopoxviridae—;

at column 52, line 17, please replace "chordopoxyiridae" with —chordopoxviridae—;

at column 53, line 22, please replace "H-ID-W" with —IHD-W—;

at column 53, line 32, please replace "designed" with —designated—;

at column 54, line 26, please replace "14L" with —I4L—;

at column 61, lines 2-3, please replace "*Pseudomonas* A endotoxin" with —*Pseudomonas* exotoxin—;

at column 62, line 37, please replace "75.1" with —751—;

at column 68, line 57, please replace "151T" with —I51T—;

at column 68, line 58, please replace "R148c" with —R148C—;

at column 72, Table 3, row 17, column 3, please replace "cyclohexylammmonium salt" with —cyclohexylammonium salt—;

at column 77, line 34, please replace "1 gig" with —1 μg—;

at column 88, line 49, please replace "GLV-1668" with —GLV-1h68—;

at column 89, line 59, please replace "rVACV-gusZ" with —rVACV-gusA⁻—;

at column 90, Table 4, row 5, column 3, please replace "TK: ($P_{SLL}$)mMCP-1" with Signed and Sealed this
Seventeenth Day of March, 2015

Michelle K. Lee
*Director of the United States Patent and Trademark Office*

CERTIFICATE OF CORRECTION (continued)
U.S. Pat. No. 8,859,256 B2

—TK: (P$_{SL}$)mMCP-1—; and at column 91, line 61, please replace "Assistant" with —Assistent—.

IN THE CLAIMS:

Column 99, line 37 to line 54 should read

1. A method for treating cancer and monitoring therapeutic progress in a subject having tumors, said method comprising:

a) administering to said subject an oncolytic virus encoding a β-glucuronidase, wherein said oncolytic virus targets and treats cancer and the β-glucuronidase activity indicates oncolytic viral colonization or replication in said cancer;

b) obtaining a sample from a subject, wherein said sample is a body fluid or tissue sample that is not a tumor sample;

c) detecting β-glucuronidase activity in the sample, wherein said detection is by the addition of a substrate for β-glucuronidase; and d) determining the presence of a product catalyzed by the reaction of the β-glucuronidase with the substrate, wherein the detection of the product indicates that the oncolytic virus has colonized or is replicating in a tumor tissue or cell in the subject and is treating said tumor tissue or cell and oncolytic viral therapy is continued.

Column 100, line 42 to line 43 should read

8. The method of claim 7, wherein the virus is the variant of the LIVP virus that is the virus designated GLV-1h68.

Column 100, line 62 to column 101, line 7 should read

13. The method of claim 1, wherein the substrate is selected from the group consisting of fluorescein di-β-D-glucuronide (FDGlcU), 4-methylumbelliferyl-β-D-glucuronide (4-MUG), carboxyumbelliferyl β-D-glucuronide (CUGlcU), 5-(pentafluorobenzoylamino)-fluorescein di-β-D-glucuronide (PFB-FDGlcU), C$_{12}$-fluorescein β-D-Glucuronidase, 5-bromo-4-chloro-3-indolyl β-D-glucuronide (X-GlcU or BCIG), p-nitrophenyl- β-D-glucuronide, red-β-D-GlcU,CHA (magenta-β-D-GlcA; 5-bromo-6-chloro-3-indolyl-b-D-glucuronide, cyclohexylammonium salt), rose-β-D -GlcU,CHA (salmon-β-D-GlcUA; 5-bromo-6-chloro-3-indolyl-β-D -glucuronide, cyclohexylammonium salt), phenyl-β-D-glucuronide, and pharmaceutically acceptable salts thereof.

Column 100, line 62 to column 101, line 7 should read

14. The method of claim 13, wherein the substrate is selected from among fluorescein di-β-D-glucuronide (FDGlcU) and 4-methylumbelliferyl-β-D-glucuronide (4-MUG).